(12) United States Patent
Liao et al.

(10) Patent No.: US 8,372,407 B2
(45) Date of Patent: Feb. 12, 2013

(54) CHIMERIC HIV FUSION PROTEINS AS VACCINES

(75) Inventors: Chao-Wei Liao, Shin-Chu (TW); Hsiu-Kang Chang, Taipei (TW)

(73) Assignee: TheVax Genetics Vaccine Co., Ltd., Taipei (TW)

( * ) Notice: Subject to any disclaimer, the term of this patent is extended or adjusted under 35 U.S.C. 154(b) by 0 days.

(21) Appl. No.: 13/452,358

(22) Filed: Apr. 20, 2012

(65) Prior Publication Data

US 2012/0213811 A1    Aug. 23, 2012

Related U.S. Application Data

(62) Division of application No. 12/358,659, filed on Jan. 23, 2009, now abandoned.

(60) Provisional application No. 61/025,094, filed on Jan. 31, 2008.

(51) Int. Cl.
*A61K 39/21* (2006.01)
*A61K 39/295* (2006.01)

(52) U.S. Cl. ............. 424/188.1; 424/192.1; 424/201.1

(58) Field of Classification Search ............... None
See application file for complete search history.

(56) References Cited

U.S. PATENT DOCUMENTS

| 7,314,632 B1 | 1/2008 | Fitzgerald |
| 2005/0106160 A1 | 5/2005 | Dimitrov |

OTHER PUBLICATIONS

Vandepapeliere P. "Therapeutic vaccination against chronic viral infections" The LANCET Infectious Diseases vol. 2 Jun. 2002.*
(Pontesilli O. et al. "Phase II controlled trial of post-exposure immunization with recombinant gp160 versus antiretroviral therapy in asymptomatic HIV-1-infected adults" AIDS 1998, 12:473-480.*
Sandstrom E. et al. "Therapeutic immunisation with recombinant gp160 in HIV-1 infection: a randomised double-blind placebo-controlled trial" The Lancet 353:173501742, 1999.*
Puls R. "Therapeutic vaccination against HIV: current progress and future possibilities" Clinical Science (2006) 110: 59-71.*
Rey-Cuille "HIV-1 neutralizing antibodies elicited by the candidate CBD1 epitope vaccine react with the conserved caveolin-1 binding motif of viral glycoprotein gp41" J. of Pharmacy and Pharmacology 2006, 58:759-767.*

* cited by examiner

*Primary Examiner* — Zachariah Lucas
*Assistant Examiner* — Nicole Kinsey White
(74) *Attorney, Agent, or Firm* — Hsiu-Ming Saunders Intellectual Property Connections, Inc.

(57) ABSTRACT

A method for inducing HIV antigen-specific immune responses is disclosed. The method comprises administering to a subject in need thereof a therapeutically effective amount of a chimeric fusion protein comprising: (a) a first polypeptidyl region comprising a *Pseudomonas Exotoxin* A (PE) binding domain and a PE translocation domain, located at the N-terminus of the fusion protein; and (b) a second polypeptidyl region with a fusion peptide of HIV gp120-C1-C5-gp41 with the amino acid sequence of SEQ ID NO: 7. A method for inducing neutralizing antibodies against HIV-1 is also disclosed.

12 Claims, 6 Drawing Sheets

SEQUENCE LISTING

```
<160> NUMBER OF SEQ ID NOS: 252

<210> SEQ ID NO 1
<211> LENGTH: 16
<212> TYPE: PRT
<213> ORGANISM: Human immunodeficiency virus

<400> SEQUENCE: 1

Val Glu Lys Leu Trp Val Thr Val Tyr Tyr Gly Val Pro Val Trp Lys
1               5                   10                  15

<210> SEQ ID NO 2
<211> LENGTH: 25
<212> TYPE: PRT
<213> ORGANISM: Human immunodeficiency virus

<400> SEQUENCE: 2

Lys Val Val Lys Ile Glu Pro Leu Gly Val Ala Pro Thr Lys Cys Lys
1               5                   10                  15

Arg Arg Val Val Gln Arg Glu Lys Arg
            20                  25

<210> SEQ ID NO 3
<211> LENGTH: 35
<212> TYPE: PRT
<213> ORGANISM: Human immunodeficiency virus

<400> SEQUENCE: 3

Cys Thr Arg Pro Ser Asn Asn Thr Arg Lys Gly Ile His Met Gly Pro
1               5                   10                  15

Gly Gly Ala Phe Tyr Thr Thr Gly Gln Ile Ile Arg Asn Ile Arg Gln
            20                  25                  30

Ala His Cys
        35

<210> SEQ ID NO 4
<211> LENGTH: 35
<212> TYPE: PRT
<213> ORGANISM: Human immunodeficiency virus

<400> SEQUENCE: 4

Cys Thr Arg Pro Asn Asn Asn Thr Arg Arg Ser Ile His Ile Glu Pro
1               5                   10                  15

Glu Gly Ala Phe Tyr Thr Thr Gly Glu Ile Ile Gly Asp Ile Arg Gln
            20                  25                  30

Ala His Cys
        35

<210> SEQ ID NO 5
<211> LENGTH: 54
<212> TYPE: PRT
<213> ORGANISM: Human immunodeficiency virus

<400> SEQUENCE: 5

Gln Ala Arg Val Ile Ala Val Glu Arg Tyr Leu Lys Asp Gln Gln Leu
```

```
                   1               5                  10                 15
Leu Gly Ile Trp Gly Gly Ser Gly Lys Leu Ile Cys Cys Thr Thr Ala
                       20                 25                 30

Val Pro Trp Asn Ser Ser Trp Ser Asn Lys Leu Asp Arg Ile Trp Asn
            35                 40                 45

Asn Met Thr Trp Leu Glu
     50

<210> SEQ ID NO 6
<211> LENGTH: 82
<212> TYPE: PRT
<213> ORGANISM: Artificial sequence
<220> FEATURE:
<223> OTHER INFORMATION: Chimera HIV gP120 V3-V3

<400> SEQUENCE: 6

Ile Gly Cys Thr Arg Pro Ser Asn Asn Thr Arg Lys Gly Ile His Met
1               5                  10                 15

Gly Pro Gly Gly Ala Phe Tyr Thr Thr Gly Gln Ile Ile Arg Asn Ile
            20                 25                 30

Arg Gln Ala His

-continued

```
cacatgggcc cgggtggtgc tttctacacc accggtcaga tcatccgtaa catccgtcag    120
gctcactgtg gtctgctggg tggttgtacc cgtccgaaca acaacacccg tcgtagcatc    180
cacatcgaac cggaaggtgc tttctacacc accggtgaaa tcatcggtga catccgtcag    240
gctcactgtg gcctgggtct cgag                                           264
```

<210> SEQ ID NO 9
<211> LENGTH: 318
<212> TYPE: DNA
<213> ORGANISM: Artificial sequence
<220> FEATURE:
<223> OTHER INFORMATION: chimeric gene HIV gP120 C1-C5-gp41

<400> SEQUENCE: 9

```
gaattccata tggtcgacgt tgaaaaactg tgggttaccg tttactacgg tgttccggtt     60
tggaaaaaag ttgttaaaat cgaaccgctg ggtgttgctc cgaccaaatg caaacgtcgt    120
gttgttcagc gtgaaaagcg tggtggcggt ggcggtcaag ctcgtgttat cgctgttgaa    180
cgttacctga agaccagca gctgctgggt atctggggtg gtagcggtaa actgatctgc    240
tgcaccaccg ctgttccgtg aacagcagc tggagcaaca aactggaccg tatctggaac    300
aacatgacct ggctcgag                                                  318
```

<210> SEQ ID NO 10
<211> LENGTH: 40
<212> TYPE: DNA
<213> ORGANISM: Artificial sequence
<220> FEATURE:
<223> OTHER INFORMATION: Forward primer F1 for chimeric gene HIV gP120
      V3-V3

<400> SEQUENCE: 10

```
catccgtaac atccgtcagg ctcactgtgg tctgctgggt                           40
```

<210> SEQ ID NO 11
<211> LENGTH: 39
<212> TYPE: DNA
<213> ORGANISM: Artificial sequence
<220> FEATURE:
<223> OTHER INFORMATION: Forward primer F2 for chimeric gene HIV gP120
      V3-V3

<400> SEQUENCE: 11

```
gctttctaca ccaccggtca gatcatccgt aacatccgt                            39
```

<210> SEQ ID NO 12
<211> LENGTH: 42
<212> TYPE: DNA
<213> ORGANISM: Artificial sequence
<220> FEATURE:
<223> OTHER INFORMATION: Forward primer F3 for chimeric gene HIV gP120
      V3-V3

<400> SEQUENCE: 12

```
aaaggtatcc acatgggccc gggtggtgct ttctacacca cc                        42
```

<210> SEQ ID NO 13
<211> LENGTH: 39
<212> TYPE: DNA
<213> ORGANISM: Artificial sequence
<220> FEATURE:
<223> OTHER INFORMATION: Forward primer F4 for chimeric gene HIV gP120
      V3-V3

<400> SEQUENCE: 13
acccgtccga gcaacaacac ccgtaaaggt atccacatg            39

<210> SEQ ID NO 14
<211> LENGTH: 46
<212> TYPE: DNA
<213> ORGANISM: Artificial sequence
<220> FEATURE:
<223> OTHER INFORMATION: Forward primer F5 for chimeric gene HIV gP120
      V3-V3

<400> SEQUENCE: 14
cccgaattcc atatggtcga catcggttgc acccgtccga gcaaca            46

<210> SEQ ID NO 15
<211> LENGTH: 39
<212> TYPE: DNA
<213> ORGANISM: Artificial sequence
<220> FEATURE:
<223> OTHER INFORMATION: Reverse primer R1 for chimeric gene HIV gP120
      V3-V3

<400> SEQUENCE: 15
gttgttgttc ggacgggtac aaccacccag cagaccaca 39

<210> SEQ ID NO 16
<211> LENGTH: 39
<212> TYPE: DNA
<213> ORGANISM: Artificial sequence
<220> FEATURE:
<223> OTHER INFORMATION: Reverse primer R2 for chimeric gene HIV gP120 V3-V3

<400> SEQUENCE: 16
ttcgatgtgg atgctacgac gggtgttgtt gttaggacg 39

<210> SEQ ID NO 17
<211> LENGTH: 39
<212> TYPE: DNA
<213> ORGANISM: Artificial sequence
<220> FEATURE:
<223> OTHER INFORMATION: Reverse primer R3 for chimeric gene HIV gP120 V3-V3

<400> SEQUENCE: 17
ggtggtgtag aaagcacctt ccggttcgat gtggatgct 39

<210> SEQ ID NO 18
<211> LENGTH: 39
<212> TYPE: DNA
<213> ORGANISM: Artificial sequence
<220> FEATURE:
<223> OTHER INFORMATION: Reverse primer R4 for chimeric gene HIV gP120 V3-V3

<400> SEQUENCE: 18
acggatatca ccgatgattt caccggtggt gtagaaagc 39

<210> SEQ ID NO 19
<211> LENGTH: 64
<212> TYPE: DNA
<213> ORGANISM: Artificial sequence
<220> FEATURE:
<223> OTHER INFORMATION: Reverse primer R5 for chimeric gene HIV gP120 V3-V3

<400> SEQUENCE: 19
aaaaaaattc ccattatttt tctcgagacc caggccacag tgagcctgac ggatgtcacc 60
gatg                                                                    64

<210> SEQ ID NO 20
<211> LENGTH: 44
<212> TYPE: DNA
<213> ORGANISM: Artificial sequence
<220> FEATURE:
<223> OTHER INFORMATION: Forward primer F1 for chimeric gene HIV gP120
      C1-C4-gp41

<400> SEQUENCE: 20
gttgctccga ccaaatgcaa acgtcgtgtt gttcagcgtg aaaa              44

<210> SEQ ID NO 21
<211> LENGTH: 47
<212> TYPE: DNA
<213> ORGANISM: Artificial sequence
<220> FEATURE:
<223> OTHER INFORMATION: Forward primer F2 for chimeric gene HIV gP120
      C1-C4-gp41

<400> SEQUENCE: 21
aaaaaagttg ttaaaatcga accgctgggt gttgctccga ccaaatg           47

<210> SEQ ID NO 22
<211> LENGTH: 49
<212> TYPE: DNA
<213> ORGANISM: Artificial sequence
<220> FEATURE:
<223> OTHER INFORMATION: Forward primer F3 for chimeric gene HIV gP120
      C1-C4-gp41

<400> SEQUENCE: 22
gtgggttacc gtttactacg gtgttccggt ttggaaaaaa gttgttaaa         49

<210> SEQ ID NO 23
<211> LENGTH: 49
<212> TYPE: DNA
<213> ORGANISM: Artificial sequence
<220> FEATURE:
<223> OTHER INFORMATION: Forward primer F4 for chimeric gene HIV gP120
      C1-C4-gp41

<400> SEQUENCE: 23
cccgaattcc atatggtcga cgttgaaaaa ctgtgggtta ccgtttact         49

<210> SEQ ID NO 24
<211> LENGTH: 54
<212> TYPE: DNA
<213> ORGANISM: Artificial sequence
<220> FEATURE:
<223> OTHER INFORMATION: Reverse primer R1 for chimeric gene HIV gP120
      C1-C4-gp41

<400> SEQUENCE: 24
aacagcgata acacgagctt gaccgccacc gccaccacgc ttttcacgct gaac   54

<210> SEQ ID NO 25
<211> LENGTH: 46
<212> TYPE: DNA
<213> ORGANISM: Artificial sequence
<220> FEATURE:
<223> OTHER INFORMATION: Reverse primer R2 for chimeric gene HIV gP120
      C1-C4-gp41

<400> SEQUENCE: 25
cagcagctgc tggtctttca ggtaacgttc aacagcgata acacga            46

```
<210> SEQ ID NO 26
<211> LENGTH: 44
<212> TYPE: DNA
<213> ORGANISM: Artificial sequence
<220> FEATURE:
<223> OTHER INFORMATION: Reverse primer R3 for chimeric gene HIV gP120
      C1-C4-gp41

<400> SEQUENCE: 26
gatcagttta ccgctaccac cccagatacc cagcagctgc tggt                44

<210> SEQ ID NO 27
<211> LENGTH: 45
<212> TYPE: DNA
<213> ORGANISM: Artificial sequence
<220> FEATURE:
<223> OTHER INFORMATION: Reverse primer R4 for chimeric gene HIV gP120
      C1-C4-gp41

<400> SEQUENCE: 27
gctgttccac ggaacagcgg tggtgcagca gatcagttta ccgct             45

<210> SEQ ID NO 28
<211> LENGTH: 44
<212> TYPE: DNA
<213> ORGANISM: Artificial sequence
<220> FEATURE:
<223> OTHER INFORMATION: Reverse primer R5 for chimeric gene HIV gP120
      C1-C4-gp41

<400> SEQUENCE: 28
ccagatacgg tccagtttgt tgctccagct gctgttccac ggaa                44

<210> SEQ ID NO 29
<211> LENGTH: 39
<212> TYPE: DNA
<213> ORGANISM: Artificial sequence
<220> FEATURE:
<223> OTHER INFORMATION: Reverse primer R6 for chimeric gene HIV gP120
      C1-C4-gp41

<400> SEQUENCE: 29
aaactcgagc caggtcatgt tgttccagat acggtccag                      39

<210> SEQ ID NO 30
<211> LENGTH: 4
<212> TYPE: PRT
<213> ORGANISM: Artificial sequence
<220> FEATURE:
<223> OTHER INFORMATION: Carboxyl terminal moiety KDEL

<400> SEQUENCE: 30

Lys Asp Glu Leu
1

<210> SEQ ID NO 31
<211> LENGTH: 98
<212> TYPE: PRT
<213> ORGANISM: Artificial sequence
<220> FEATURE:
<223> OTHER INFORMATION: Chimera for HIV subtype A gp120 C1-C5-gp41

<400> SEQUENCE: 31

Ala Glu Asn Leu Trp Val Thr Val Tyr Tyr Gly Val Pro Ile Trp Lys
1               5                   10                  15

Lys Val Val Lys Ile Glu Pro Leu Gly Val Ala Pro Thr Lys Ala Arg
```

```
            20                  25                  30

Arg Arg Val Val Glu Arg Glu Lys Arg Gly Gly Gly Gly Gly Gln Ala
        35                  40                  45

Arg Val Leu Ala Val Glu Arg Tyr Leu Arg Asp Gln Gln Leu Leu Gly
    50                  55                  60

Ile Trp Gly Cys Ser Gly Lys Leu Ile Cys Pro Thr Asn Val Pro Trp
65                  70                  75                  80

Asn Ser Ser Trp Ser Asn Lys Ser Leu Asp Glu Ile Trp Glu Asn Met
                85                  90                  95

Thr Trp

<210> SEQ ID NO 32
<211> LENGTH: 98
<212> TYPE: PRT
<213> ORGANISM: Artificial sequence
<220> FEATURE:
<223> OTHER INFORMATION: Chimera for HIV subtype B gp120 C1-C5-gp41

<400> SEQUENCE: 32

Thr Glu Lys Leu Trp Val Thr Val Tyr Tyr Gly Val Pro Val Trp Lys
1               5                   10                  15

Lys Val Val Lys Ile Glu Pro Leu Gly Ile Ala Pro Thr Lys Ala Lys
            20                  25                  30

Arg Arg Val Val Gln Arg Glu Lys Arg Gly Gly Gly Gly Gly Gln Ala
        35                  40                  45

Arg Val Leu Ala Leu Glu Arg Tyr Leu Arg Asp Gln Gln Leu Leu Gly
    50                  55                  60

Ile Trp Gly Cys Ser Gly Lys Leu Ile Cys Thr Thr Thr Val Pro Trp
65                  70                  75                  80

Asn Ala Ser Trp Ser Asn Arg Ser Leu Asp Glu Ile Trp Asp Asn Met
                85                  90                  95

Thr Trp

<210> SEQ ID NO 33
<211> LENGTH: 100
<212> TYPE: PRT
<213> ORGANISM: Artificial sequence
<220> FEATURE:
<223> OTHER INFORMATION: Chimera for HIV subtype C gp120 C1-C5-gp41

<400> SEQUENCE: 33

Met Gly Asn Leu Trp Val Thr Val Tyr Tyr Gly Val Pro Val Trp Lys
1               5                   10                  15

Lys Tyr Lys Val Val Glu Ile Lys Pro Leu Gly Val Ala Pro Thr Lys
            20                  25                  30

Pro Lys Arg Arg Val Val Glu Arg Glu Lys Arg Gly Gly Gly Gly Gly
        35                  40                  45

Gln Thr Arg Val Leu Ala Ile Glu Arg His Leu Arg Asp Gln Gln Leu
    50                  55                  60

Leu Gly Ile Trp Gly Cys Ser Gly Lys Leu Ile Cys Thr Thr Ala Val
65                  70                  75                  80

Pro Trp Asn Ser Ser Trp Ser Asn Lys Ser Gln Glu Glu Ile Trp Asp
                85                  90                  95

Asn Met Thr Trp
            100

<210> SEQ ID NO 34
<211> LENGTH: 98
```

```
<212> TYPE: PRT
<213> ORGANISM: Artificial sequence
<220> FEATURE:
<223> OTHER INFORMATION: Chimera for HIV subtype D gp120 C1-C5-gp41

<400> SEQUENCE: 34

Ala Asp Asn Leu Trp Val Thr Val Tyr Tyr Gly Val Pro Val Trp Lys
1               5                   10                  15

Lys Val

-continued

```
Arg Val Leu Ala Val Glu Arg Tyr Leu Lys Asp Gln Gln Leu Leu Gly
         50                  55                  60

Ile Trp Gly Cys Ser Gly Lys Leu Ile Cys Thr Thr Asn Val Pro Trp
 65                  70                  75                  80

Asn Ser Ser Trp Ser Asn Lys Ser Gln Glu Glu Ile Trp Asn Asn Met
                 85                  90                  95

Thr Trp

<210> SEQ ID NO 37
<211> LENGTH: 102
<212> TYPE: PRT
<213> ORGANISM: Artificial sequence
<220> FEATURE:
<223> OTHER INFORMATION: Chimera for HIV subtype G gp120 C1-C5-gp41

<400> SEQUENCE: 37

Ala Ser Asn Asn Leu Trp Val Thr Val Tyr Tyr Gly Val Pro Val Trp
 1               5                  10                  15

Glu Asp Ala Lys Lys Val Val Lys Ile Lys Pro Leu Gly Val Ala Pro
                20                  25                  30

Thr Lys Ala Arg Arg Val Val Gly Arg Glu Lys Arg Gly Gly Gly
             35                  40                  45

Gly Gly Gln Ala Arg Val Leu Ala Leu Glu Arg Tyr Leu Arg Asp Gln
         50                  55                  60

Gln Leu Leu Gly Ile Trp Gly Cys Ser Gly Lys Leu Ile Cys Thr Thr
 65                  70                  75                  80

Asn Val Pro Trp Asn Ala Ser Trp Ser Asn Lys Thr Tyr Asn Asp Ile
                 85                  90                  95

Trp Asp Asn Met Thr Trp
            100

<210> SEQ ID NO 38
<211> LENGTH: 102
<212> TYPE: PRT
<213> ORGANISM: Artificial sequence
<220> FEATURE:
<223> OTHER INFORMATION: Chimera for HIV subtype H gp120 C1-C5-gp41

<400> SEQUENCE: 38

Val Val Gly Asn Leu Trp Val Thr Val Tyr Tyr Gly Val Pro Val Trp
 1               5                  10                  15

Lys Lys Val Val Lys Ile Glu Pro Leu Gly Val Ala Pro Thr Glu Ala
                20                  25                  30

Arg Arg Arg Val Val Glu Arg Glu Lys Arg Gly Gly Gly Gly Gln
             35                  40                  45

Ala Arg Val Leu Ala Val Glu Arg Tyr Leu Lys Asp Gln Gln Leu Leu
         50                  55                  60

Gly Ile Trp Gly Cys Ser Gly Lys Leu Ile Cys Thr Thr Asn Val Pro
 65                  70                  75                  80

Trp Asn Ser Ser Trp Ser Asn Lys Ser Leu Asp Glu Ile Trp Asp Asn
                 85                  90                  95

Met Thr Trp Met Glu Trp
            100

<210> SEQ ID NO 39
<211> LENGTH: 99
<212> TYPE: PRT
<213> ORGANISM: Artificial sequence
<220> FEATURE:
<223> OTHER INFORMATION: Chimera for HIV subtype J gp120 C1-C5-gp41
```

-continued

<400> SEQUENCE: 39

Ala Lys Glu Asp Leu Trp Val Thr Val Tyr Tyr Gly Val Pro Val Trp
1               5                   10                  15
Lys Lys Val Val Glu Ile Glu Pro Leu Gly Val Ala Pro Thr Lys Ala
            20                  25                  30
Lys Arg Arg Val Val Glu Arg Glu Lys Arg Gly Gly Gly Gly Gly Gln
        35                  40                  45
Ala Arg Val Leu Ala Val Glu Arg Tyr Leu Lys Asp Gln Gln Leu Leu
    50                  55                  60
Gly Ile Trp Gly Cys Ser Gly Lys Leu Ile Cys Thr Thr Asn Val Pro
65                  70                  75                  80
Trp Asn Ala Ser Trp Ser Asn Lys Ser Tyr Glu Asp Ile Trp Glu Asn
                85                  90                  95
Met Thr Trp

<210> SEQ ID NO 40
<211> LENGTH: 99
<212> TYPE: PRT
<213> ORGANISM: Artificial sequence
<220> FEATURE:
<223> OTHER INFORMATION: Chimera for HIV subtype K gp120 C1-C5-gp41

<400> SEQUENCE: 40

Ala Ala Asn Asn Leu Trp Val Thr Val Tyr Tyr Gly Val Pro Val Trp
1               5                   10                  15
Lys Lys Val Val Gln Ile Glu Pro Leu Gly Ile Ala Pro Thr Arg Ala
            20                  25                  30
Arg Arg Arg Val Val Gln Arg Glu Lys Arg Gly Gly Gly Gly Gly Arg
        35                  40                  45
Ala Arg Val Leu Ala Val Glu Arg Tyr Leu Arg Asp Gln Gln Leu Leu
    50                  55                  60
Gly Ile Trp Gly Cys Ser Gly Lys Leu Ile Cys Thr Thr Asn Val Pro
65                  70                  75                  80
Trp Asn Ser Ser Trp Ser Asn Lys Ser Gln Ser Glu Ile Trp Glu Asn
                85                  90                  95
Met Thr Trp

<210> SEQ ID NO 41
<211> LENGTH: 294
<212> TYPE: DNA
<213> ORGANISM: Artificial sequence
<220> FEATURE:
<223> OTHER INFORMATION: Chimeric gene for HIV subtype A gp120
      C1-C5-gp41

<400> SEQUENCE: 41
gctgaaaacc tgtgggttac cgtttactac ggtgttccaa tctggaaaaa agttgttaaa      60
atcgaaccac tgggtgttgc tccaaccaaa gctcgtcgtc gtgttgttga acgtgaaaaa     120
cgtggtggtg gtggtggtca ggctcgtgtt ctggctgttg aacgttacct gcgtgaccag     180
cagctgctgg gtatctgggg ttgttccggt aaactgatct gtccaaccaa cgttccatgg     240
aactcctcct ggtccaacaa atccctggac gaaatctggg aaaacatgac ctgg           294

<210> SEQ ID NO 42
<211> LENGTH: 294
<212> TYPE: DNA
<213> ORGANISM: Artificial sequence
<220> FEATURE:

```
<223> OTHER INFORMATION: Chimeric gene for HIV subtype B gp120
      C1-C5-gp41

<400> S

```
<211> LENGTH: 294
<212> TYPE: DNA
<213> ORGANISM: Artificial sequence
<220> FEATURE:
<223> OTHER INFORMATION: Chimeric gene for HIV subtype F gp120
      C1-C5-gp41

<400> SEQUENCE: 46
gctgacaacc tgtgggttac cgtttactac ggtgttccag tgtggaaaaa agttgttgaa      60
atcgaaccac tgggtgttgc tccaaccaaa gctaaacgtc aggttgttca gcgtgaaaaa     120
cgtggtggtg gtggtggtca ggctcgtgtt ctggctgttg aacgttacct gaaagaccag     180
cagctgctgg gtatctgggg ttgttccggt aaactgatct gtaccaccaa cgttccatgg     240
aactcctcct ggtccaacaa atcccaggaa gaaatctgga caacatgac ctgg            294

<210> SEQ ID NO 47
<211> LENGTH: 306
<212> TYPE: DNA
<213> ORGANISM: Artificial sequence
<220> FEATURE:
<223> OTHER INFORMATION: Chimeric gene for HIV subtype G gp120
      C1-C5-gp41

<400> SEQUENCE: 47
gcttccaaca acctgtgggt taccgtttac tacggtgttc cagtgtggga agacgctaaa      60
aaagttgtta aaatcaaacc actgggtgtt gctccaacca aagctcgtcg tcgtgttgtt     120
ggtcgtgaaa acgtggtgg tggtggtggt caggctcgtg ttctggctct ggaacgttac      180
ctgcgtgacc agcagctgct gggtatctgg ggttgttccg gtaaactgat ctgtaccacc     240
aacgttccat ggaacgcttc ctggtccaac aaaacctaca cgacatctg ggacaacatg     300 acctgg                                                                306

<210> SEQ ID NO 48
<211> LENGTH: 306
<212> TYPE: DNA
<213> ORGANISM: Artificial sequence
<220> FEATURE:
<223> OTHER INFORMATION: Chimeric gene for HIV subtype H gp120
      C1-C5-gp41

<400> SEQUENCE: 48
gttgttggta acctgtgggt taccgtttac tacggtgttc cagtgtggaa aaagttgtt       60 aaaatcgaac cactgggtgt tgctccaacc gaagctcgtc gtcgtgttgt tgaacgtgaa     120
aaacgtggtg gtggtggtgg tcaggctcgt gttctggctg ttgaacgtta cctgaaagac     180
cagcagctgc tgggtatctg gggttgttcc ggtaaactga tctgtaccac caacgttcca     240
tggaactcct cctggtccaa caaatccctg acgaaatct gggacaacat gacctggatg     300
gaatgg                                                                306

<210> SEQ ID NO 49
<211> LENGTH: 297
<212> TYPE: DNA
<213> ORGANISM: Artificial sequence
<220> FEATURE:
<223> OTHER INFORMATION: Chimeric gene for HIV subtype J gp120
      C1-C5-gp41

<400> SEQUENCE: 49
gctaaagaag acctgtgggt taccgtttac tacggtgttc cagtgtggaa aaagttgtt       60 gaaatcgaac cactgggtgt tgctccaacc aaagctaaac gtcgtgttgt tgaacgtgaa     120
```

```
aaacgtggtg gtggtggtgg tcaggctcgt gttctggctg ttgaacgtta cctgaaagac    180
cagcagctgc tgggtatctg ggttgttcc ggtaaactga tctgtaccac caacgttcca     240
tggaacgctt cctggtccaa caatcctac gaagacatct gggaaaacat gacctgg        297
```

<210> SEQ ID NO 50
<211> LENGTH: 297
<212> TYPE: DNA
<213> ORGANISM: Artificial sequence
<220> FEATURE:
<223> OTHER INFORMATION: Chimeric gene for HIV subtype K gp120
      C1-C5-gp41

<400> SEQUENCE: 50

```
gctgctaaca acctgtgggt taccgtttac tacggtgttc cagtgtggaa aaaagttgtt    60
cagatcgaac cactgggtat cgctccaacc cgtgctcgtc gtcgtgttgt tcagcgtgaa   120
aaacgtggtg gtggtggtgg tcgtgctcgt gttctggctg ttgaacgtta cctgcgtgac   180
cagcagctgc tgggtatctg ggttgttcc ggtaaactga tctgtaccac caacgttcca    240
tggaactcct cctggtccaa caatcccag tccgaaatct gggaaaacat gacctgg       297
```

<210> SEQ ID NO 51
<211> LENGTH: 45
<212> TYPE: DNA
<213> ORGANISM: Artificial sequence
<220> FEATURE:
<223> OTHER INFORMATION: Forward primer F1 for chimeric gene HIV subtype
      A gp120 C1-C5-gp41

<400> SEQUENCE: 51

```
gttgaacgtg aaaaacgtgg tggtggtggt ggtcaggctc gtgtt                    45
```

<210> SEQ ID NO 52
<211> LENGTH: 45
<212> TYPE: DNA
<213> ORGANISM: Artificial sequence
<220> FEATURE:
<223> OTHER INFORMATION: Forward primer F2 for chimeric gene HIV subtype
      A gp120 C1-C5-gp41

<400> SEQUENCE: 52

```
gttgctccaa ccaaagctcg tcgtcgtgtt gttgaacgtg aaaaa                    45
```

<210> SEQ ID NO 53
<211> LENGTH: 49
<212> TYPE: DNA
<213> ORGANISM: Artificial sequence
<220> FEATURE:
<223> OTHER INFORMATION: Forward primer F3 for chimeric gene HIV subtype
      A gp120 C1-C5-gp41

<400> SEQUENCE: 53

```
ctggaaaaaa gttgttaaaa tcgaaccact gggtgttgct ccaaccaaa                49
```

<210> SEQ ID NO 54
<211> LENGTH: 46
<212> TYPE: DNA
<213> ORGANISM: Artificial sequence
<220> FEATURE:
<223> OTHER INFORMATION: Forward primer F4 for chimeric gene HIV subtype
      A gp120 C1-C5-gp41

<400> SEQUENCE: 54

```
gtgggttacc gtttactacg gtgttccaat ctggaaaaaa gttgtt                   46
```

<210> SEQ ID NO 55
<211> LENGTH: 47
<212> TYPE: DNA
<213> ORGANISM: Artificial sequence
<220> FEATURE:
<223> OTHER INFORMATION: Forward primer F5 for chimeric gene HIV subtype
      A gp120 C1-C5-gp41

<400> SEQUENCE: 55
cccgaattcc atatggtcga cgctgaaaac ctgtgggtta ccgttta                47

<210> SEQ ID NO 56
<211> LENGTH: 47
<212> TYPE: DNA
<213> ORGANISM: Artificial sequence
<220> FEATURE:
<223> OTHER INFORMATION: Reverse primer R1 for chimeric gene HIV subtype
      A gp120 C1-C5-gp41

<400> SEQUENCE: 56
tgctggtcac gcaggtaacg ttcaacagcc agaacacgag cctgacc                47

<210> SEQ ID NO 57
<211> LENGTH: 46
<212> TYPE: DNA
<213> ORGANISM: Artificial sequence
<220> FEATURE:
<223> OTHER INFORMATION: Reverse primer R2 for chimeric gene HIV subtype
      A gp120 C1-C5-gp41

<400> SEQUENCE: 57
tttaccggaa caaccccaga tacccagcag ctgctggtca cgcagg                 46

<210> SEQ ID NO 58
<211> LENGTH: 46
<212> TYPE: DNA
<213> ORGANISM: Artificial sequence
<220> FEATURE:
<223> OTHER INFORMATION: Reverse primer R3 for chimeric gene HIV subtype
      A gp120 C1-C5-gp41

<400> SEQUENCE: 58
agttccatgg aacgttggtt ggacagatca gtttaccgga acaacc                 46

<210> SEQ ID NO 59
<211> LENGTH: 48
<212> TYPE: DNA
<213> ORGANISM: Artificial sequence
<220> FEATURE:
<223> OTHER INFORMATION: Reverse primer R4 for chimeric gene HIV subtype
      A gp120 C1-C5-gp41

<400> SEQUENCE: 59
tttcgtccag ggatttgttg gaccaggagg agttccatgg aacgttgg               48

<210> SEQ ID NO 60
<211> LENGTH: 49
<212> TYPE: DNA
<213> ORGANISM: Artificial sequence
<220> FEATURE:
<223> OTHER INFORMATION: Reverse primer R5 for chimeric gene HIV subtype
      A gp120 C1-C5-gp41

<400> SEQUENCE: 60
atttttctcg agccaggtca tgttttccca gatttcgtcc agggatttg              49

<210> SEQ ID NO 61
<211> LENGTH: 45

-continued

```
<212> TYPE: DNA
<213> ORGANISM: Artificial sequence
<220> FEATURE:
<223> OTHER INFORMATION: Forward primer F1 for chimeric gene HIV subtype
      B gp120 C1-C5-gp41

<400> SEQUENCE: 61
gttcagcgtg aaaaacgtgg tggtggtggt ggtcaggctc gtgtt                    45

<210> SEQ ID NO 62
<211> LENGTH: 46
<212> TYPE: DNA
<213> ORGANISM: Artificial sequence
<220> FEATURE:
<223> OTHER INFORMATION: Forward primer F2 for chimeric gene HIV subtype
      B gp120 C1-C5-gp41

<400> SEQUENCE: 62
atcgctccaa ccaaagctaa acgtcgtgtt gttcagcgtg aaaaac                   46

<210> SEQ ID NO 63
<211> LENGTH: 49
<212> TYPE: DNA
<213> ORGANISM: Artificial sequence
<220> FEATURE:
<223> OTHER INFORMATION: Forward primer F3 for chimeric gene HIV subtype
      B gp120 C1-C5-gp41

<400> SEQUENCE: 63
gtggaaaaaa gttgttaaaa tcgaaccact gggtatcgct ccaaccaaa                49

<210> SEQ ID NO 64
<211> LENGTH: 46
<212> TYPE: DNA
<213> ORGANISM: Artificial sequence
<220> FEATURE:
<223> OTHER INFORMATION: Forward primer F4 for chimeric gene HIV subtype
      B gp120 C1-C5-gp41

<400> SEQUENCE: 64
gtgggttacc gtttactacg gtgttccagt gtggaaaaaa gttgtt                   46

<210> SEQ ID NO 65
<211> LENGTH: 47
<212> TYPE: DNA
<213> ORGANISM: Artificial sequence
<220> FEATURE:
<223> OTHER INFORMATION: Forward primer F5 for chimeric gene HIV subtype
      B gp120 C1-C5-gp41

<400> SEQUENCE: 65
cccgaattcc atatggtcga caccgaaaaa ctgtgggtta ccgttta                  47

<210> SEQ ID NO 66
<211> LENGTH: 47
<212> TYPE: DNA
<213> ORGANISM: Artificial sequence
<220> FEATURE:
<223> OTHER INFORMATION: Reverse primer R1 for chimeric gene HIV subtype
      B gp120 C1-C5-gp41

<400> SEQUENCE: 66
tgctggtcac gcaggtaacg ttccagagcc agaacacgag cctgacc                  47

<210> SEQ ID NO 67
<211> LENGTH: 46
<212> TYPE: DNA
<213> ORGANISM: Artificial sequence
```

```
<220> FEATURE:
<223> OTHER INFORMATION: Reverse primer R2 for chimeric gene HIV subtype
      B gp120 C1-C5-gp41

<400> SEQUENCE: 67
tttaccggaa caacccccaga tacccagcag ctgctggtca cgcagg          46

<210> SEQ ID NO 68
<211> LENGTH: 48
<212> TYPE: DNA
<213> ORGANISM: Artificial sequence
<220> FEATURE:
<223> OTHER INFORMATION: Reverse primer R3 for chimeric gene HIV subtype
      B gp120 C1-C5-gp41

<400> SEQUENCE: 68
agcgttccat ggaacggtgg tggtacagat cagtttaccg gaacaacc          48

<210> SEQ ID NO 69
<211> LENGTH: 44
<212> TYPE: DNA
<213> ORGANISM: Artificial sequence
<220> FEATURE:
<223> OTHER INFORMATION: Reverse primer R4 for chimeric gene HIV subtype
      B gp120 C1-C5-gp41

<400> SEQUENCE: 69
atttcgtcca gggaacggtt ggaccaggaa gcgttccatg gaac              44

<210> SEQ ID NO 70
<211> LENGTH: 47
<212> TYPE: DNA
<213> ORGANISM: Artificial sequence
<220> FEATURE:
<223> OTHER INFORMATION: Reverse primer R5 for chimeric gene HIV subtype
      B gp120 C1-C5-gp41

<400> SEQUENCE: 70 attttttctcg agccaggtca tgttgtccca gatttcgtcc agggaac           47

<210> SEQ ID NO 71
<211> LENGTH: 45
<212> TYPE: DNA
<213> ORGANISM: Artificial sequence
<220> FEATURE:
<223> OTHER INFORMATION: Forward primer F1 for chimeric gene HIV subtype
      C gp120 C1-C5-gp41

<400> SEQUENCE: 71
gttgaacgtg aaaaacgtgg tggtggtggt ggtcagaccc gtgtt              45

<210> SEQ ID NO 72
<211> LENGTH: 45
<212> TYPE: DNA
<213> ORGANISM: Artificial sequence
<220> FEATURE:
<223> OTHER INFORMATION: Forward primer F2 for chimeric gene HIV subtype
      C gp120 C1-C5-gp41

<400> SEQUENCE: 72
gttgctccaa ccaaaccaaa acgtcgtgtt gttgaacgtg aaaaa              45

<210> SEQ ID NO 73
<211> LENGTH: 52
<212> TYPE: DNA
<213> ORGANISM: Artificial sequence
<220> FEATURE:
<223> OTHER INFORMATION: Forward primer F3 for chimeric gene HIV subtype
```

-continued

C gp120 C1-C5-gp41

<400> SEQUENCE: 73
aaaaaataca agttgttga aatcaaacca ctgggtgttg ctccaaccaa ac                52

<210> SEQ ID NO 74
<211> LENGTH: 51
<212> TYPE: DNA
<213> ORGANISM: Artificial sequence
<220> FEATURE:
<223> OTHER INFORMATION: Forward primer F4 for chimeric gene HIV subtype
      C gp120 C1-C5-gp41

<400> SEQUENCE: 74
ctgtgggtta ccgtttacta cggtgttcca gtgtggaaaa aatacaaagt t                51

<210> SEQ ID NO 75
<211> LENGTH: 45
<212> TYPE: DNA
<213> ORGANISM: Artificial sequence
<220> FEATURE:
<223> OTHER INFORMATION: Forward primer F5 for chimeric gene HIV subtype
      C gp120 C1-C5-gp41

<400> SEQUENCE: 75
cccgaattcc atatggtcga catgggtaac ctgtgggtta ccgtt 45

<210> SEQ ID NO 76
<211> LENGTH: 47
<212> TYPE: DNA
<213> ORGANISM: Artificial sequence
<220> FEATURE:
<223> OTHER INFORMATION: Reverse primer R1 for chimeric gene HIV subtype C gp120 C1-C5-gp41

<400> SEQUENCE: 76
tgctggtcac gcaggtgacg ttcgatagcc agaacacggg tctgacc 47

<210> SEQ ID NO 77
<211> LENGTH: 46
<212> TYPE: DNA
<213> ORGANISM: Artificial sequence
<220> FEATURE:
<223> OTHER INFORMATION: Reverse primer R2 for chimeric gene HIV subtype C gp120 C1-C5-gp41

<400> SEQUENCE: 77
tttaccggaa caaccccaga tacccagcag ctgctggtca cgcagg 46

<210> SEQ ID NO 78
<211> LENGTH: 46
<212> TYPE: DNA
<213> ORGANISM: Artificial sequence
<220> FEATURE:
<223> OTHER INFORMATION: Reverse primer R3 for chimeric gene HIV subtype C gp120 C1-C5-gp41

<400> SEQUENCE: 78
agttccatgg aacagcggtg gtacagatca gtttaccgga acaacc 46

<210> SEQ ID NO 79
<211> LENGTH: 48
<212> TYPE: DNA
<213> ORGANISM: Artificial sequence
<220> FEATURE:
<223> OTHER INFORMATION: Reverse primer R4 for chimeric gene HIV subtype C gp120 C1-C5-gp41

<400> SEQUENCE: 79
tttcttcctg ggatttgttg gaccaggagg agttccatgg aacagcgg 48

<210> SEQ ID NO 80
<211> LENGTH: 49
<212> TYPE: DNA
<213> ORGANISM: Artificial sequence
<220> FEATURE:
<223> OTHER INFORMATION: Reverse primer R5 for chimeric gene HIV subtype C gp120 C1-C5-gp41

<400> SEQUENCE: 80
atttttctcg agccaggtca tgttgtccca gatttcttcc tgggatttg 49

<210> SEQ ID NO 81
<211> LENGTH: 45
<212> TYPE: DNA
<213> ORGANISM: Artificial sequence
<220> FEATURE:
<223> OTHER INFORMATION: Forward primer F1 for chimeric gene HIV subtype D gp120 C1-C5-gp41

<400> SEQUENCE: 81
gttgaacgtg aaaaacgtgg tggtggtggt ggtcaggctc gtatt 45

<210> SEQ ID NO 82
<211> LENGTH: 45
<212> TYPE: DNA
<213> ORGANISM: Artificial sequence
<220> FEATURE:
<223> OTHER INFORMATION: Forward primer F2 for chimeric gene HIV subtype D gp120 C1-C5-gp41

<400> SEQUENCE: 82
gttgctccaa cccgtgctaa acgtcgtgtt gttgaacgtg aaaaa 45

<210> SEQ ID NO 83
<211> LENGTH: 49
<212> TYPE: DNA
<213> ORGANISM: Artificial sequence
<220> FEATURE:
<223> OTHER INFORMATION: Forward primer F3 for chimeric gene HIV subtype D gp120 C1-C5-gp41

<400> SEQUENCE: 83
gtggaaaaaa gttgttcaga tcgaaccact gggtgttgct ccaacccgt 49

<210> SEQ ID NO 84
<211> LENGTH: 46
<212> TYPE: DNA
<213> ORGANISM: Artificial sequence
<220> FEATURE:
<223> OTHER INFORMATION: Forward primer F4 for chimeric gene HIV subtype D gp120 C1-C5-gp41

<400> SEQUENCE: 84
gtgggttacc gtttactacg gtgttccagt gtggaaaaaa gttgtt 46

<210> SEQ ID NO 85
<211> LENGTH: 47
<212> TYPE: DNA
<213> ORGANISM: Artificial sequence
<220> FEATURE:
<223> OTHER INFORMATION: Forward primer F5 for chimeric gene HIV subtype D gp120 C1-C5-gp41

<400> SEQUENCE: 85

-continued

```
cccgaattcc atatggtcga cgctgacaac ctgtgggtta ccgttta                47

<210> SEQ ID NO 86
<211> LENGTH: 47
<212> TYPE: DNA
<213> ORGANISM: Artificial sequence
<220> FEATURE:
<223> OTHER INFORMATION: Reverse primer R1 for chimeric gene HIV subtype
      D gp120 C1-C5-gp41

<400> SEQUENCE: 86
tgctggtctt tcaggtaacg ttcaacagcc agaatacgag cctgacc                47

<210> SEQ ID NO 87
<211> LENGTH: 46
<212> TYPE: DNA
<213> ORGANISM: Artificial sequence
<220> FEATURE:
<223> OTHER INFORMATION: Reverse primer R2 for chimeric gene HIV subtype
      D gp120 C1-C5-gp41

<400> SEQUENCE: 87
tttaccggaa caaccccaga tacccagcag ctgctggtct ttcagg                 46

<210> SEQ ID NO 88
<211> LENGTH: 46
<212> TYPE: DNA
<213> ORGANISM: Artificial sequence
<220> FEATURE:
<223> OTHER INFORMATION: Reverse primer R3 for chimeric gene HIV subtype
      D gp120 C1-C5-gp41

<400> SEQUENCE: 88
agttccatgg aacgttggtg gtacagatgt gtttaccgga acaacc                 46

<210> SEQ ID NO 89
<211> LENGTH: 48
<212> TYPE: DNA
<213> ORGANISM: Artificial sequence
<220> FEATURE:
<223> OTHER INFORMATION: Reverse primer R4 for chimeric gene HIV subtype
      D gp120 C1-C5-gp41

<400> SEQUENCE: 89
tttcgttcag ggaacggttg gaccaggagg agttccatgg aacgttgg               48

<210> SEQ ID NO 90
<211> LENGTH: 49
<212> TYPE: DNA
<213> ORGANISM: Artificial sequence
<220> FEATURE:
<223> OTHER INFORMATION: Reverse primer R5 for chimeric gene HIV subtype
      D gp120 C1-C5-gp41

<400> SEQUENCE: 90
atttttctcg agccaggtca tgttctgcca gatttcgttc agggaacgg              49

<210> SEQ ID NO 91
<211> LENGTH: 45
<212> TYPE: DNA
<213> ORGANISM: Artificial sequence
<220> FEATURE:
<223> OTHER INFORMATION: Forward primer F1 for chimeric gene HIV subtype
      E gp120 C1-C5-gp41

<400> SEQUENCE: 91
gttgaacgtg aaaaacgtgg tggtggtggt ggtcaggctc gtgtt                  45
```

<210> SEQ ID NO 92
<211> LENGTH: 46
<212> TYPE: DNA
<213> ORGANISM: Artificial sequence
<220> FEATURE:
<223> OTHER INFORMATION: Forward primer F2 for chimeric gene HIV subtype
     E gp120 C1-C5-gp41

<400> SEQUENCE: 92
atcgctccaa cccgtccaaa acgtcgtgtt gttgaacgtg aaaaac          46

<210> SEQ ID NO 93
<211> LENGTH: 49
<212> TYPE: DNA
<213> ORGANISM: Artificial sequence
<220> FEATURE:
<223> OTHER INFORMATION: Forward primer F3 for chimeric gene HIV subtype
     E gp120 C1-C5-gp41

<400> SEQUENCE: 93
gtggcgtaaa gttgttcaga tcgaaccact gggtatcgct ccaacccgt 49

<210> SEQ ID NO 94
<211> LENGTH: 46
<212> TYPE: DNA
<213> ORGANISM: Artificial sequence
<220> FEATURE:
<223> OTHER INFORMATION: Forward primer F4 for chimeric gene HIV subtype
E gp120 C1-C5-gp41

<400> SEQUENCE: 94
gtgggttacc gtttactacg gtgttccagt gtggcgtaaa gttgtt 46

<210> SEQ ID NO 95
<211> LENGTH: 44
<212> TYPE: DNA
<213> ORGANISM: Artificial sequence
<220> FEATURE:
<223> OTHER INFORMATION: Forward primer F5 for chimeric gene HIV subtype
E gp120 C1-C5-gp41

<400> SEQUENCE: 95
cccgaattcc atatggtcga ctccaacctg tgggttaccg ttta 44

<210> SEQ ID NO 96
<211> LENGTH: 48
<212> TYPE: DNA
<213> ORGANISM: Artificial sequence
<220> FEATURE:
<223> OTHER INFORMATION: Reverse primer R1 for chimeric gene HIV subtype
E gp120 C1-C5-gp41

<400> SEQUENCE: 96
tttctggtct ttcaggtaac gttcaacagc cagaacacga gcctgacc 48

<210> SEQ ID NO 97
<211> LENGTH: 46
<212> TYPE: DNA
<213> ORGANISM: Artificial sequence
<220> FEATURE:
<223> OTHER INFORMATION: Reverse primer R2 for chimeric gene HIV subtype
E gp120 C1-C5-gp41

<400> SEQUENCE: 97
tttaccggaa caaccccaca gacccaggaa tttctggtct ttcagg 46

<210> SEQ ID NO 98

<211> LENGTH: 46
<212> TYPE: DNA
<213> ORGANISM: Artificial sequence
<220> FEATURE:
<223> OTHER INFORMATION: Reverse primer R3 for chimeric gene HIV subtype
      E gp120 C1-C5-gp41

<400> SEQUENCE: 98
agttccatgg aacagcggtg gtacagatga ttttaccgga acaacc          46

<210> SEQ ID NO 99
<211> LENGTH: 48
<212> TYPE: DNA
<213> ORGANISM: Artificial sequence
<220> FEATURE:
<223> OTHER INFORMATION: Reverse primer R4 for chimeric gene HIV subtype
      E gp120 C1-C5-gp41

<400> SEQUENCE: 99
tttcttcgaa ggaacggttg gaccaggagg agttccatgg aacagcgg          48

<210> SEQ ID NO 100
<211> LENGTH: 49
<212> TYPE: DNA
<213> ORGANISM: Artificial sequence
<220> FEATURE:
<223> OTHER INFORMATION: Reverse primer R5 for chimeric gene HIV subtype
      E gp120 C1-C5-gp41

<400> SEQUENCE: 100
atttttctcg agccaggtca tgttgttcca gatttcttcg aaggaacgg 49

<210> SEQ ID NO 101
<211> LENGTH: 45
<212> TYPE: DNA
<213> ORGANISM: Artificial sequence
<220> FEATURE:
<223> OTHER INFORMATION: Forward primer F1 for chimeric gene HIV subtype F gp120 C1-C5-gp41

<400> SEQUENCE: 101
gttcagcgtg aaaaacgtgg tggtggtggt ggtcaggctc gtgtt 45

<210> SEQ ID NO 102
<211> LENGTH: 45
<212> TYPE: DNA
<213> ORGANISM: Artificial sequence
<220> FEATURE:
<223> OTHER INFORMATION: Forward primer F2 for chimeric gene HIV subtype F gp120 C1-C5-gp41

<400> SEQUENCE: 102
gttgctccaa ccaaagctaa acgtcaggtt gttcagcgtg aaaaa 45

<210> SEQ ID NO 103
<211> LENGTH: 49
<212> TYPE: DNA
<213> ORGANISM: Artificial sequence
<220> FEATURE:
<223> OTHER INFORMATION: Forward primer F3 for chimeric gene HIV subtype F gp120 C1-C5-gp41

<400> SEQUENCE: 103
gtggaaaaaa gttgttgaaa tcgaaccact gggtgttgct ccaaccaaa 49

<210> SEQ ID NO 104
<211> LENGTH: 46
<212> TYPE: DNA

<213> ORGANISM: Artificial sequence
<220> FEATURE:
<223> OTHER INFORMATION: Forward primer F4 for chimeric gene HIV subtype F gp120 C1-C5-gp41

<400> SEQUENCE: 104
gtgggttacc gtttactacg gtgttccagt gtggaaaaaa gttgtt 46

<210> SEQ ID NO 105
<211> LENGTH: 47
<212> TYPE: DNA
<213> ORGANISM: Artificial sequence
<220> FEATURE:
<223> OTHER INFORMATION: Forward primer F5 for chimeric gene HIV subtype F gp120 C1-C5-gp41

<400> SEQUENCE: 105
cccgaattcc atatggtcga cgctgacaac ctgtgggtta ccgttta 47

<210> SEQ ID NO 106
<211> LENGTH: 47
<212> TYPE: DNA
<213> ORGANISM: Artificial sequence
<220> FEATURE:
<223> OTHER INFORMATION: Reverse primer R1 for chimeric gene HIV subtype F gp120 C1-C5-gp41

<400> SEQUENCE: 106
tgctggtctt tcaggtaacg ttcaacagcc agaacacgag cctgacc 47

<210> SEQ ID NO 107
<211> LENGTH: 46
<212> TYPE: DNA
<213> ORGANISM: Artificial sequence
<220> FEATURE:
<223> OTHER INFORMATION: Reverse primer R2 for chimeric gene HIV subtype F gp120 C1-C5-gp41

<400> SEQUENCE: 107
tttaccggaa caaccccaga tacccagcag ctgctggtct ttcagg 46

<210> SEQ ID NO 108
<211> LENGTH: 46
<212> TYPE: DNA
<213> ORGANISM: Artificial sequence
<220> FEATURE:
<223> OTHER INFORMATION: Reverse primer R3 for chimeric gene HIV subtype F gp120 C1-C5-gp41

<400> SEQUENCE: 108
agttccatgg aacgttggtg gtacagatca gtttaccgga acaacc 46

<210> SEQ ID NO 109
<211> LENGTH: 48
<212> TYPE: DNA
<213> ORGANISM: Artificial sequence
<220> FEATURE:
<223> OTHER INFORMATION: Reverse primer R4 for chimeric gene HIV subtype F gp120 C1-C5-gp41

<400> SEQUENCE: 109
tttcttcctg ggatttgttg gaccaggagg agttccatgg aacgttgg 48

<210> SEQ ID NO 110
<211> LENGTH: 49
<212> TYPE: DNA
<213> ORGANISM: Artificial sequence
<220> FEATURE:

<223> OTHER INFORMATION: Reverse primer R5 for chimeric gene HIV subtype
     F gp120 C1-C5-gp41

<400> SEQUENCE: 110
atttttctcg agccaggtca tgttgttcca gatttcttcc tgggatttg         49

<210> SEQ ID NO 111
<211> LENGTH: 45
<212> TYPE: DNA
<213> ORGANISM: Artificial sequence
<220> FEATURE:
<223> OTHER INFORMATION: Forward primer F1 for chimeric gene HIV subtype
     G gp120 C1-C5-gp41

<400> SEQUENCE: 111
gttggtcgtg aaaaacgtgg tggtggtggt ggtcaggctc gtgtt             45

<210> SEQ ID NO 112
<211> LENGTH: 45
<212> TYPE: DNA
<213> ORGANISM: Artificial sequence
<220> FEATURE:
<223> OTHER INFORMATION: Forward primer F2 for chimeric gene HIV subtype
     G gp120 C1-C5-gp41

<400> SEQUENCE: 112
gttgctccaa ccaaagctcg tcgtcgtgtt gttggtcgtg aaaaa             45

<210> SEQ ID NO 113
<211> LENGTH: 51
<212> TYPE: DNA
<213> ORGANISM: Artificial sequence
<220> FEATURE:
<223> OTHER INFORMATION: Forward primer F3 for chimeric gene HIV subtype
     G gp120 C1-C5-gp41

<400> SEQUENCE: 113
gacgctaaaa aagttgttaa aatcaaacca ctgggtgttg ctccaaccaa a       51

<210> SEQ ID NO 114
<211> LENGTH: 52
<212> TYPE: DNA
<213> ORGANISM: Artificial sequence
<220> FEATURE:
<223> OTHER INFORMATION: Forward primer F4 for chimeric gene HIV subtype
     G gp120 C1-C5-gp41

<400> SEQUENCE: 114
gtgggttacc gtttactacg gtgttccagt gtgggaagac gctaaaaaag tt      52

<210> SEQ ID NO 115
<211> LENGTH: 50
<212> TYPE: DNA
<213> ORGANISM: Artificial sequence
<220> FEATURE:
<223> OTHER INFORMATION: Forward primer F5 for chimeric gene HIV subtype
     G gp120 C1-C5-gp41

<400> SEQUENCE: 115
cccgaattcc atatggtcga cgcttccaac aacctgtggg ttaccgttta         50

<210> SEQ ID NO 116
<211> LENGTH: 47
<212> TYPE: DNA
<213> ORGANISM: Artificial sequence
<220> FEATURE:
<223> OTHER INFORMATION: Reverse primer R1 for chimeric gene HIV subtype
     G gp120 C1-C5-gp41

<400> SEQUENCE: 116
tgctggtcac gcaggtaacg ttccagagcc agaacacgag cctgacc         47

<210> SEQ ID NO 117
<211> LENGTH: 46
<212> TYPE: DNA
<213> ORGANISM: Artificial sequence
<220> FEATURE:
<223> OTHER INFORMATION: Reverse primer R2 for chimeric gene HIV subtype
      G gp120 C1-C5-gp41

<400> SEQUENCE: 117
tttaccggaa caaccccaga tacccagcag ctgctggtca cgcagg           46

<210> SEQ ID NO 118
<211> LENGTH: 48
<212> TYPE: DNA
<213> ORGANISM: Artificial sequence
<220> FEATURE:
<223> OTHER INFORMATION: Reverse primer R3 for chimeric gene HIV subtype
      G gp120 C1-C5-gp41

<400> SEQUENCE: 118
agcgttccat ggaacgttgg tggtacagat cagtttaccg gaacaacc 48

<210> SEQ ID NO 119
<211> LENGTH: 44
<212> TYPE: DNA
<213> ORGANISM: Artificial sequence
<220> FEATURE:
<223> OTHER INFORMATION: Reverse primer R4 for chimeric gene HIV subtype G gp120 C1-C5-gp41

<400> SEQUENCE: 119
atgtcgttgt aggttttgtt ggaccaggaa gcgttccatg gaac 44

<210> SEQ ID NO 120
<211> LENGTH: 46
<212> TYPE: DNA
<213> ORGANISM: Artificial sequence
<220> FEATURE:
<223> OTHER INFORMATION: Reverse primer R5 for chimeric gene HIV subtype G gp120 C1-C5-gp41

<400> SEQUENCE: 120
tttctcgagc caggtcatgt tgtcccagat gtcgttgtag gttttg 46

<210> SEQ ID NO 121
<211> LENGTH: 45
<212> TYPE: DNA
<213> ORGANISM: Artificial sequence
<220> FEATURE:
<223> OTHER INFORMATION: Forward primer F1 for chimeric gene HIV subtype H gp120 C1-C5-gp41

<400> SEQUENCE: 121
gttgaacgtg aaaaacgtgg tggtggtggt ggtcaggctc gtgtt 45

<210> SEQ ID NO 122
<211> LENGTH: 45
<212> TYPE: DNA
<213> ORGANISM: Artificial sequence
<220> FEATURE:
<223> OTHER INFORMATION: Forward primer F2 for chimeric gene HIV subtype H gp120 C1-C5-gp41

<400> SEQUENCE: 122

```
<210> SEQ ID NO 123
<211> LENGTH: 49
<212> TYPE: DNA
<213> ORGANISM: Artificial sequence
<220> FEATURE:
<223> OTHER INFORMATION: Forward primer F3 for chimeric gene HIV subtype
      H gp120 C1-C5-gp41

<400> SEQUENCE: 123
gtggaaaaaa gttgttaaaa tcgaaccact gggtgttgct ccaaccgaa          49

<210> SEQ ID NO 124
<211> LENGTH: 48
<212> TYPE: DNA
<213> ORGANISM: Artificial sequence
<220> FEATURE:
<223> OTHER INFORMATION: Forward primer F4 for chimeric gene HIV subtype
      H gp120 C1-C5-gp41

<400> SEQUENCE: 124
ctgtgggtta ccgtttacta cggtgttcca gtgtggaaaa aagttgtt            48

<210> SEQ ID NO 125
<211> LENGTH: 48
<212> TYPE: DNA
<213> ORGANISM: Artificial sequence
<220> FEATURE:
<223> OTHER INFORMATION: Forward primer F5 for chimeric gene HIV subtype
      H gp120 C1-C5-gp41

<400> SEQUENCE: 125
cccgaattcc atatggtcga cgttgttggt aacctgtggg ttaccgtt            48

<210> SEQ ID NO 126
<211> LENGTH: 47
<212> TYPE: DNA
<213> ORGANISM: Artificial sequence
<220> FEATURE:
<223> OTHER INFORMATION: Reverse primer R1 for chimeric gene HIV subtype
      H gp120 C1-C5-gp41

<400> SEQUENCE: 126
tgctggtctt tcaggtaacg ttcaacagcc agaacacgag cctgacc             47

<210> SEQ ID NO 127
<211> LENGTH: 46
<212> TYPE: DNA
<213> ORGANISM: Artificial sequence
<220> FEATURE:
<223> OTHER INFORMATION: Reverse primer R2 for chimeric gene HIV subtype
      H gp120 C1-C5-gp41

<400> SEQUENCE: 127
tttaccggaa caaccccaga tacccagcag ctgctggtct ttcagg              46

<210> SEQ ID NO 128
<211> LENGTH: 46
<212> TYPE: DNA
<213> ORGANISM: Artificial sequence
<220> FEATURE:
<223> OTHER INFORMATION: Reverse primer R3 for chimeric gene HIV subtype
      H gp120 C1-C5-gp41

<400> SEQUENCE: 128
agttccatgg aacgttggtg gtacagatca gtttaccgga acaacc              46
```

(gttgctccaa ccgaagctcg tcgtcgtgtt gttgaacgtg aaaaa    45)

<210> SEQ ID NO 129
<211> LENGTH: 48
<212> TYPE: DNA
<213> ORGANISM: Artificial sequence
<220> FEATURE:
<223> OTHER INFORMATION: Reverse primer R4 for chimeric gene HIV subtype
      H gp120 C1-C5-gp41

<400> SEQUENCE: 129
tttcgtccag ggatttgttg gaccaggagg agttccatgg aacgttgg 48

<210> SEQ ID NO 130
<211> LENGTH: 55
<212> TYPE: DNA
<213> ORGANISM: Artificial sequence
<220> FEATURE:
<223> OTHER INFORMATION: Reverse primer R5 for chimeric gene HIV subtype H gp120 C1-C5-gp41

<400> SEQUENCE: 130
tttctcgagc cattccatcc aggtcatgtt gtcccagatt tcgtccaggg atttg 55

<210> SEQ ID NO 131
<211> LENGTH: 45
<212> TYPE: DNA
<213> ORGANISM: Artificial sequence
<220> FEATURE:
<223> OTHER INFORMATION: Forward primer F1 for chimeric gene HIV subtype J gp120 C1-C5-gp41

<400> SEQUENCE: 131
gttgaacgtg aaaaacgtgg tggtggtggt ggtcaggctc gtgtt 45

<210> SEQ ID NO 132
<211> LENGTH: 45
<212> TYPE: DNA
<213> ORGANISM: Artificial sequence
<220> FEATURE:
<223> OTHER INFORMATION: Forward primer F2 for chimeric gene HIV subtype J gp120 C1-C5-gp41

<400> SEQUENCE: 132
gttgctccaa ccaaagctaa acgtcgtgtt gttgaacgtg aaaaa 45

<210> SEQ ID NO 133
<211> LENGTH: 49
<212> TYPE: DNA
<213> ORGANISM: Artificial sequence
<220> FEATURE:
<223> OTHER INFORMATION: Forward primer F3 for chimeric gene HIV subtype J gp120 C1-C5-gp41

<400> SEQUENCE: 133
gtggaaaaaa gttgttgaaa tcgaaccact gggtgttgct ccaaccaaa 49

<210> SEQ ID NO 134
<211> LENGTH: 48
<212> TYPE: DNA
<213> ORGANISM: Artificial sequence
<220> FEATURE:
<223> OTHER INFORMATION: Forward primer F4 for chimeric gene HIV subtype J gp120 C1-C5-gp41

<400> SEQUENCE: 134
ctgtgggtta ccgtttacta cggtgttcca gtgtggaaaa aagttgtt 48

<210> SEQ ID NO 135
<211> LENGTH: 48
<212> TYPE: DNA
<213> ORGANISM: Artificial sequence
<220> FEATURE:
<223> OTHER INFORMATION: Forward primer F5 for chimeric gene HIV subtype
       J gp120 C1-C5-gp41

<400> SEQUENCE: 135
cccgaattcc atatggtcga cgctaaagaa gacctgtggg ttaccgtt                    48

<210> SEQ ID NO 136
<211> LENGTH: 47
<212> TYPE: DNA
<213> ORGANISM: Artificial sequence
<220> FEATURE:
<223> OTHER INFORMATION: Reverse primer R1 for chimeric gene HIV subtype
       J gp120 C1-C5-gp41

<400> SEQUENCE: 136
tgctggtctt tcaggtaacg ttcaacagcc agaacacgag cctgacc                     47

<210> SEQ ID NO 137
<211> LENGTH: 46
<212> TYPE: DNA
<213> ORGANISM: Artificial sequence
<220> FEATURE:
<223> OTHER INFORMATION: Reverse primer R2 for chimeric gene HIV subtype
       J gp120 C1-C5-gp41

<400> SEQUENCE: 137
tttaccggaa caaccccaga tacccagcag ctgctggtct ttcagg                      46

<210> SEQ ID NO 138
<211> LENGTH: 48
<212> TYPE: DNA
<213> ORGANISM: Artificial sequence
<220> FEATURE:
<223> OTHER INFORMATION: Reverse primer R3 for chimeric gene HIV subtype
       J gp120 C1-C5-gp41

<400> SEQUENCE: 138
agcgttccat ggaacgttgg tggtacagat cagtttaccg gaacaacc                    48

<210> SEQ ID NO 139
<211> LENGTH: 44
<212> TYPE: DNA
<213> ORGANISM: Artificial sequence
<220> FEATURE:
<223> OTHER INFORMATION: Reverse primer R4 for chimeric gene HIV subtype
       J gp120 C1-C5-gp41

<400> SEQUENCE: 139
atgtcttcgt aggatttgtt ggaccaggaa gcgttccatg gaac                        44

<210> SEQ ID NO 140
<211> LENGTH: 46
<212> TYPE: DNA
<213> ORGANISM: Artificial sequence
<220> FEATURE:
<223> OTHER INFORMATION: Reverse primer R5 for chimeric gene HIV subtype
       J gp120 C1-C5-gp41

<400> SEQUENCE: 140
tttctcgagc caggtcatgt tttcccagat gtcttcgtag gatttg                      46

<210> SEQ ID NO 141
<211> LENGTH: 45

```
<212> TYPE: DNA
<213> ORGANISM: Artificial sequence
<220> FEATURE:
<223> OTHER INFORMATION: Forward primer F1 for chimeric gene HIV subtype
      K gp120 C1-C5-gp41

<400> SEQUENCE: 141
gttcagcgtg aaaaacgtgg tggtggtggt ggtcgtgctc gtgtt                    45

<210> SEQ ID NO 142
<211> LENGTH: 46
<212> TYPE: DNA
<213> ORGANISM: Artificial sequence
<220> FEATURE:
<223> OTHER INFORMATION: Forward primer F2 for chimeric gene HIV subtype
      K gp120 C1-C5-gp41

<400> SEQUENCE: 142
atcgctccaa cccgtgctcg tcgtcgtgtt gttcagcgtg aaaaac                   46

<210> SEQ ID NO 143
<211> LENGTH: 49
<212> TYPE: DNA
<213> ORGANISM: Artificial sequence
<220> FEATURE:
<223> OTHER INFORMATION: Forward primer F3 for chimeric gene HIV subtype
      K gp120 C1-C5-gp41

<400> SEQUENCE: 143
gtggaaaaaa gttgttcaga tcgaaccact gggtatcgct ccaacccgt                49

<210> SEQ ID NO 144
<211> LENGTH: 48
<212> TYPE: DNA
<213> ORGANISM: Artificial sequence
<220> FEATURE:
<223> OTHER INFORMATION: Forward primer F4 for chimeric gene HIV subtype
      K gp120 C1-C5-gp41

<400> SEQUENCE: 144
ctgtgggtta ccgtttacta cggtgttcca gtgtggaaaa aagttgtt                 48

<210> SEQ ID NO 145
<211> LENGTH: 48
<212> TYPE: DNA
<213> ORGANISM: Artificial sequence
<220> FEATURE:
<223> OTHER INFORMATION: Forward primer F5 for chimeric gene HIV subtype
      K gp120 C1-C5-gp41

<400> SEQUENCE: 145
cccgaattcc atatggtcga cgctgctaac aacctgtggg ttaccgtt                 48

<210> SEQ ID NO 146
<211> LENGTH: 47
<212> TYPE: DNA
<213> ORGANISM: Artificial sequence
<220> FEATURE:
<223> OTHER INFORMATION: Reverse primer R1 for chimeric gene HIV subtype
      K gp120 C1-C5-gp41

<400> SEQUENCE: 146
tgctggtcac gcaggtaacg ttcaacagcc agaacacgag cacgacc                  47

<210> SEQ ID NO 147
<211> LENGTH: 46
<212> TYPE: DNA
<213> ORGANISM: Artificial sequence
```

-continued

<220> FEATURE:
<223> OTHER INFORMATION: Reverse primer R2 for chimeric gene HIV subtype
K gp120 C1-C5-gp41

<400> SEQUENCE: 147
tttaccggaa caacccaga tacccagcag ctgctggtca cgcagg         46

<210> SEQ ID NO 148
<211> LENGTH: 46
<212> TYPE: DNA
<213> ORGANISM: Artificial sequence
<220> FEATURE:
<223> OTHER INFORMATION: Reverse primer R3 for chimeric gene HIV subtype
K gp120 C1-C5-gp41

<400> SEQUENCE: 148
agttccatgg aacgttggtg gtacagatca gtttaccgga acaacc         46

<210> SEQ ID NO 149
<211> LENGTH: 48
<212> TYPE: DNA
<213> ORGANISM: Artificial sequence
<220> FEATURE:
<223> OTHER INFORMATION: Reverse primer R4 for chimeric gene HIV subtype
K gp120 C1-C5-gp41

<400> SEQUENCE: 149
tttcggactg ggatttgttg gaccaggagg agttccatgg aacgttgg         48

<210> SEQ ID NO 150
<211> LENGTH: 46
<212> TYPE: DNA
<213> ORGANISM: Artificial sequence
<220> FEATURE:
<223> OTHER INFORMATION: Reverse primer R5 for chimeric gene HIV subtype
K gp120 C1-C5-gp41

<400> SEQUENCE: 150
tttctcgagc caggtcatgt tttcccagat tcggactgg gatttg         46

<210> SEQ ID NO 151
<211> LENGTH: 71
<212> TYPE: PRT
<213> ORGANISM: Human immunodeficiency virus

<400> SEQUENCE: 151

Val Asp Arg Asp Glu Leu Lys Gly Ile Gly Met Thr Asn Asn Pro Pro
1               5                   10                  15

Ile Pro Val Gly Glu Ile Tyr Lys Arg Trp Ile Ile Leu Gly Leu Asn
            20                  25                  30

Lys Ile Val Arg Met Tyr Ser Pro Thr Met Thr Asn Asn Pro Pro Ile
        35                  40                  45

Pro Val Gly Glu Ile Tyr Arg Trp Ile Ile Leu Gly Leu Asn Lys Ile
    50                  55                  60

Val Arg Met Tyr Ser Pro Thr
65                  70

<210> SEQ ID NO 152
<211> LENGTH: 132
<212> TYPE: PRT
<213> ORGANISM: Human immunodeficiency virus

<400> SEQUENCE: 152

Pro Thr Val Arg Gln Arg Met Asp Arg Thr Glu Pro Ala Ala Glu Gly
1               5                   10                  15

Val Gly Ala Val Ser Arg Asp Leu Glu Lys His Gly Ala Ile Thr Ser
            20                  25                  30

Ser Asn Thr Ala Ala Thr Asn Ala Asp Cys Ala Trp Leu Glu Ala Gln
        35                  40                  45

Glu Glu Glu Val Gly Phe Pro Val Arg Pro Gln Val Pro Leu Arg
    50                  55                  60

Pro Met Thr Tyr Lys Ala Ala Val Asp Ile Ser His Phe Leu Lys Glu
65                  70                  75                  80

Lys Gly Gly Leu Glu Gly Leu Ile Tyr Ser Gln Lys Arg Gln Glu Ile
                85                  90                  95

Leu Asp Leu Trp Ile Tyr His Thr Gln Gly Tyr Phe Pro Asp Trp Gln
            100                 105                 110

Asn Tyr Thr Pro Gly Pro Gly Ile Arg Tyr Pro Leu Thr Phe Gly Trp
        115                 120                 125

Cys Phe Lys Leu
    130

<210> SEQ ID NO 153
<211> LENGTH: 66
<212> TYPE: PRT
<213> ORGANISM: Human immunodeficiency virus

<400> SEQUENCE: 153

Phe Leu Lys Val Pro Val Asp Pro Glu Gln Val Glu Lys Ala Asn Glu
1               5                   10                  15

Gly Asp Asn Asn Cys Leu Leu His Pro Ile Ser Gln His Gly Met Asp
            20                  25                  30

Asp Pro Glu Lys Glu Val Leu Met Trp Lys Phe Asp Ser Arg Leu Ala
        35                  40                  45

Phe Gln His Ile Ala Arg Glu Lys His Pro Glu Tyr Tyr Lys Asp Cys
    50                  55                  60

Leu Gly
65

<210> SEQ ID NO 154
<211> LENGTH: 109
<212> TYPE: PRT
<213> ORGANISM: Human immunodeficiency virus

<400> SEQUENCE: 154

Arg Asp Glu Leu Lys Gly Ile Gly Met Glu Pro Val Asp Pro Arg Leu
1               5                   10                  15

Glu Pro Trp Lys His Pro Gly Ser Gln Pro Arg Thr Ala Cys Asn Asn
            20                  25                  30

Cys Tyr Cys Lys Lys Cys Cys Phe His Cys Pro Val Cys Phe Ile Ser
        35                  40                  45

Lys Gly Leu Gly Ile Ser Tyr Gly Arg Lys Lys Arg Arg Gln Arg Arg
    50                  55                  60

Arg Ala Pro Gln Asp Ser Glu Thr His Gln Val Ser Leu Ser Lys Gln
65                  70                  75                  80

Pro Thr Ser Gln Leu Arg Gly Asp Pro Thr Gly Pro Lys Glu Ser Lys
                85                  90                  95

Lys Lys Val Glu Arg Glu Thr Glu Thr Asp Pro Asn Val
            100                 105

<210> SEQ ID NO 155
<211> LENGTH: 88

<212> TYPE: PRT
<213> ORGANISM: Human immunodeficiency virus

<400> SEQUENCE: 155

```
Leu Leu Ala Val Arg Ile Ile Lys Thr Leu Tyr Gln Ser Asn Pro Tyr
1               5                   10                  15

Pro Lys Pro Glu Gly Tyr Arg Arg Val Arg Arg Asn Arg Arg Arg Arg
            20                  25                  30

Trp Arg Ala Arg Gln Arg Gln Ile His Ser Ile Ser Glu Arg Ile Leu
        35                  40                  45

Ile Thr Cys Leu Gly Arg Pro Thr Glu Pro Val Pro Leu Gln Leu Pro
    50                  55                  60

Pro Ile Glu Arg Leu Asn Ile Asn Cys Ser Glu Ser Gly Gly Thr Ser
65                  70                  75                  80

Gly Thr Gln Arg Val Gly Asn Pro
                85
```

<210> SEQ ID NO 156
<211> LENGTH: 207
<212> TYPE: DNA
<213> ORGANISM: Human immunodeficiency virus

<400> SEQUENCE: 156

```
cgtgacgaac tgaaaggtat cggtatgacc aacaacccgc cgatcccggt tggtgaaatc     60
tacaaacgtt ggatcatcct gggtctgaac aaaatcgttc gtatgtacag cccgaccatg    120
accaacaacc cgccaattcc agtaggcgag atttaccgtt ggatcatcct gggtctgaac    180
aaaatcgttc gcatgtacag cccgact                                        207
```

<210> SEQ ID NO 157
<211> LENGTH: 396
<212> TYPE: DNA
<213> ORGANISM: Human immunodeficiency virus

<400> SEQUENCE: 157

```
ccgaccgttc gtcagcgtat ggaccgtacc gaaccggctg ctgagggtgt tggtgctgtt     60
agccgtgacc tggaaaaaca cggtgctatc acctcttcta acaccgctgc taccaacgct    120
gactgcgctt ggctggaagc tcaggaagaa gaagaagttg gttttccggt tcgtccgcag    180
gttccgctgc gtccgatgac ctacaaagct gctgttgaca tcagccactt cctgaaagaa    240
aaaggcggcc tggaaggtct gatctacagc cagaaacgtc aggaaatcct ggacctgtgg    300
atctaccaca cccagggcta cttcccggac tggcagaact acaccccggg tccgggtatc    360
cgttacccgc tgaccttcgg ctggtgtttc aaactg                              396
```

<210> SEQ ID NO 158
<211> LENGTH: 198
<212> TYPE: DNA
<213> ORGANISM: Human immunodeficiency virus

<400> SEQUENCE: 158

```
ttcctgaaag ttccggttga cccggaacag gttgaaaaag ctaacgaagg tgataacaac     60
tgcctgctgc acccgatcag ccagcacggt atggacgacc cggaaaaaga agttctgatg    120
tggaaattcg acagccgtct ggctttccag cacatcgctc gtgaaaaaca cccggaatac    180
tacaaagact gcctgggt                                                  198
```

<210> SEQ ID NO 159
<211> LENGTH: 327

-continued

```
<212> TYPE: DNA
<213> ORGANISM: Human immunodeficiency virus

<400> SEQUENCE: 159
cgtgacgaac tgaaaggtat cggtatggaa ccggttgacc cgcgtctgga accgtggaaa      60
cacccgggta gccagccgcg taccgcttgc aacaactgct actgcaaaaa atgttgtttc     120
cactgcccgg tttgctttat ctctaaaggt ctgggtatca gctacggtcg taaaaagcgt     180
cgccagcgcc gccgcgctcc gcaggactcc gaaacccacc aggttagcct gagcaagcaa     240
ccgaccagcc agctgcgtgg tgacccgacc ggtccgaaag aaagcaaaaa aaaagttgaa     300
cgtgaaaccg aaaccgaccc gaacgtt                                          327

<210> SEQ ID NO 160
<211> LENGTH: 264
<212> TYPE: DNA
<213> ORGANISM: Human immunodeficiency virus

<400> SEQUENCE: 160
ctgctggctg ttcgtatcat caaaaccctg taccagtcta acccgtaccc gaaaccggaa      60
ggttaccgtc gtgtccgtcg taaccgccgc cgccgctggc gtgctcgtca gcgtcagatc     120
cactccatca gcgaacgtat cctgatcacc tgcctgggtc gtccgaccga accggttccg     180
ctgcaactgc cgccgatcga acgtctgaac atcaactgta gcgaaagcgg tggtaccagc     240
ggtacccagc gtgttggtaa cccg                                            264

<210> SEQ ID NO 161
<211> LENGTH: 39
<212> TYPE: DNA
<213> ORGANISM: Artificial sequence
<220> FEATURE:
<223> OTHER INFORMATION: Forward Primer F1 for gag24

<400> SEQUENCE: 161
tggatcatcc tgggtctgaa caaaatcgtt cgtatgtac                              39

<210> SEQ ID NO 162
<211> LENGTH: 39
<212> TYPE: DNA
<213> ORGANISM: Artificial sequence
<220> FEATURE:
<223> OTHER INFORMATION: Forward Primer F2 for gag24

<400> SEQUENCE: 162
ccggttggtg aaatctacaa acgttggatc atcctgggt                              39

<210> SEQ ID NO 163
<211> LENGTH: 41
<212> TYPE: DNA
<213> ORGANISM: Artificial sequence
<220> FEATURE:
<223> OTHER INFORMATION: Forward Primer F3 for gag24

<400> SEQUENCE: 163
tcggtatgac caacaacccg ccgatcccgg ttggtgaaat c                           41

<210> SEQ ID NO 164
<211> LENGTH: 56
<212> TYPE: DNA
<213> ORGANISM: Artificial sequence
<220> FEATURE:
<223> OTHER INFORMATION: Forward Primer F4 for gag24

<400> SEQUENCE: 164
```

```
cccgaattcc atatggtcga ccgtgacgaa ctgaaaggta tcggtatgac caacaa        56
```

<210> SEQ ID NO 165
<211> LENGTH: 39
<212> TYPE: DNA
<213> ORGANISM: Artificial sequence
<220> FEATURE:
<223> OTHER INFORMATION: Reverse Primer R1 for gag24

<400> SEQUENCE: 165

```
cgggttgttg gtcatggtcg ggctgtacat acgaacgat                          39
```

<210> SEQ ID NO 166
<211> LENGTH: 39
<212> TYPE: DNA
<213> ORGANISM: Artificial sequence
<220> FEATURE:
<223> OTHER INFORMATION: Reverse Primer R2 for gag24

<400> SEQUENCE: 166

```
gtaaatctcg cctactggaa ttggcgggtt gttgttcat                          39
```

<210> SEQ ID NO 167
<211> LENGTH: 40
<212> TYPE: DNA
<213> ORGANISM: Artificial sequence
<220> FEATURE:
<223> OTHER INFORMATION: Reverse Primer R3 for gag24

<400> SEQUENCE: 167

```
tgttcagacc caggatgatc caacggtaaa tctcgcctac                         40
```

<210> SEQ ID NO 168
<211> LENGTH: 69
<212> TYPE: DNA
<213> ORGANISM: Artificial sequence
<220> FEATURE:
<223> OTHER INFORMATION: Reverse Primer R4 for gag24

<400> SEQUENCE: 168

```
aaaaaaattc ccattatttt tctcgagagt cgggctgtac atgcgaacga ttttgttcag   60
acccaggat                                                           69
```

<210> SEQ ID NO 169
<211> LENGTH: 39
<212> TYPE: DNA
<213> ORGANISM: Artificial sequence
<220> FEATURE:
<223> OTHER INFORMATION: Forward Primer F1 for nef-N terminus

<400> SEQUENCE: 169

```
gcttggctgg aagctcagga agaagaagaa gttggtttt                          39
```

<210> SEQ ID NO 170
<211> LENGTH: 40
<212> TYPE: DNA
<213> ORGANISM: Artificial sequence
<220> FEATURE:
<223> OTHER INFORMATION: Forward Primer F2 for nef-N terminus

<400> SEQUENCE: 170

```
caccgctgct accaacgctg actgcgcttg gctggaagct                         40
```

<210> SEQ ID NO 171
<211> LENGTH: 42

```
<212> TYPE: DNA
<213> ORGANISM: Artificial sequence
<220> FEATURE:
<223> OTHER INFORMATION: Forward Primer F3 for nef-N terminus

<400> SEQUENCE: 171
aaacacggtg ctatcacctc ttctaacacc gctgctacca ac              42

<210> SEQ ID NO 172
<211> LENGTH: 40
<212> TYPE: DNA
<213> ORGANISM: Artificial sequence
<220> FEATURE:
<223> OTHER INFORMATION: Forward Primer F4 for nef-N terminus

<400> SEQUENCE: 172
tggtgctgtt agccgtgacc tggaaaaaca cggtgctatc                40

<210> SEQ ID NO 173
<211> LENGTH: 42
<212> TYPE: DNA
<213> ORGANISM: Artificial sequence
<220> FEATURE:
<223> OTHER INFORMATION: Forward Primer F5 for nef-N terminus

<400> SEQUENCE: 173
cgtaccgaac cggctgctga gggtgttggt gctgttagcc gt              42

<210> SEQ ID NO 174
<211> LENGTH: 40
<212> TYPE: DNA
<213> ORGANISM: Artificial sequence
<220> FEATURE:
<223> OTHER INFORMATION: Forward Primer F6 for nef-N terminus

<400> SEQUENCE: 174
gaccgttcgt cagcgtatgg accgtaccga accggctgct                40

<210> SEQ ID NO 175
<211> LENGTH: 44
<212> TYPE: DNA
<213> ORGANISM: Artificial sequence
<220> FEATURE:
<223> OTHER INFORMATION: Forward Primer F7 for nef-N terminus

<400> SEQUENCE: 175
cccgaattcc atatggtcga cccgaccgtt cgtcagcgta tgga            44

<210> SEQ ID NO 176
<211> LENGTH: 42
<212> TYPE: DNA
<213> ORGANISM: Artificial sequence
<220> FEATURE:
<223> OTHER INFORMATION: Reverser Primer R1 for nef-N terminus

<400> SEQUENCE: 176
acgcagcgga acctgcggac gaaccggaaa accaacttct tc              42

<210> SEQ ID NO 177
<211> LENGTH: 39
<212> TYPE: DNA
<213> ORGANISM: Artificial sequence
<220> FEATURE:
<223> OTHER INFORMATION: Reverser Primer R2 for nef-N terminus

<400> SEQUENCE: 177
aacagcagct ttgtaggtca tcggacgcag cggaacccg                  39
```

-continued

<210> SEQ ID NO 178
<211> LENGTH: 43
<212> TYPE: DNA
<213> ORGANISM: Artificial sequence
<220> FEATURE:
<223> OTHER INFORMATION: Reverser Primer R3 for nef-N terminus

<400> SEQUENCE: 178
cttttctttt caggaagtgg ctgatgtcaa cagcagcttt gta                43

<210> SEQ ID NO 179
<211> LENGTH: 39
<212> TYPE: DNA
<213> ORGANISM: Artificial sequence
<220> FEATURE:
<223> OTHER INFORMATION: Reverser Primer R4 for nef-N terminus

<400> SEQUENCE: 179
gtagatcaga ccttccaggc cgcctttttc tttcaggaa                    39

<210> SEQ ID NO 180
<211> LENGTH: 41
<212> TYPE: DNA
<213> ORGANISM: Artificial sequence
<220> FEATURE:
<223> OTHER INFORMATION: Reverser Primer R5 for nef-N terminus

<400> SEQUENCE: 180
tccaggattt cctgacgttt ctggctgtag atcagacctt c                 41

<210> SEQ ID NO 181
<211> LENGTH: 40
<212> TYPE: DNA
<213> ORGANISM: Artificial sequence
<220> FEATURE:
<223> OTHER INFORMATION: Reverser Primer R6 for nef-N terminus

<400> SEQUENCE: 181
agccctgggt gtggtagatc cacaggtcca ggatttcctg                   40

<210> SEQ ID NO 182
<211> LENGTH: 39
<212> TYPE: DNA
<213> ORGANISM: Artificial sequence
<220> FEATURE:
<223> OTHER INFORMATION: Reverser Primer R7 for nef-N terminus

<400> SEQUENCE: 182
gtagttctgc cagtccggga agtagccctg ggtgtggta                    39

<210> SEQ ID NO 183
<211> LENGTH: 44
<212> TYPE: DNA
<213> ORGANISM: Artificial sequence
<220> FEATURE:
<223> OTHER INFORMATION: Reverser Primer R8 for nef-N terminus

<400> SEQUENCE: 183
agcgggtaac ggatacccgg acccggggtg tagttctgcc agtc              44

<210> SEQ ID NO 184
<211> LENGTH: 66
<212> TYPE: DNA
<213> ORGANISM: Artificial sequence
<220> FEATURE:
<223> OTHER INFORMATION: Reverser Primer 9 for nef-N terminus

<400> SEQUENCE: 184
aaaaaaattc ccattatttt tctcgagcag tttgaaacac cagccgaagg tcagcgggta    60
acggat    66

<210> SEQ ID NO 185
<211> LENGTH: 39
<212> TYPE: DNA
<213> ORGANISM: Artificial sequence
<220> FEATURE:
<223> OTHER INFORMATION: Forward Primer F1 for nef-C terminus

<400> SEQUENCE: 185
ctgcacccga tcagccagca cggtatggac gacccggaa    39

<210> SEQ ID NO 186
<211> LENGTH: 39
<212> TYPE: DNA
<213> ORGANISM: Artificial sequence
<220> FEATURE:
<223> OTHER INFORMATION: Forward Primer F2 for nef-C terminus

<400> SEQUENCE: 186
aacgaaggtg ataacaactg cctgctgcac ccgatcagc    39

<210> SEQ ID NO 187
<211> LENGTH: 40
<212> TYPE: DNA
<213> ORGANISM: Artificial sequence
<220> FEATURE:
<223> OTHER INFORMATION: Forward Primer F3 for nef-C terminus

<400> SEQUENCE: 187
tgacccggaa caggttgaaa aagctaacga aggtgataac    40

<210> SEQ ID NO 188
<211> LENGTH: 54
<212> TYPE: DNA
<213> ORGANISM: Artificial sequence
<220> FEATURE:
<223> OTHER INFORMATION: Forward Primer F4 for nef-C terminus

<400> SEQUENCE: 188
cccgaattcc atatggtcga cttcctgaaa gttccggttg acccggaaca ggtt    54

<210> SEQ ID NO 189
<211> LENGTH: 39
<212> TYPE: DNA
<213> ORGANISM: Artificial sequence
<220> FEATURE:
<223> OTHER INFORMATION: Reverse Primer R1 for nef-C terminus

<400> SEQUENCE: 189
gaatttccac atcagaactt cttttttccgg gtcgtccat    39

<210> SEQ ID NO 190
<211> LENGTH: 40
<212> TYPE: DNA
<213> ORGANISM: Artificial sequence
<220> FEATURE:
<223> OTHER INFORMATION: Reverse Primer R2 for nef-C terminus

<400> SEQUENCE: 190
tgtgctggaa agccagacgg ctgtcgaatt tccacatcag    40

```
<210> SEQ ID NO 191
<211> LENGTH: 39
<212> TYPE: DNA
<213> ORGANISM: Artificial sequence
<220> FEATURE:
<223> OTHER INFORMATION: Reverse Primer R3 for nef-C terminus

<400> SEQUENCE: 191
ttccgggtgt ttttcacgag cgatgtgctg gaaagccag                     39

<210> SEQ ID NO 192
<211> LENGTH: 63
<212> TYPE: DNA
<213> ORGANISM: Artificial sequence
<220> FEATURE:
<223> OTHER INFORMATION: Reverse Primer R4 for nef-C terminus

<400> SEQUENCE: 192
aaaaaaattc ccattatttt tctcgagacc caggcagtct ttgtagtatt ccgggtgttt   60
ttc                                                            63

<210> SEQ ID NO 193
<211> LENGTH: 40
<212> TYPE: DNA
<213> ORGANISM: Artificial sequence
<220> FEATURE:
<223> OTHER INFORMATION: Forward Primer F1 for tat

<400> SEQUENCE: 193
ctttatctct aaaggtctgg gtatcagcta cggtcgtaaa                    40

<210> SEQ ID NO 194
<211> LENGTH: 46
<212> TYPE: DNA
<213> ORGANISM: Artificial sequence
<220> FEATURE:
<223> OTHER INFORMATION: Forward Primer 2 for tat

<400> SEQUENCE: 194
caaaaaatgt tgtttccact gcccggtttg ctttatctct aaaggt            46

<210> SEQ ID NO 195
<211> LENGTH: 39
<212> TYPE: DNA
<213> ORGANISM: Artificial sequence
<220> FEATURE:
<223> OTHER INFORMATION: Forward Primer F3 for tat

<400> SEQUENCE: 195
accgcttgca caactgcta ctgcaaaaaa tgttgtttc                     39

<210> SEQ ID NO 196
<211> LENGTH: 39
<212> TYPE: DNA
<213> ORGANISM: Artificial sequence
<220> FEATURE:
<223> OTHER INFORMATION: Forward Primer F4 for tat

<400> SEQUENCE: 196
aaacacccgg gtagccagcc gcgtaccgct tgcaacaac                    39

<210> SEQ ID NO 197
<211> LENGTH: 43
<212> TYPE: DNA
<213> ORGANISM: Artificial sequence
<220> FEATURE:
<223> OTHER INFORMATION: Forward Primer F5 for tat
```

```
<400> SEQUENCE: 197
accggttgac ccgcgtctgg aaccgtggaa acacccgggt agc                43

<210> SEQ ID NO 198
<211> LENGTH: 39
<212> TYPE: DNA
<213> ORGANISM: Artificial sequence
<220> FEATURE:
<223> OTHER INFORMATION: Forward Primer F6 for tat

<400> SEQUENCE: 198
gaactgaaag gtatcggtat ggaaccggtt gacccgcgt                     39

<210> SEQ ID NO 199
<211> LENGTH: 45
<212> TYPE: DNA
<213> ORGANISM: Artificial sequence
<220> FEATURE:
<223> OTHER INFORMATION: Forward Primer F7 for tat

<400> SEQUENCE: 199
cccgaattcc atatggtcga ccgtgacgaa ctgaaaggta tcggt              45

<210> SEQ ID NO 200
<211> LENGTH: 39
<212> TYPE: DNA
<213> ORGANISM: Artificial sequence
<220> FEATURE:
<223> OTHER INFORMATION: Reverse Primer R1 for tat

<400> SEQUENCE: 200
gagcgcggcg gcgctggcga cgcttttac gccgtagct                      39

<210> SEQ ID NO 201
<211> LENGTH: 42
<212> TYPE: DNA
<213> ORGANISM: Artificial sequence
<220> FEATURE:
<223> OTHER INFORMATION: Reverse Primer R2 for tat

<400> SEQUENCE: 201
aacctggtgg gtttcggagt cctgcggagc gcggcggcgc tg                 42

<210> SEQ ID NO 202
<211> LENGTH: 41
<212> TYPE: DNA
<213> ORGANISM: Artificial sequence
<220> FEATURE:
<223> OTHER INFORMATION: Reverse Primer R3 for tat

<400> SEQUENCE: 202
tggctggtcg gttgcttgct caggctaacc tggtgggttt c                  41

<210> SEQ ID NO 203
<211> LENGTH: 40
<212> TYPE: DNA
<213> ORGANISM: Artificial sequence
<220> FEATURE:
<223> OTHER INFORMATION: Reverse Primer R4 for tat

<400> SEQUENCE: 203
gaccggtcgg gtcaccacgc agctggctgg tcggttgctt                    40

<210> SEQ ID NO 204
<211> LENGTH: 39
```

```
-continued

<212> TYPE: DNA
<213> ORGANISM: Artificial sequence
<220> FEATURE:
<223> OTHER INFORMATION: Reverse Primer 5 for tat

<400> SEQUENCE: 204
aacttttttt ttgctttctt tcggaccggt cgggtcacc                                 39

<210> SEQ ID NO 205
<211> LENGTH: 39
<212> TYPE: DNA
<213> ORGANISM: Artificial sequence
<220> FEATURE:
<223> OTHER INFORMATION: Reverse Primer R6 for tat

<400> SEQUENCE: 205
cgggtcggtt tcggtttcac gttcaacttt tttttttgct                                 39

<210> SEQ ID NO 206
<211> LENGTH: 51
<212> TYPE: DNA
<213> ORGANISM: Artificial sequence
<220> FEATURE:
<223> OTHER INFORMATION: Reverse Primer R7 for tat

<400> SEQUENCE: 206
aaaaaaattc tcattatttt tctcgagaac gttcgggtcg gtttcggttt c                    51

<210> SEQ ID NO 207
<211> LENGTH: 40
<212> TYPE: DNA
<213> ORGANISM: Artificial sequence
<220> FEATURE:
<223> OTHER INFORMATION: Forward Primer F1 for rev

<400> SEQUENCE: 207
tcagatccac tccatcagcg aacgtatcct gatcacctgc                                 40

<210> SEQ ID NO 208
<211> LENGTH: 48
<212> TYPE: DNA
<213> ORGANISM: Artificial sequence
<220> FEATURE:
<223> OTHER INFORMATION: Forward Primer F2 for rev

<400> SEQUENCE: 208
aaccgccgcc gccgctggcg tgctcgtcag cgtcagatcc actccatc                        48

<210> SEQ ID NO 209
<211> LENGTH: 45
<212> TYPE: DNA
<213> ORGANISM: Artificial sequence
<220> FEATURE:
<223> OTHER INFORMATION: Forward Primer F3 for rev

<400> SEQUENCE: 209
aaaccggaag gttaccgtcg tgtccgtcgt aaccgccgcc gccgc                           45

<210> SEQ ID NO 210
<211> LENGTH: 42
<212> TYPE: DNA
<213> ORGANISM: Artificial sequence
<220> FEATURE:
<223> OTHER INFORMATION: Forward Primer F4 for rev

<400> SEQUENCE: 210
accctgtacc agtctaaccc gtacccgaaa ccggaaggtt ac                              42
```

<210> SEQ ID NO 211
<211> LENGTH: 39
<212> TYPE: DNA
<213> ORGANISM: Artificial sequence
<220> FEATURE:
<223> OTHER INFORMATION: Forward Primer F5 for rev

<400> SEQUENCE: 211
ctgctggctg ttcgtatcat caaaaccctg taccagtct                               39

<210> SEQ ID NO 212
<211> LENGTH: 48
<212> TYPE: DNA
<213> ORGANISM: Artificial sequence
<220> FEATURE:
<223> OTHER INFORMATION: Forward Primer F6 for rev

<400> SEQUENCE: 212 cccccccgaat tccatatggt cgacctgctg gctgttcgta tcatcaaa                    48

<210> SEQ ID NO 213
<211> LENGTH: 40
<212> TYPE: DNA
<213> ORGANISM: Artificial sequence
<220> FEATURE:
<223> OTHER INFORMATION: Reverse Primer R1 for rev

<400> SEQUENCE: 213
gaaccggttc ggtcggacga cccaggcagg tgatcaggat                              40

<210> SEQ ID NO 214
<211> LENGTH: 39
<212> TYPE: DNA
<213> ORGANISM: Artificial sequence
<220> FEATURE:
<223> OTHER INFORMATION: Reverse Primer R2 for rev

<400> SEQUENCE: 214
ttcgatcggc ggcagttgca gcggaaccgg ttcggtcgg                               39

<210> SEQ ID NO 215
<211> LENGTH: 39
<212> TYPE: DNA
<213> ORGANISM: Artificial sequence
<220> FEATURE:
<223> OTHER INFORMATION: Reverse Primer R3 for rev

<400> SEQUENCE: 215
ttcgctacag ttgatgttca gacgttcgat cggcggcag                               39

<210> SEQ ID NO 216
<211> LENGTH: 39
<212> TYPE: DNA
<213> ORGANISM: Artificial sequence
<220> FEATURE:
<223> OTHER INFORMATION: Reverse Primer R4 for rev

<400> SEQUENCE: 216
ctgggtaccg ctggtaccac cgctttcgct acagttgat                               39

<210> SEQ ID NO 217
<211> LENGTH: 59
<212> TYPE: DNA
<213> ORGANISM: Artificial sequence
<220> FEATURE:
<223> OTHER INFORMATION: Reverse Primer R5 for rev

<400> SEQUENCE: 217
aaaaaaattc ccattattttt tctcgagcgg gttaccaaca cgctgggtac cgctggtac    59

<210> SEQ ID NO 218
<211> LENGTH: 16
<212> TYPE: PRT
<213> ORGANISM: Artificial sequence
<220> FEATURE:
<223> OTHER INFORMATION: Fusion protein gp120-41-N1

<400> SEQUENCE: 218

Val Glu Lys Leu Trp Val Thr Val Tyr Tyr Gly Val Pro Val Trp Lys
1               5                   10                  15

<210> SEQ ID NO 219
<211> LENGTH: 16
<212> TYPE: PRT
<213> ORGANISM: Artificial sequence
<220> FEATURE:
<223> OTHER INFORMATION: Fusion protein gp120-41-N2

<400> SEQUENCE: 219

Lys Val Val Lys Ile Glu Pro Leu Gly Val Ala Pro Thr Lys Cys Lys
1               5                   10                  15

<210> SEQ ID NO 220
<211> LENGTH: 15
<212> TYPE: PRT
<213> ORGANISM: Artificial sequence
<220> FEATURE:
<223> OTHER INFORMATION: Fusion protein gp120-41-N3

<400> SEQUENCE: 220

Ala Pro Thr Lys Cys Lys Arg Arg Val Val Gln Arg Glu Lys Arg
1               5                   10                  15

<210> SEQ ID NO 221
<211> LENGTH: 14
<212> TYPE: PRT
<213> ORGANISM: Artificial sequence
<220> FEATURE:
<223> OTHER INFORMATION: Fusion protein gp120-41-C1

<400> SEQUENCE: 221

Gln Ala Arg Val Trp Arg Tyr Leu Lys Asp Gln Gln Leu Leu
1               5                   10

<210> SEQ ID NO 222
<211> LENGTH: 17
<212> TYPE: PRT
<213> ORGANISM: Artificial sequence
<220> FEATURE:
<223> OTHER INFORMATION: Fusion protein gp120-41-C2

<400> SEQUENCE: 222

Gly Ile Trp Gly Cys Ser Gly Lys Leu Ile Cys Cys Thr Thr Ala Val
1               5                   10                  15

Pro

<210> SEQ ID NO 223
<211> LENGTH: 15
<212> TYPE: PRT
<213> ORGANISM: Artificial sequence
<220> FEATURE:
<223> OTHER INFORMATION: Fusion protein gp120-41-C3

<400> SEQUENCE: 223

Ala Val Pro Trp Asn Ala Ser Ser Trp Ser Asn Lys Leu Asp Arg
1               5                   10                  15

<210> SEQ ID NO 224
<211> LENGTH: 20
<212> TYPE: PRT
<213> ORGANISM: Human immunodeficiency virus

<400> SEQUENCE: 224

Pro Val Asp Pro Arg Leu Glu Pro Trp Lys His Pro Gly Ser Gln Pro
1               5                   10                  15

Arg Thr Ala Cys
            20

<210> SEQ ID NO 225
<211> LENGTH: 20
<212> TYPE: PRT
<213> ORGANISM: Human immunodeficiency virus

<400> SEQUENCE: 225

Gln Leu Arg Gly Asp Pro Thr Gly Pro Lys Glu Ser Lys Lys Lys Val
1               5                   10                  15

Glu Arg Glu Thr
            20

<210> SEQ ID NO 226
<211> LENGTH: 20
<212> TYPE: PRT
<213> ORGANISM: Human immunodeficiency virus

<400> SEQUENCE: 226

Ser Tyr Gly Arg Lys Lys Arg Arg Gln Arg Arg Ala Pro Gln Asp
1               5                   10                  15

Ser Glu Thr His
            20

<210> SEQ ID NO 227
<211> LENGTH: 20
<212> TYPE: PRT
<213> ORGANISM: Human immunodeficiency virus

<400> SEQUENCE: 227

Gln Ser Asn Pro Tyr Pro Lys Pro Glu Gly Tyr Arg Arg Val Arg Arg
1               5                   10                  15

Asn Arg Arg Arg
            20

<210> SEQ ID NO 228
<211> LENGTH: 20
<212> TYPE: PRT
<213> ORGANISM: Human immunodeficiency virus

<400> SEQUENCE: 228

Asn Cys Ser Glu Ser Gly Gly Thr Ser Gly Thr Gln Arg Val Gly Asn
1               5                   10                  15

Pro Leu Glu Lys
            20

<210> SEQ ID NO 229
<211> LENGTH: 18
<212> TYPE: PRT
<213> ORGANISM: Human immunodeficiency virus

```
<400> SEQUENCE: 229

Ser Lys Leu Lys Lys Gly Trp Pro Thr Val Arg Gln Arg Met Asp Arg
1               5                   10                  15

Thr Glu

<210> SEQ ID NO 230
<211> LENGTH: 18
<212> TYPE: PRT
<213> ORGANISM: Human immunodeficiency virus

<400> SEQUENCE: 230

Thr Gln Gly Tyr Phe Pro Asp Trp Gln Asn Tyr Thr Pro Gly Pro Gly
1               5                   10                  15

Ile Arg

<210> SEQ ID NO 231
<211> LENGTH: 15
<212> TYPE: PRT
<213> ORGANISM: Human immunodeficiency virus

<400> SEQUENCE: 231

Val Asp Pro Glu Gln Val Glu Lys Ala Asn Glu Gly Asp Asn Asn
1               5                   10                  15

<210> SEQ ID NO 232
<211> LENGTH: 15
<212> TYPE: PRT
<213> ORGANISM: Human immunodeficiency virus

<400> SEQUENCE: 232

Ile Ser Gln His Gly Met Asp Asp Pro Glu Lys Glu Val Leu Met
1               5                   10                  15

<210> SEQ ID NO 233
<211> LENGTH: 20
<212> TYPE: PRT
<213> ORGANISM: Human immunodeficiency virus

<400> SEQUENCE: 233

Gln His Ile Ala Arg Glu Lys His Pro Glu Tyr Tyr Lys Asp Cys Leu
1               5                   10                  15

Gly Leu Glu Lys
            20

<210> SEQ ID NO 234
<211> LENGTH: 18
<212> TYPE: PRT
<213> ORGANISM: Human immunodeficiency virus

<400> SEQUENCE: 234

Pro Glu Phe His Met Val Asp Arg Asp Glu Leu Lys Gly Ile Gly Met
1               5                   10                  15

Thr Asn

<210> SEQ ID NO 235
<211> LENGTH: 15
<212> TYPE: PRT
<213> ORGANISM: Human immunodeficiency virus

<400> SEQUENCE: 235

Arg Met Tyr Ser Pro Thr Met Thr Asn Asn Pro Pro Ile Pro Val
1               5                   10                  15
```

<210> SEQ ID NO 236
<211> LENGTH: 1563
<212> TYPE: DNA
<213> ORGANISM: Artificial sequence
<220> FEATURE:
<223> OTHER INFORMATION: Fusion gene PE(delta III)-HIV-Gag24-K3

<400> SEQUENCE: 236

| | |
|---|---|
| atgggcagca gccatcatca tcatcatcac agcagcggcc tggtgccgcg cggcagccat | 60 |
| atggccgaag aagctttcga cctctggaac gaatgcgcca aagcctgcgt gctcgacctc | 120 |
| aaggacggcg tgcgttccag ccgcatgagc gtcgacccgg ccatcgccga caccaacggc | 180 |
| cagggcgtgc tgcactactc catggtcctg gagggcggca acgacgcgct caagctggcc | 240 |
| atcgacaacg ccctcagcat caccagcgac ggcctgacca tccgcctcga aggcggcgtc | 300 |
| gagccgaaca gccggtgcg ctacagctac acgcgccagg cgcgcggcag ttggtcgctg | 360 |
| aactggctgg taccgatcgg ccacgagaag ccctcgaaca tcaaggtgtt catccacgaa | 420 |
| ctgaacgccg gcaaccagct cagccacatg tcgccgatct acaccatcga gatgggcgac | 480 |
| gagttgctgg cgaagctggc gcgcgatgcc accttcttcg tcaggcgca cgagagcaac | 540 |
| gagatgcagc cgacgctcgc catcagccat gccggggtca gcgtggtcat ggcccagacc | 600 |
| cagccgcgcc gggaaaagcg ctggagcgaa tgggccagcg caaggtgtt gtgcctgctc | 660 |
| gacccgctgg acggggtcta caactacctc gcccagcaac gctgcaacct cgacgatacc | 720 |
| tgggaaggca gatctaccg ggtgctcgcc ggcaacccgg cgaagcatga cctggacatc | 780 |
| aaacccacgg tcatcagtca tcgcctgcac tttcccgagg gcggcagcct ggccgcgctg | 840 |
| accgcgcacc aggcttgcca cctgccgctg gagactttca cccgtcatcg ccagccgcgc | 900 |
| ggctgggaac aactggagca gtgcggctat ccggtgcagc ggctggtcgc cctctacctg | 960 |
| gcggcgcggc tgtcgtggaa ccaggtcgac caggtgatcc gcaacgccct ggccagcccc | 1020 |
| ggcagcggcg gcgacctggg cgaagcgatc cgcgagcagc cggagcaggc ccgtctggcc | 1080 |
| ctgaccctgg ccgccgccga gagcgagcgc ttcgtccggc agggcaccgg caacgacgag | 1140 |
| gccggcgcgg ccaacgccga cgtggtgagc ctgacctgcc cggtcgccgc cggtgaatgc | 1200 |
| gcgggcccgg cggacagcgg cgacgccctg ctggagcgca actatcccac tggcgcggag | 1260 |
| ttcctcggcg acggcggcga cgtcgaattc catatggtcg accgtgacga actgaaaggt | 1320 |
| atcggtatga ccaacaaccc gccgatcccg gttggtgaaa tctacaaacg ttggatcatc | 1380 |
| ctgggtctga acaaaatcgt tcgtatgtac agcccgacca tgaccaacaa cccgccaatt | 1440 |
| ccagtaggcg agatttaccg ttggatcatc ctgggtctga acaaaatcgt tcgcatgtac | 1500 |
| agcccgactc tcgagtacct caaaaaagac gaactgcgtg tagaactgaa agacgaactg | 1560 |
| taa | 1563 |

<210> SEQ ID NO 237
<211> LENGTH: 520
<212> TYPE: PRT
<213> ORGANISM: Artificial sequence
<220> FEATURE:
<223> OTHER INFORMATION: Fusion protein PE(delta III)-HIV Gag24-K3

<400> SEQUENCE: 237

Met Gly Ser Ser His His His His His His Ser Ser Gly Leu Val Pro
1               5                   10                  15

Arg Gly Ser His Met Ala Glu Glu Ala Phe Asp Leu Trp Asn Glu Cys
            20

```
Ala Lys Ala Cys Val Leu Asp Leu Lys Asp Gly Val Arg Ser Ser Arg
         35                  40                  45

Met Ser Val Asp Pro Ala Ile Ala Asp Thr Asn Gly Gln Gly Val Leu
     50                  55                  60

His Tyr Ser Met Val Leu Glu Gly Gly Asn Asp Ala Leu Lys Leu Ala
 65                  70                  75                  80

Ile Asp Asn Ala Leu Ser Ile Thr Ser Asp Gly Leu Thr Ile Arg Leu
                 85                  90                  95

Glu Gly Gly Val Glu Pro Asn Lys Pro Val Arg Tyr Ser Tyr Thr Arg
            100                 105                 110

Gln Ala Arg Gly Ser Trp Ser Leu Asn Trp Leu Val Pro Ile Gly His
         115                 120                 125

Glu Lys Pro Ser Asn Ile Lys Val Phe Ile His Glu Leu Asn Ala Gly
     130                 135                 140

Asn Gln Leu Ser His Met Ser Pro Ile Tyr Thr Ile Glu Met Gly Asp
145                 150                 155                 160

Glu Leu Leu Ala Lys Leu Ala Arg Asp Ala Thr Phe Phe Val Arg Ala
                165                 170                 175

His Glu Ser Asn Glu Met Gln Pro Thr Leu Ala Ile Ser His Ala Gly
            180                 185                 190

Val Ser Val Val Met Ala Gln Thr Gln Pro Arg Arg Glu Lys Arg Trp
        195                 200                 205

Ser Glu Trp Ala Ser Gly Lys Val Leu Cys Leu Leu Asp Pro Leu Asp
    210                 215                 220

Gly Val Tyr Asn Tyr Leu Ala Gln Gln Arg Cys Asn Leu Asp Asp Thr
225                 230                 235                 240

Trp Glu Gly Lys Ile Tyr Arg Val Leu Ala Gly Asn Pro Ala Lys His
                245                 250                 255

Asp Leu Asp Ile Lys Pro Thr Val Ile Ser His Arg Leu His Phe Pro
            260                 265                 270

Glu Gly Gly Ser Leu Ala Ala Leu Thr Ala His Gln Ala Cys His Leu
        275                 280                 285

Pro Leu Glu Thr Phe Thr Arg His Arg Gln Pro Arg Gly Trp Glu Gln
    290                 295                 300

Leu Glu Gln Cys Gly Tyr Pro Val Gln Arg Leu Val Ala Leu Tyr Leu
305                 310                 315                 320

Ala Ala Arg Leu Ser Trp Asn Gln Val Asp Gln Val Ile Arg Asn Ala
                325                 330                 335

Leu Ala Ser Pro Gly Ser Gly Asp Leu Gly Glu Ala Ile Arg Glu
            340                 345                 350

Gln Pro Glu Gln Ala Arg Leu Ala Leu Thr Leu Ala Ala Ala Glu Ser
        355                 360                 365

Glu Arg Phe Val Arg Gln Gly Thr Gly Asn Asp Glu Ala Gly Ala Ala
    370                 375                 380

Asn Ala Asp Val Val Ser Leu Thr Cys Pro Val Ala Ala Gly Glu Cys
385                 390                 395                 400

Ala Gly Pro Ala Asp Ser Gly Asp Ala Leu Leu Glu Arg Asn Tyr Pro
                405                 410                 415

Thr Gly Ala Glu Phe Leu Gly Asp Gly Asp Val Glu Phe His Met
            420                 425                 430

Val Asp Arg Asp Glu Leu Lys Gly Ile Gly Met Thr Asn Asn Pro Pro
        435                 440                 445

Ile Pro Val Gly Glu Ile Tyr Lys Arg Trp Ile Ile Leu Gly Leu Asn
```

```
            450                 455                 460
Lys Ile Val Arg Met Tyr Ser Pro Thr Met Thr Asn Asn Pro Pro Ile
465                 470                 475                 480

Pro Val Gly Glu Ile Tyr Arg Trp Ile Ile Leu Gly Leu Asn Lys Ile
                485                 490                 495

Val Arg Met Tyr Ser Pro Thr Leu Glu Tyr Leu Lys Lys Asp Glu Leu
            500                 505                 510

Arg Val Glu Leu Lys Asp Glu Leu
            515                 520

<210> SEQ ID NO 238
<211> LENGTH: 1863
<212> TYPE: DNA
<213> ORGANISM: Artificial sequence
<220> FEATURE:
<223> OTHER INFORMATION: Fusion gene PE(delta III)-HIV Gag24-gp120-41-K3

<400> SEQUENCE: 238
atgggcagca gccatcatca tcatcatcac agcagcggcc tggtgccgcg cggcagccat      60
atggccgaag aagctttcga cctctggaac gaatgcgcca agcctgcgt gctcgacctc      120 aaggacggcg tgcgttccag ccgcatgagc gtcgacccgg ccatcgccga caccaacggc     180
cagggcgtgc tgcactactc catggtcctg gagggcggca acgacgcgct caagctggcc     240
atcgacaacg ccctcagcat caccagcgac ggcctgacca tccgcctcga aggcggcgtc     300
gagccgaaca gccgggtgcg ctacagctac acgcgccagg cgcgcggcag ttggtcgctg     360
aactggctgg taccgatcgg ccacgagaag ccctcgaaca tcaaggtgtt catccacgaa     420
ctgaacgccg gcaaccagct cagccacatg tcgccgatct acaccatcga gatgggcgac     480
gagttgctgg cgaagctggc gcgcgatgcc accttcttcg tcagggcgca cgagagcaac     540
gagatgcagc cgacgctcgc catcagccat gccggggtca gcgtggtcat ggcccagacc     600
cagccgcgcc gggaaaagcg ctggagcgaa tgggccagcg caaggtgtt gtgcctgctc      660 gacccgctgg acggggtcta caactacctc gcccagcaac gctgcaacct cgacgatacc     720
tgggaaggca agatctaccg ggtgctcgcc ggcaacccgg cgaagcatga cctggacatc     780
aaacccacgg tcatcagtca tcgcctgcac tttcccgagg gcggcagcct ggccgcgctg     840
accgcgcacc aggcttgcca cctgccgctg gagactttca cccgtcatcg ccagccgcgc     900
ggctgggaac aactggagca gtgcggctat ccggtgcagc ggctggtcgc cctctacctg     960
gcggcgcggc tgtcgtggaa ccaggtcgac caggtgatcc gcaacgccct ggccagcccc    1020
ggcagcggcg gcgacctggg cgaagcgatc gcgagcagc cggagcaggc ccgtctggcc     1080
ctgaccctgg ccgccgccga gagcgagcgc ttcgtccggc agggcaccgg caacgacgag    1140
gccggcgcgg ccaacgccga cgtggtgagc ctgacctgcc cggtcgccgc cggtgaatgc    1200
gcgggccccg cggacagcgg cgacgccctg ctggagcgca actatcccac tggcgcggag    1260
ttcctcggcg acggcggcga cgtcgaattc catatggtcg accgtgacga actgaaaggt    1320
atcggtatga ccaacaaccc gccgatcccg gttggtgaaa tctacaaacg ttggatcatc    1380
ctgggtctga caaaatcgt tcgtatgtac agcccgacca tgaccaacaa cccgccaatt    1440
ccagtaggcg agatttaccg ttggatcatc ctgggtctga caaaatcgt tcgcatgtac     1500 agcccgactc tcgacgttga aaaactgtgg gttaccgttt actacggtgt tccggtttgg   1560 aaaaagttg ttaaaatcga accgctgggt gttgctccga ccaaatgcaa acgtcgtgtt    1620
gttcagcgtg aaaagcgtgg tggcggtggc ggtcaagctc tgttatcgc tgttgaacgt    1680
```

```
tacctgaaag accagcagct gctgggtatc tggggtggta gcggtaaact gatctgctgc    1740
accaccgctg ttccgtggaa cagcagctgg agcaacaaac tggaccgtat ctggaacaac    1800
atgacctggc tcgagtacct caaaaaagac gaactgcgtg tagaactgaa agacgaactg    1860
taa                                                                  1863

<210> SEQ ID NO 239
<211> LENGTH: 620
<212> TYPE: PRT
<213> ORGANISM: Artificial sequence
<220> FEATURE:
<223> OTHER INFORMATION: Fusion protein PE(delta III)-HIV
      Gag24-gp120-41-K3

<400> SEQUENCE: 239

Met Gly Ser Ser His His His His

```
                325                 330                 335

Leu Ala Ser Pro Gly Ser Gly Gly Asp Leu Gly Glu Ala Ile Arg Glu
            340                 345                 350

Gln Pro Glu Gln Ala Arg Leu Ala Leu Thr Leu Ala Ala Ala Glu Ser
        355                 360                 365

Glu Arg Phe Val Arg Gln Gly Thr Gly Asn Asp Glu Ala Gly Ala Ala
    370                 375                 380

Asn Ala Asp Val Val Ser Leu Thr Cys Pro Val Ala Ala Gly Glu Cys
385                 390                 395                 400

Ala Gly Pro Ala Asp Ser Gly Asp Ala Leu Leu Glu Arg Asn Tyr Pro
                405                 410                 415

Thr Gly Ala Glu Phe Leu Gly Asp Gly Gly Asp Val Glu Phe His Met
            420                 425                 430

Val Asp Arg Asp Glu Leu Lys Gly Ile Gly Met Thr Asn Asn Pro Pro
        435                 440                 445

Ile Pro Val Gly Glu Ile Tyr Lys Arg Trp Ile Ile Leu Gly Leu Asn
    450                 455                 460

Lys Ile Val Arg Met Tyr Ser Pro Thr Met Thr Asn Asn Pro Pro Ile
465                 470                 475                 480

Pro Val Gly Glu Ile Tyr Arg Trp Ile Ile Leu Gly Leu Asn Lys Ile
                485                 490                 495

Val Arg Met Tyr Ser Pro Thr Leu Asp Val Glu Lys Leu Trp Val Thr
            500                 505                 510

Val Tyr Tyr Gly Val Pro Val Trp Lys Lys Val Val Lys Ile Glu Pro
        515                 520                 525

Leu Gly Val Ala Pro Thr Lys Cys Lys Arg Arg Val Val Gln Arg Glu
    530                 535                 540

Lys Arg Gly Gly Gly Gly Gly Gln Ala Arg Val Ile Ala Val Glu Arg
545                 550                 555                 560

Tyr Leu Lys Asp Gln Gln Leu Leu Gly Ile Trp Gly Gly Ser Gly Lys
                565                 570                 575

Leu Ile Cys Cys Thr Thr Ala Val Pro Trp Asn Ser Ser Trp Ser Asn
            580                 585                 590

Lys Leu Asp Arg Ile Trp Asn Asn Met Thr Trp Leu Glu Tyr Leu Lys
        595                 600                 605

Lys Asp Glu Leu Arg Val Glu Leu Lys Asp Glu Leu
    610                 615                 620

<210> SEQ ID NO 240
<211> LENGTH: 1749
<212> TYPE: DNA
<213> ORGANISM: Artificial sequence
<220> FEATURE:
<223> OTHER INFORMATION: Fusion gene PE(delta III)-HIV nef-N-K3

<400> SEQUENCE: 240
atgggcagca gccatcatca tcatcatcac agcagcggcc tggtgccgcg cggcagccat      60
atggccgaag aagctttcga cctctggaac gaatgcgcca aagcctgcgt gctcgacctc     120
aaggacggcg tgcgttccag ccgcatgagc gtcgacccgg ccatcgccga caccaacggc     180
cagggcgtgc tgcactactc catggtcctg gagggcggca acgacgcgct caagctggcc     240
atcgacaacg ccctcagcat caccagcgac ggcctgacca tccgcctcga aggcggcgtc     300
gagccgaaca agccggtgcg ctacagctac acgcgccagg cgcgcggcag ttggtcgctg     360
aactggctgg taccgatcgg ccacgagaag ccctcgaaca tcaaggtgtt catccacgaa     420
```

-continued

```
ctgaacgccg gcaaccagct cagccacatg tcgccgatct acaccatcga gatgggcgac    480
gagttgctgg cgaagctggc gcgcgatgcc accttcttcg tcagggcgca cgagagcaac    540
gagatgcagc cgacgctcgc catcagccat gccggggtca gcgtggtcat ggcccagacc    600
cagccgcgcc gggaaaagcg ctggagcgaa tgggccagcg gcaaggtgtt gtgcctgctc    660
gacccgctgg acggggtcta caactacctc gcccagcaac gctgcaacct cgacgatacc    720
tgggaaggca agatctaccg ggtgctcgcc ggcaacccgg cgaagcatga cctggacatc    780
aaacccacgg tcatcagtca tcgcctgcac tttcccgagg gcggcagcct ggccgcgctg    840
accgcgcacc aggcttgcca cctgccgctg gagactttca cccgtcatcg ccagccgcgc    900
ggctgggaac aactggagca gtgcggctat ccggtgcagc ggctggtcgc cctctacctg    960
gcggcgcggc tgtcgtggaa ccaggtcgac caggtgatcc gcaacgccct ggccagcccc    1020
ggcagcggcg gcgacctggg cgaagcgatc cgcgagcagc cggagcaggc ccgtctggcc    1080
ctgacccttg ccgccgccga gagcgagcgc ttcgtccggc agggcaccgg caacgacgag    1140
gccggcgcgg ccaacgccga cgtggtgagc ctgacctgcc cggtcgccgc cggtgaatgc    1200
gcgggcccgg cggacagcgg cgacgccctg ctggagcgca actatcccac tggcgcggag    1260
ttcctcggcg acgcggcga cgtcgaattc catatggtcg acccgaccgt tcgtcagcgt    1320
atggaccgta ccgaaccggc tgctgagggt gttggtgctg ttagccgtga cctgaaaaaa    1380
cacggtgcta tcacctcttc taacaccgct gctaccaacg ctgactgcgc ttggctggaa    1440
gctcaggaag aagaagaagt tggttttccg gttcgtccgc aggttccgct gcgtccgatg    1500
acctacaaag ctgctgttga catcagccac ttcctgaaag aaaaaggcgg cctggaaggt    1560
ctgatctaca gccagaaacg tcaggaaatc ctggacctgt ggatctacca cacccagggc    1620
tacttcccgg actggcagaa ctacaccccg ggtccgggta tccgttaccc gctgaccttc    1680
ggctggtgtt tcaaactgct cgagtacctc aaaaaagacg aactgcgtgt agaactgaaa    1740
gacgaactg                                                            1749
```

<210> SEQ ID NO 241
<211> LENGTH: 583
<212> TYPE: PRT
<213> ORGANISM: Artificial sequence
<220> FEATURE:
<223> OTHER INFORMATION: fusion protein PE(delta III)-HIV Nef-N-K3

<400> SEQUENCE: 241

```
Met Gly Ser Ser His His His His His His Ser Ser Gly Leu Val Pro
1               5                   10                  15

Arg Gly Ser His Met Ala Glu Glu Ala Phe Asp Leu Trp Asn Glu Cys
            20                  25                  30

Ala Lys Ala Cys Val Leu Asp Leu Lys Asp Gly Val Arg Ser Ser Arg
        35                  40                  45

Met Ser Val Asp Pro Ala Ile Ala Asp Thr Asn Gly Gln Gly Val Leu
    50                  55                  60

His Tyr Ser Met Val Leu Glu Gly Gly Asn Asp Ala Leu Lys Leu Ala
65                  70                  75                  80

Ile Asp Asn Ala Leu Ser Ile Thr Ser Asp Gly Leu Thr Ile Arg Leu
                85                  90                  95

Glu Gly Gly Val Glu Pro Asn Lys Pro Val Arg Tyr Ser Tyr Thr Arg
            100                 105                 110

Gln Ala Arg Gly Ser Trp Ser Leu Asn Trp Leu Val Pro Ile Gly His
        115                 120                 125
```

-continued

Glu Lys Pro Ser Asn Ile Lys Val Phe Ile His Glu Leu Asn Ala Gly
130                 135                 140

Asn Gln Leu Ser His Met Ser Pro Ile Tyr Thr Ile Glu Met Gly Asp
145                 150                 155                 160

Glu Leu Leu Ala Lys Leu Ala Arg Asp Ala Thr Phe Phe Val Arg Ala
                165                 170                 175

His Glu Ser Asn Glu Met Gln Pro Thr Leu Ala Ile Ser His Ala Gly
            180                 185                 190

Val Ser Val Val Met Ala Gln Thr Gln Pro Arg Arg Glu Lys Arg Trp
        195                 200                 205

Ser Glu Trp Ala Ser Gly Lys Val Leu Cys Leu Leu Asp Pro Leu Asp
210                 215                 220

Gly Val Tyr Asn Tyr Leu Ala Gln Gln Arg Cys Asn Leu Asp Asp Thr
225                 230                 235                 240

Trp Glu Gly Lys Ile Tyr Arg Val Leu Ala Gly Asn Pro Ala Lys His
                245                 250                 255

Asp Leu Asp Ile Lys Pro Thr Val Ile Ser His Arg Leu His Phe Pro
            260                 265                 270

Glu Gly Gly Ser Leu Ala Ala Leu Thr Ala His Gln Ala Cys His Leu
        275                 280                 285

Pro Leu Glu Thr Phe Thr Arg His Arg Gln Pro Arg Gly Trp Glu Gln
290                 295                 300

Leu Glu Gln Cys Gly Tyr Pro Val Gln Arg Leu Val Ala Leu Tyr Leu
305                 310                 315                 320

Ala Ala Arg Leu Ser Trp Asn Gln Val Asp Gln Val Ile Arg Asn Ala
                325                 330                 335

Leu Ala Ser Pro Gly Ser Gly Gly Asp Leu Gly Glu Ala Ile Arg Glu
            340                 345                 350

Gln Pro Glu Gln Ala Arg Leu Ala Leu Thr Leu Ala Ala Ala Glu Ser
        355                 360                 365

Glu Arg Phe Val Arg Gln Gly Thr Gly Asn Asp Glu Ala Gly Ala Ala
370                 375                 380

Asn Ala Asp Val Val Ser Leu Thr Cys Pro Val Ala Ala Gly Glu Cys
385                 390                 395                 400

Ala Gly Pro Ala Asp Ser Gly Asp Ala Leu Leu Glu Arg Asn Tyr Pro
                405                 410                 415

Thr Gly Ala Glu Phe Leu Gly Asp Gly Asp Val Glu Phe His Met
            420                 425                 430

Val Asp Pro Thr Val Arg Gln Arg Met Asp Arg Thr Glu Pro Ala Ala
        435                 440                 445

Glu Gly Val Gly Ala Val Ser Arg Asp Leu Glu Lys His Gly Ala Ile
450                 455                 460

Thr Ser Ser Asn Thr Ala Ala Thr Asn Ala Asp Cys Ala Trp Leu Glu
465                 470                 475                 480

Ala Gln Glu Glu Glu Val Gly Phe Pro Val Arg Pro Gln Val Pro
                485                 490                 495

Leu Arg Pro Met Thr Tyr Lys Ala Ala Val Asp Ile Ser His Phe Leu
            500                 505                 510

Lys Glu Lys Gly Gly Leu Glu Gly Leu Ile Tyr Ser Gln Lys Arg Gln
        515                 520                 525

Glu Ile Leu Asp Leu Trp Ile Tyr His Thr Gln Gly Tyr Phe Pro Asp
530                 535                 540

Trp Gln Asn Tyr Thr Pro Gly Pro Gly Ile Arg Tyr Pro Leu Thr Phe
545                 550                 555                 560

Gly Trp Cys Phe Lys Leu Leu Glu Tyr Leu Lys Lys Asp Glu Leu Arg
                565                 570                 575

Val Glu Leu Lys Asp Glu Leu
            580

<210> SEQ ID NO 242
<211> LENGTH: 1881
<212> TYPE: DNA
<213> ORGANISM: Artificial sequence
<220> FEATURE:
<223> OTHER INFORMATION: Fusion gene PE(delta III)-HIV nef-C-K3

<400> SEQUENCE: 242

| | |
|---|---|
| atgggcagca gccatcatca tcatcatcac agcagcggcc tggtgccgcg cggcagccat | 60 |
| atggccgaag aagctttcga cctctggaac gaatgcgcca agcctgcgt gctcgacctc | 120 |
| aaggacggcg tgcgttccag ccgcatgagc gtcgacccgg ccatcgccga caccaacggc | 180 |
| cagggcgtgc tgcactactc catggtcctg gagggcggca cgacgcgct caagctggcc | 240 |
| atcgacaacg ccctcagcat caccagcgac ggcctgacca tccgcctcga aggcggcgtc | 300 |
| gagccgaaca agccggtgcg ctacagctac acgcgccagg cgcgcggcag ttggtcgctg | 360 |
| aactggctgg taccgatcgg ccacgagaag ccctcgaaca tcaaggtgtt catccacgaa | 420 |
| ctgaacgccg gcaaccagct cagccacatg tcgccgatct acaccatcga gatgggcgac | 480 |
| gagttgctgg cgaagctggc gcgcgatgcc accttcttcg tcagggcgca cgagagcaac | 540 |
| gagatgcagc cgacgctcgc catcagccat gccggggtca gcgtggtcat ggcccagacc | 600 |
| cagccgcgcc gggaaaagcg ctggagcgaa tgggccagcg gcaaggtgtt gtgcctgctc | 660 |
| gacccgctgg acggggtcta caactacctc gcccagcaac gctgcaacct cgacgatacc | 720 |
| tgggaaggca agatctaccg ggtgctcgcc ggcaacccgg cgaagcatga cctggacatc | 780 |
| aaacccacgg tcatcagtca tcgcctgcac tttcccgagg gcggcagcct ggccgcgctg | 840 |
| accgcgcacc aggcttgcca cctgccgctg gagactttca cccgtcatcg ccagccgcgc | 900 |
| ggctgggaac aactggagca gtgcggctat ccggtgcagc ggctggtcgc cctctacctg | 960 |
| gcggcgcggc tgtcgtggaa ccaggtcgac caggtgatcc gcaacgccct ggccagcccc | 1020 |
| ggcagcggcg cgacctgggc gaagcgatc cgcgagcagc cggagcaggc ccgtctggcc | 1080 |
| ctgaccctgg ccgccgccga gcgagcgc ttcgtccggc agggcaccgg caacgacgag | 1140 |
| gccggcgcgg ccaacgccga cgtggtgagc ctgacctgcc cggtcgccgc cggtgaatgc | 1200 |
| gcgggcccgg cggacagcgg cgacgccctg ctggagcgca actatcccac tggcgcggag | 1260 |
| ttcctcggcg acggcggcga cgtccgtcac cactttaccc cgagtgagcg tcaattgtgt | 1320 |
| tgtcgtcaa tccagactgc ctttaatcaa ggcgctggta cttgcatcct gtcagattct | 1380 |
| gggcgtatca gttacactgt ggagtttagt ttgcctacgc atcatactgt gcgcctgatc | 1440 |
| cgcgttacag caccaccgtc agcactcgac gcgaccgtct acaacggtag cagtaagtac | 1500 |
| ggtgacacca gcactagcaa cgtgcgtggt gaccttcaag tgttagctca gaaggcagaa | 1560 |
| cgtactctgc ctacctcctt caacttcggt gccatcaagg caactcgtgt tactgaattc | 1620 |
| catatggtcg acttcctgaa agttccggtt gacccggaac aggttgaaaa agctaacgaa | 1680 |
| ggtgataaca actgcctgct gcacccgatc agccagcacg tatgacga cccggaaaaa | 1740 |
| gaagttctga tgtggaaatt cgacagccgt ctggctttcc agcacatcgc tcgtgaaaaa | 1800 |
| cacccggaat actacaaaga ctgcctgggt ctcgagtacc tcaaaaaaga cgaactgcgt | 1860 |
| gtagaactga aagacgaact g | 1881 |

<210> SEQ ID NO 243
<211> LENGTH: 627
<212> TYPE: PRT
<213> ORGANISM: Artificial sequence
<220> FEATURE:
<223> OTHER INFORMATION: Fusion protein PE(delta III)-HIV Nef-C-K3

<400> SEQUENCE: 243

| Met | Gly | Ser | Ser | His | His | His | His | His | His | Ser | Ser | Gly | Leu | Val | Pro |
|---|---|---|---|---|---|---|---|---|---|---|---|---|---|---|---|
| 1 | | | | 5 | | | | | 10 | | | | | 15 | |

| Arg | Gly | Ser | His | Met | Ala | Glu | Glu | Ala | Phe | Asp | Leu | Trp | Asn | Glu | Cys |
| | | | 20 | | | | | 25 | | | | | 30 | | |

| Ala | Lys | Ala | Cys | Val | Leu | Asp | Leu | Lys | Asp | Gly | Val | Arg | Ser | Ser | Arg |
| | | 35 | | | | | 40 | | | | | 45 | | | |

| Met | Ser | Val | Asp | Pro | Ala | Ile | Ala | Asp | Thr | Asn | Gly | Gln | Gly | Val | Leu |
| 50 | | | | | 55 | | | | | 60 | | | | | |

| His | Tyr | Ser | Met | Val | Leu | Glu | Gly | Gly | Asn | Asp | Ala | Leu | Lys | Leu | Ala |
| 65 | | | | 70 | | | | | 75 | | | | | 80 | |

| Ile | Asp | Asn | Ala | Leu | Ser | Ile | Thr | Ser | Asp | Gly | Leu | Thr | Ile | Arg | Leu |
| | | | | 85 | | | | | 90 | | | | | 95 | |

| Glu | Gly | Gly | Val | Glu | Pro | Asn | Lys | Pro | Val | Arg | Tyr | Ser | Tyr | Thr | Arg |
| | | | 100 | | | | | 105 | | | | | 110 | | |

| Gln | Ala | Arg | Gly | Ser | Trp | Ser | Leu | Asn | Trp | Leu | Val | Pro | Ile | Gly | His |
| | | | 115 | | | | | 120 | | | | | 125 | | |

| Glu | Lys | Pro | Ser | Asn | Ile | Lys | Val | Phe | Ile | His | Glu | Leu | Asn | Ala | Gly |
| | 130 | | | | | 135 | | | | | 140 | | | | |

| Asn | Gln | Leu | Ser | His | Met | Ser | Pro | Ile | Tyr | Thr | Ile | Glu | Met | Gly | Asp |
| 145 | | | | | 150 | | | | | 155 | | | | | 160 |

| Glu | Leu | Leu | Ala | Lys | Leu | Ala | Arg | Asp | Ala | Thr | Phe | Phe | Val | Arg | Ala |
| | | | | 165 | | | | | 170 | | | | | 175 | |

| His | Glu | Ser | Asn | Glu | Met | Gln | Pro | Thr | Leu | Ala | Ile | Ser | His | Ala | Gly |
| | | | | 180 | | | | | 185 | | | | | 190 | |

| Val | Ser | Val | Val | Met | Ala | Gln | Thr | Gln | Pro | Arg | Arg | Glu | Lys | Arg | Trp |
| | | | 195 | | | | | 200 | | | | | 205 | | |

| Ser | Glu | Trp | Ala | Ser | Gly | Lys | Val | Leu | Cys | Leu | Leu | Asp | Pro | Leu | Asp |
| | 210 | | | | | 215 | | | | | 220 | | | | |

| Gly | Val | Tyr | Asn | Tyr | Leu | Ala | Gln | Gln | Arg | Cys | Asn | Leu | Asp | Asp | Thr |
| 225 | | | | | 230 | | | | | 235 | | | | | 240 |

| Trp | Glu | Gly | Lys | Ile | Tyr | Arg | Val | Leu | Ala | Gly | Asn | Pro | Ala | Lys | His |
| | | | | 245 | | | | | 250 | | | | | 255 | |

| Asp | Leu | Asp | Ile | Lys | Pro | Thr | Val | Ile | Ser | His | Arg | Leu | His | Phe | Pro |
| | | | 260 | | | | | 265 | | | | | 270 | | |

| Glu | Gly | Gly | Ser | Leu | Ala | Ala | Leu | Thr | Ala | His | Gln | Ala | Cys | His | Leu |
| | | 275 | | | | | 280 | | | | | 285 | | | |

| Pro | Leu | Glu | Thr | Phe | Thr | Arg | His | Arg | Gln | Pro | Arg | Gly | Trp | Glu | Gln |
| | 290 | | | | | 295 | | | | | 300 | | | | |

| Leu | Glu | Gln | Cys | Gly | Tyr | Pro | Val | Gln | Arg | Leu | Val | Ala | Leu | Tyr | Leu |
| 305 | | | | | 310 | | | | | 315 | | | | | 320 |

| Ala | Ala | Arg | Leu | Ser | Trp | Asn | Gln | Val | Asp | Gln | Val | Ile | Arg | Asn | Ala |
| | | | | 325 | | | | | 330 | | | | | 335 | |

| Leu | Ala | Ser | Pro | Gly | Ser | Gly | Gly | Asp | Leu | Gly | Glu | Ala | Ile | Arg | Glu |
| | | | 340 | | | | | 345 | | | | | 350 | | |

| Gln | Pro | Glu | Gln | Ala | Arg | Leu | Ala | Leu | Thr | Leu | Ala | Ala | Ala | Glu | Ser |
| | | 355 | | | | | 360 | | | | |

-continued

| | | | | | | | | | | | |
|---|---|---|---|---|---|---|---|---|---|---|---|
|Glu|Arg|Phe|Val|Arg|Gln|Gly|Thr|Gly|Asn|Asp|Glu|Ala|Gly|Ala|Ala|
| |370| | | |375| | | |380| | | | | | |

Asn Ala Asp Val Val Ser Leu Thr Cys Pro Val Ala Ala Gly Glu Cys
385                 390                 395                 400

Ala Gly Pro Ala Asp Ser Gly Asp Ala Leu Leu Glu Arg Asn Tyr Pro
            405                 410                 415

Thr Gly Ala Glu Phe Leu Gly Asp Gly Asp Val Arg His His Phe
            420                 425                 430

Thr Pro Ser Glu Arg Gln Leu Cys Leu Ser Ser Ile Gln Thr Ala Phe
            435                 440                 445

Asn Gln Gly Ala Gly Thr Cys Ile Leu Ser Asp Ser Gly Arg Ile Ser
    450                 455                 460

Tyr Thr Val Glu Phe Ser Leu Pro Thr His His Thr Val Arg Leu Ile
465                 470                 475                 480

Arg Val Thr Ala Pro Pro Ser Ala Leu Asp Ala Thr Val Tyr Asn Gly
                485                 490                 495

Ser Ser Lys Tyr Gly Asp Thr Ser Thr Ser Asn Val Arg Gly Asp Leu
            500                 505                 510

Gln Val Leu Ala Gln Lys Ala Glu Arg Thr Leu Pro Thr Ser Phe Asn
    515                 520                 525

Phe Gly Ala Ile Lys Ala Thr Arg Val Thr Glu Phe His Met Val Asp
    530                 535                 540

Phe Leu Lys Val Pro Val Asp Pro Glu Gln Val Glu Lys Ala Asn Glu
545                 550                 555                 560

Gly Asp Asn Asn Cys Leu Leu His Pro Ile Ser Gln His Gly Met Asp
                565                 570                 575

Asp Pro Glu Lys Glu Val Leu Met Trp Lys Phe Asp Ser Arg Leu Ala
            580                 585                 590

Phe Gln His Ile Ala Arg Glu Lys His Pro Glu Tyr Tyr Lys Asp Cys
        595                 600                 605

Leu Gly Leu Glu Tyr Leu Lys Lys Asp Glu Leu Arg Val Glu Leu Lys
    610                 615                 620

Asp Glu Leu
625

<210> SEQ ID NO 244
<211> LENGTH: 1953
<212> TYPE: DNA
<213> ORGANISM: Artificial sequence
<220> FEATURE:
<223> OTHER INFORMATION: Fusion gene PE(delta III)-HIV nef-NC-K3

<400> SEQUENCE: 244
atgggcagca gccatcatca tcatcatcac agcagcggcc tggtgccgcg cggcagccat      60
atggccgaag aagctttcga cctctggaac gaatgcgcca agcctgcgt gctcgacctc     120 aaggacggcg tgcgttccag ccgcatgagc gtcgacccgg ccatcgccga caccaacggc     180
cagggcgtgc tgcactactc catggtcctg gagggcggca acgacgcgct caagctggcc     240
atcgacaacg ccctcagcat caccagcgac ggcctgacca tccgcctcga aggcggcgtc     300
gagccgaaca gccggtgcg ctacagctac acgcgccagg cgcgcggcag ttggtcgctg     360
aactggctgg taccgatcgg ccacgagaag ccctcgaaca tcaaggtgtt catccacgaa     420
ctgaacgccg gcaaccagct cagccacatg tcgccgatct acaccatcga gatgggcgac     480
gagttgctgg cgaagctggc gcgcgatgcc accttcttcg tcagggcgca cgagagcaac     540
gagatgcagc cgacgctcgc catcagccat gccggggtca gcgtggtcat ggcccagacc     600

```
cagccgcgcc gggaaaagcg ctggagcgaa tgggccagcg gcaaggtgtt gtgcctgctc      660
gacccgctgg acggggtcta caactacctc gcccagcaac gctgcaacct cgacgatacc      720
tgggaaggca agatctaccg ggtgctcgcc ggcaacccgg cgaagcatga cctggacatc      780
aaacccacgg tcatcagtca tcgcctgcac tttcccgagg gcggcagcct ggccgcgctg      840
accgcgcacc aggcttgcca cctgccgctg gagactttca cccgtcatcg ccagccgcgc      900
ggctgggaac aactggagca gtgcggctat ccggtgcagc ggctggtcgc cctctacctg      960
gcggcgcggt tgtcgtggaa ccaggtcgac caggtgatcc gcaacgccct ggccagcccc     1020
ggcagcggcg gcgacctggg cgaagcgatc cgcgagcagc cggagcaggc ccgtctggcc     1080
ctgaccctgg ccgccgccga gagcgagcgc ttcgtccggc agggcaccgg caacgacgag     1140 gccgcgcgg ccaacgccga cgtggtgagc ctgacctgcc cggtcgccgc cggtgaatgc     1200
gcgggcccgg cggacagcgg cgacgccctg ctggagcgca actatcccac tggcgcggag     1260
ttcctcggcg acggcggcga cgtcgaattc catatggtcg acccgaccgt tcgtcagcgt     1320
atggaccgta ccgaaccggc tgctgagggt gttggtgctg ttagccgtga cctggaaaaa     1380
cacggtgcta tcacctcttc taacaccgct gctaccaacg ctgactgcgc ttggctggaa     1440
gctcaggaag aagaagaagt tggtttccg gttcgtccgc aggttccgct gcgtccgatg     1500
acctacaaag ctgctgttga catcagccac ttcctgaaag aaaaaggcgg cctggaaggt     1560
ctgatctaca gccagaaacg tcaggaaatc ctggacctgt ggatctacca cacccagggc     1620
tacttcccgg actggcagaa ctacaccccg ggtccgggta ccgttaccc gctgaccttc     1680 ggctggtgtt tcaaactgct cgacttcctg aaagttccgg ttgacccgga acaggttgaa     1740
aaagctaacg aaggtgataa caactgcctg ctgcacccga tcagccagca cggtatggac     1800
gacccggaaa agaagttct gatgtggaaa ttcgacagcc gtctggcttt ccagcacatc     1860
gctcgtgaaa acaccccgga atactacaaa gactgcctgg gtctcgagta cctcaaaaaa     1920
gacgaactgc gtgtagaact gaaagacgaa ctg                                  1953
```

<210> SEQ ID NO 245
<211> LENGTH: 651
<212> TYPE: PRT
<213> ORGANISM: Artificial sequence
<220> FEATURE:
<223> OTHER INFORMATION: Fusion protein PE(delta III)-HIV Nef-NC-K3

<400> SEQUENCE: 245

```
Met Gly Ser Ser His His His His His His Ser Ser Gly Leu Val Pro
1               5                   10                  15

Arg Gly Ser His Met Ala Glu Glu Ala Ph

-continued

```
Glu Lys Pro Ser Asn Ile Lys Val Phe Ile His Glu Leu Asn Ala Gly
        130                 135                 140
Asn Gln Leu Ser His Met Ser Pro Ile Tyr Thr Ile Glu Met Gly Asp
145                 150                 155                 160
Glu Leu Leu Ala Lys Leu Ala Arg Asp Ala Thr Phe Phe Val Arg Ala
                165                 170                 175
His Glu Ser Asn Glu Met Gln Pro Thr Leu Ala Ile Ser His Ala Gly
            180                 185                 190
Val Ser Val Val Met Ala Gln Thr Gln Pro Arg Arg Glu Lys Arg Trp
        195                 200                 205
Ser Glu Trp Ala Ser Gly Lys Val Leu Cys Leu Leu Asp Pro Leu Asp
210                 215                 220
Gly Val Tyr Asn Tyr Leu Ala Gln Gln Arg Cys Asn Leu Asp Asp Thr
225                 230                 235                 240
Trp Glu Gly Lys Ile Tyr Arg Val Leu Ala Gly Asn Pro Ala Lys His
                245                 250                 255
Asp Leu Asp Ile Lys Pro Thr Val Ile Ser His Arg Leu His Phe Pro
                260                 265                 270
Glu Gly Gly Ser Leu Ala Ala Leu Thr Ala His Gln Ala Cys His Leu
            275                 280                 285
Pro Leu Glu Thr Phe Thr Arg His Arg Gln Pro Arg Gly Trp Glu Gln
290                 295                 300
Leu Glu Gln Cys Gly Tyr Pro Val Gln Arg Leu Val Ala Leu Tyr Leu
305                 310                 315                 320
Ala Ala Arg Leu Ser Trp Asn Gln Val Asp Gln Val Ile Arg Asn Ala
                325                 330                 335
Leu Ala Ser Pro Gly Ser Gly Gly Asp Leu Gly Glu Ala Ile Arg Glu
            340                 345                 350
Gln Pro Glu Gln Ala Arg Leu Ala Leu Thr Leu Ala Ala Ala Glu Ser
        355                 360                 365
Glu Arg Phe Val Arg Gln Gly Thr Gly Asn Asp Glu Ala Gly Ala Ala
370                 375                 380
Asn Ala Asp Val Val Ser Leu Thr Cys Pro Val Ala Ala Gly Glu Cys
385                 390                 395                 400
Ala Gly Pro Ala Asp Ser Gly Asp Ala Leu Leu Glu Arg Asn Tyr Pro
                405                 410                 415
Thr Gly Ala Glu Phe Leu Gly Asp Gly Asp Val Glu Phe His Met
                420                 425                 430
Val Asp Pro Thr Val Arg Gln Arg Met Asp Arg Thr Glu Pro Ala Ala
        435                 440                 445
Glu Gly Val Gly Ala Val Ser Arg Asp Leu Glu Lys His Gly Ala Ile
    450                 455                 460
Thr Ser Ser Asn Thr Ala Ala Thr Asn Ala Asp Cys Ala Trp Leu Glu
465                 470                 475                 480
Ala Gln Glu Glu Glu Glu Val Gly Phe Pro Val Arg Pro Gln Val Pro
                485                 490                 495
Leu Arg Pro Met Thr Tyr Lys Ala Ala Val Asp Ile Ser His Phe Leu
                500                 505                 510
Lys Glu Lys Gly Gly Leu Glu Gly Leu Ile Tyr Ser Gln Lys Arg Gln
            515                 520                 525
Glu Ile Leu Asp Leu Trp Ile Tyr His Thr Gln Gly Tyr Phe Pro Asp
530                 535                 540
Trp Gln Asn Tyr Thr Pro Gly Pro Gly Ile Arg Tyr Pro Leu Thr Phe
```

```
545             550             555             560
Gly Trp Cys Phe Lys Leu Leu Asp Phe Leu Lys Val Pro Val Asp Pro
                565             570             575
Glu Gln Val Glu Lys Ala Asn Glu Gly Asp Asn Asn Cys Leu Leu His
            580             585             590
Pro Ile Ser Gln His Gly Met Asp Asp Pro Glu Lys Glu Val Leu Met
        595             600             605
Trp Lys Phe Asp Ser Arg Leu Ala Phe Gln His Ile Ala Arg Glu Lys
    610             615             620
His Pro Glu Tyr Tyr Lys Asp Cys Leu Gly Leu Glu Tyr Leu Lys Lys
625             630             635             640
Asp Glu Leu Arg Val Glu Leu Lys Asp Glu Leu
                645             650

<210> SEQ ID NO 246
<211> LENGTH: 1947
<212> TYPE: DNA
<213> ORGANISM: Artificial sequence
<220> FEATURE:
<223> OTHER INFORMATION: Fusion gene PE(delta III)-HIV rev-K3

<400> SEQUENCE: 246
atgggcagca gccatcatca tcatcatcac agcagcggcc tggtgccgcg cggcagccat       60
atggccgaag aagctttcga cctctggaac gaatgcgcca agcctgcgt gctcgacctc      120
aaggacggcg tgcgttccag ccgcatgagc gtcgacccgg ccatcgccga caccaacggc      180
cagggcgtgc tgcactactc catggtcctg gagggcggca cgacgcgct caagctggcc      240
atcgacaacg ccctcagcat caccagcgac ggcctgacca tccgcctcga aggcggcgtc      300
gagccgaaca agccggtgcg ctacagctac acgcgccagg cgcgcggcag ttggtcgctg      360
aactggctgg taccgatcgg ccacgagaag ccctcgaaca tcaaggtgtt catccacgaa      420
ctgaacgccg gcaaccagct cagccacatg tcgccgatct acaccatcga gatgggcgac      480
gagttgctgg cgaagctggc gcgcgatgcc accttcttcg tcagggcgca cgagagcaac      540
gagatgcagc cgacgctcgc catcagccat gccggggtca gcgtggtcat ggcccagacc      600
cagccgcgcc gggaaaagcg ctggagcgaa tgggccagcg gcaaggtgtt gtgcctgctc      660
gacccgctga cggggtctca caactacctc gcccagcaac gctgcaacct cgacgatacc      720
tgggaaggca agatctaccg ggtgctcgcc ggcaacccgg cgaagcatga cctggacatc      780
aaacccacgg tcatcagtca tcgcctgcac tttcccgagg gcggcagcct ggccgcgctg      840
accgcgcacc aggcttgcca cctgccgctg gagactttca cccgtcatcg ccagccgcgc      900
ggctgggaac aactggagca gtgcggctat ccggtgcagc ggctggtcgc cctctacctg      960
gcggcgcggc tgtcgtggaa ccaggtcgac caggtgatcc gcaacgccct ggccagcccc     1020
ggcagcggcg cgacctgggc gaagcgatc cgcgagcagc cggagcaggc ccgtctggcc     1080
ctgaccctgg ccgccgccga gcgagcgc ttcgtccggc agggcaccgg caacgacgag     1140
gccgcgcgcg ccaacgccga cgtggtgagc ctgacctgcc cggtcgccgc cggtgaatgc     1200
gcgggcccgg cggacagcgg cgacgccctg ctggagcgca actatcccac tggcgcggag     1260
ttcctcggcg acgcggcga cgtccgtcac cactttaccc cgagtgagcg tcaattgtgt     1320
ttgtcgtcaa tccagactgc ctttaatcaa ggcgctggta cttgcatcct gtcagattct     1380
gggcgtatca gttacactgt ggagtttagt ttgcctacgc atcatactgt gcgcctgatc     1440
cgcgttacag caccaccgtc agcactcgac gcgaccgtct acaacggtag cagtaagtac     1500
```

```
ggtgacacca gcactagcaa cgtgcgtggt gaccttcaag tgttagctca gaaggcagaa    1560
cgtactctgc ctacctcctt caacttcggt gccatcaagg caactcgtgt tactgaattc    1620
catatggtcg acctgctggc tgttcgtatc atcaaaaccc tgtaccagtc taacccgtac    1680
ccgaaaccgg aaggttaccg tcgtgtccgt cgtaaccgcc gccgccgctg cgtgctcgt     1740 cagcgtcaga tccactccat cagcgaacgt atcctgatca cctgcctggg tcgtccgacc    1800
gaaccggttc cgctgcaact gccgccgatc gaacgtctga acatcaactg tagcgaaagc    1860
ggtggtacca gcggtaccca gcgtgttggt aacccgctcg agtacctcaa aaaagacgaa    1920
ctgcgtgtag aactgaaaga cgaactg                                        1947
```

<210> SEQ ID NO 247
<211> LENGTH: 649
<212> TYPE: PRT
<213> ORGANISM: Artificial sequence
<220> FEATURE:
<223> OTHER INFORMATION: Fusion protein PE(delta III)-HIV Rev-K3

<400> SEQUENCE: 247

```
Met Gly Ser Ser His His His His His His Ser Ser Gly Leu Val Pro
1               5                   10                  15

Arg Gly Ser His Met Ala Glu Glu Ala Phe Asp Leu Trp Asn Glu Cys
            20                  25                  30

Ala Lys Ala Cys Val Leu Asp Leu Lys Asp Gly Val Arg Ser Ser Arg
        35                  40                  45

Met Ser Val Asp Pro Ala Ile Ala Asp Thr Asn Gly Gln Gly Val Leu
    50                  55                  60

His Tyr Ser Met Val Leu Glu Gly Gly Asn Asp Ala Leu Lys Leu Ala
65                  70                  75                  80

Ile Asp Asn Ala Leu Ser Ile Thr Ser Asp Gly Leu Thr Ile Arg Leu
                85                  90                  95

Glu Gly Gly Val Glu Pro Asn Lys Pro Val Arg Tyr Ser Tyr Thr Arg
            100                 105                 110

Gln Ala Arg Gly Ser Trp Ser Leu Asn Trp Leu Val Pro Ile Gly His
        115                 120                 125

Glu Lys Pro Ser Asn Ile Lys Val Phe Ile His Glu Leu Asn Ala Gly
    130                 135                 140

Asn Gln Leu Ser His Met Ser Pro Ile Tyr Thr Ile Glu Met Gly Asp
145                 150                 155                 160

Glu Leu Leu Ala Lys Leu Ala Arg Asp Ala Thr Phe Phe Val Arg Ala
                165                 170                 175

His Glu Ser Asn Glu Met Gln Pro Thr Leu Ala Ile Ser His Ala Gly
            180                 185                 190

Val Ser Val Val Met Ala Gln Thr Gln Pro Arg Arg Glu Lys Arg Trp
        195                 200                 205

Ser Glu Trp Ala Ser Gly Lys Val Leu Cys Leu Leu Asp Pro Leu Asp
    210                 215                 220

Gly Val Tyr Asn Tyr Leu Ala Gln Gln Arg Cys Asn Leu Asp Asp Thr
225                 230                 235                 240

Trp Glu Gly Lys Ile Tyr Arg Val Leu Ala Gly Asn Pro Ala Lys His
                245                 250                 255

Asp Leu Asp Ile Lys Pro Thr Val Ile Ser His Arg Leu His Phe Pro
            260                 265                 270

Glu Gly Gly Ser Leu Ala Ala Leu Thr Ala His Gln Ala Cys His Leu
        275                 280                 285
```

```
Pro Leu Glu Thr Phe Thr Arg His Arg Gln Pro Arg Gly Trp Glu Gln
    290                 295                 300

Leu Glu Gln Cys Gly Tyr Pro Val Gln Arg Leu Val Ala Leu Tyr Leu
305                 310                 315                 320

Ala Ala Arg Leu Ser Trp Asn Gln Val Asp Gln Val Ile Arg Asn Ala
                325                 330                 335

Leu Ala Ser Pro Gly Ser Gly Gly Asp Leu Gly Glu Ala Ile Arg Glu
            340                 345                 350

Gln Pro Glu Gln Ala Arg Leu Ala Leu Thr Leu Ala Ala Ala Glu Ser
        355                 360                 365

Glu Arg Phe Val Arg Gln Gly Thr Gly Asn Asp Glu Ala Gly Ala Ala
    370                 375                 380

Asn Ala Asp Val Val Ser Leu Thr Cys Pro Val Ala Ala Gly Glu Cys
385                 390                 395                 400

Ala Gly Pro Ala Asp Ser Gly Asp Ala Leu Leu Glu Arg Asn Tyr Pro
                405                 410                 415

Thr Gly Ala Glu Phe Leu Gly Asp Gly Gly Asp Val Arg His His Phe
            420                 425                 430

Thr Pro Ser Glu Arg Gln Leu Cys Leu Ser Ser Ile Gln Thr Ala Phe
        435                 440                 445

Asn Gln Gly Ala Gly Thr Cys Ile Leu Ser Asp Ser Gly Arg Ile Ser
    450                 455                 460

Tyr Thr Val Glu Phe Ser Leu Pro Thr His His Thr Val Arg Leu Ile
465                 470                 475                 480

Arg Val Thr Ala Pro Pro Ser Ala Leu Asp Ala Thr Val Tyr Asn Gly
                485                 490                 495

Ser Ser Lys Tyr Gly Asp Thr Ser Thr Ser Asn Val Arg Gly Asp Leu
            500                 505                 510

Gln Val Leu Ala Gln Lys Ala Glu Arg Thr Leu Pro Thr Ser Phe Asn
        515                 520                 525

Phe Gly Ala Ile Lys Ala Thr Arg Val Thr Glu Phe His Met Val Asp
    530                 535                 540

Leu Leu Ala Val Arg Ile Ile Lys Thr Leu Tyr Gln Ser Asn Pro Tyr
545                 550                 555                 560

Pro Lys Pro Glu Gly Tyr Arg Arg Val Arg Arg Asn Arg Arg Arg Arg
                565                 570                 575

Trp Arg Ala Arg Gln Arg Gln Ile His Ser Ile Ser Glu Arg Ile Leu
            580                 585                 590

Ile Thr Cys Leu Gly Arg Pro Thr Glu Pro Val Pro Leu Gln Leu Pro
        595                 600                 605

Pro Ile Glu Arg Leu Asn Ile Asn Cys Ser Glu Ser Gly Gly Thr Ser
    610                 615                 620

Gly Thr Gln Arg Val Gly Asn Pro Leu Glu Tyr Leu Lys Lys Asp Glu
625                 630                 635                 640

Leu Arg Val Glu Leu Lys Asp Glu Leu
                645
```

<210> SEQ ID NO 248
<211> LENGTH: 1680
<212> TYPE: DNA
<213> ORGANISM: Artificial sequence
<220> FEATURE:
<223> OTHER INFORMATION: Fusion gene PE(delta III)-HIV tat-K3

<400> SEQUENCE: 248
atgggcagca gccatcatca tcatcatcac agcagcggcc tggtgccgcg cggcagccat     60

```
atggccgaag aagctttcga cctctggaac gaatgcgcca aagcctgcgt gctcgacctc    120
aaggacggcg tgcgttccag ccgcatgagc gtcgacccgg ccatcgccga caccaacggc    180
cagggcgtgc tgcactactc catggtcctg gagggcggca acgacgcgct caagctggcc    240
atcgacaacg ccctcagcat caccagcgac ggcctgacca tccgcctcga aggcggcgtc    300
gagccgaaca gccggtgcgc tacagctac acgcgccagg cgcgcggcag ttggtcgctg    360
aactggctgg taccgatcgg ccacgagaag ccctcgaaca tcaaggtgtt catccacgaa    420
ctgaacgccg gcaaccagct cagccacatg tcgccgatct acaccatcga gatgggcgac    480
gagttgctgg cgaagctggc gcgcgatgcc accttcttcg tcagggcgca cgagagcaac    540
gagatgcagc cgacgctcgc catcagccat gccggggtca gcgtggtcat ggcccagacc    600
cagccgcgcc gggaaaagcg ctggagcgaa tgggccagcg caaggtgtt gtgcctgctc    660 gacccgctgg acgggtcta caactacctc gcccagcaac gctgcaacct cgacgatacc    720
tgggaaggca agatctaccg ggtgctcgcc ggcaacccgg cgaagcatga cctggacatc    780
aaacccacgg tcatcagtca tcgcctgcac ttcccgaggg cggcagcct ggccgcgctg    840 accgcgcacc aggcttgcca cctgccgctg gagacttca cccgtcatcg ccagccgcgc    900
ggctgggaac aactggagca gtgcggctat ccggtgcagc ggctggtcgc cctctacctg    960
gcggcgcggc tgtcgtggaa ccaggtcgac caggtgatcc gcaacgccct ggccagcccc   1020
ggcagcggcg gcgacctggg cgaagcgatc cgcgagcagc cggagcaggc ccgtctggcc   1080
ctgaccctgg ccgccgccga gcgagcgc ttcgtccggc agggcaccgg caacgacgag   1140
gccggcgcgg ccaacgccga cgtggtgagc ctgacctgcc cggtcgccgc cggtgaatgc   1200 gcgggccccgg cggacagcgg cgacgccctg ctggagcgca actatccac tggcgcggag   1260 ttcctcggcg acggcggcga cgtcgaattc catatggtcg accgtgacga actgaaaggt   1320
atcggtatgg aaccggttga cccgcgtctg gaaccgtgga acacccggg tagccagccg   1380 cgtaccgctt gcaacaactg ctactgcaaa aaatgttgtt tccactgccc ggtttgcttt   1440
atctctaaag gtctgggtat cagctacggt cgtaaaaagc gtcgccagcg ccgccgcgct   1500
ccgcaggact ccgaaaccca ccaggttagc ctgagcaagc aaccgaccag ccagctgcgt   1560
ggtgacccga ccggtccgaa agaaagcaaa aaaaaagttg aacgtgaaac cgaaaccgac   1620
ccgaacgttc tcgagtacct caaaaaagac gaactgcgtg tagaactgaa agacgaactg   1680
```

<210> SEQ ID NO 249
<211> LENGTH: 560
<212> TYPE: PRT
<213> ORGANISM: Artificial sequence
<220> FEATURE:
<223> OTHER INFORMATION: Fusion protein PE(delta III)-HIV Tat-K3

<400> SEQUENCE: 249

```
Met Gly Ser Ser His His His His His His Ser Gly Leu Val Pro
1               5                   10                  15

Arg Gly Ser His Met Ala Glu Glu Ala Phe Asp Leu Trp Asn Glu Cys
            20                  25                  30

Ala L

```
Ile Asp Asn Ala Leu Ser Ile Thr Ser Asp Gly Leu Thr Ile Arg Leu
                85                  90                  95

Glu Gly Gly Val Glu Pro Asn Lys Pro Val Arg Tyr Ser Tyr Thr Arg
            100                 105                 110

Gln Ala Arg Gly Ser Trp Ser Leu Asn Trp Leu Val Pro Ile Gly His
        115                 120                 125

Glu Lys Pro Ser Asn Ile Lys Val Phe Ile His Glu Leu Asn Ala Gly
    130                 135                 140

Asn Gln Leu Ser His Met Ser Pro Ile Tyr Thr Ile Glu Met Gly Asp
145                 150                 155                 160

Glu Leu Leu Ala Lys Leu Ala Arg Asp Ala Thr Phe Phe Val Arg Ala
                165                 170                 175

His Glu Ser Asn Glu Met Gln Pro Thr Leu Ala Ile Ser His Ala Gly
            180                 185                 190

Val Ser Val Val Met Ala Gln Thr Gln Pro Arg Arg Glu Lys Arg Trp
        195                 200                 205

Ser Glu Trp Ala Ser Gly Lys Val Leu Cys Leu Leu Asp Pro Leu Asp
    210                 215                 220

Gly Val Tyr Asn Tyr Leu Ala Gln Gln Arg Cys Asn Leu Asp Asp Thr
225                 230                 235                 240

Trp Glu Gly Lys Ile Tyr Arg Val Leu Ala Gly Asn Pro Ala Lys His
                245                 250                 255

Asp Leu Asp Ile Lys Pro Thr Val Ile Ser His Arg Leu His Phe Pro
            260                 265                 270

Glu Gly Gly Ser Leu Ala Ala Leu Thr Ala His Gln Ala Cys His Leu
        275                 280                 285

Pro Leu Glu Thr Phe Thr Arg His Arg Gln Pro Arg Gly Trp Glu Gln
    290                 295                 300

Leu Glu Gln Cys Gly Tyr Pro Val Gln Arg Leu Val Ala Leu Tyr Leu
305                 310                 315                 320

Ala Ala Arg Leu Ser Trp Asn Gln Val Asp Gln Val Ile Arg Asn Ala
                325                 330                 335

Leu Ala Ser Pro Gly Ser Gly Gly Asp Leu Gly Glu Ala Ile Arg Glu
            340                 345                 350

Gln Pro Glu Gln Ala Arg Leu Ala Leu Thr Leu Ala Ala Ala Glu Ser
        355                 360                 365

Glu Arg Phe Val Arg Gln Gly Thr Gly Asn Asp Glu Ala Gly Ala Ala
    370                 375                 380

Asn Ala Asp Val Val Ser Leu Thr Cys Pro Val Ala Ala Gly Glu Cys
385                 390                 395                 400

Ala Gly Pro Ala Asp Ser Gly Asp Ala Leu Leu Glu Arg Asn Tyr Pro
                405                 410                 415

Thr Gly Ala Glu Phe Leu Gly Asp Gly Asp Val Glu Phe His Met
            420                 425                 430

Val Asp Arg Asp Glu Leu Lys Gly Ile Gly Met Glu Pro Val Asp Pro
        435                 440                 445

Arg Leu Glu Pro Trp Lys His Pro Gly Ser Gln Pro Arg Thr Ala Cys
    450                 455                 460

Asn Asn Cys Tyr Cys Lys Lys Cys Cys Phe His Cys Pro Val Cys Phe
465                 470                 475                 480

Ile Ser Lys Gly Leu Gly Ile Ser Tyr Gly Arg Lys Lys Arg Arg Gln
                485                 490                 495

Arg Arg Arg Ala Pro Gln Asp Ser Glu Thr His Gln Val Ser Leu Ser
            500                 505                 510
```

-continued

```
Lys Gln Pro Thr Ser Gln Leu Arg Gly Asp Pro Thr Gly Pro Lys Glu
        515                 520                 525

Ser Lys Lys Val Glu Arg Glu Thr Glu Thr Asp Pro Asn Val Leu
    530                 535                 540

Glu Tyr Leu Lys Lys Asp Glu Leu Arg Val Glu Leu Lys Asp Glu Leu
545                 550                 555                 560

<210> SEQ ID NO 250
<211> LENGTH: 12
<212> TYPE: PRT
<213> ORGANISM: Artificial sequence
<220> FEATURE:
<223> OTHER INFORMATION: Carboxyl terminal moiety

<400> SEQUENCE: 250

Lys Lys Asp Leu Arg Asp Glu Leu Lys Asp Glu Leu
1               5                   10

<210> SEQ ID NO 251
<211> LENGTH: 13
<212> TYPE: PRT
<213> ORGANISM: Artificial sequence
<220> FEATURE:
<223> OTHER INFORMATION: Carboxyl terminal moiety

<400> SEQUENCE: 251

Lys Lys Asp Glu Leu Arg Asp Glu Leu Lys Asp Glu Leu
1               5                   10

<210> SEQ ID NO 252
<211> LENGTH: 13
<212> TYPE: PRT
<213> ORGANISM: Artificial sequence
<220> FEATURE:
<223> OTHER INFORMATION: Carboxyl terminal moiety

<400> SEQUENCE: 252

Lys Lys Asp Glu Leu Arg Val Glu Leu Lys Asp Glu Leu
1               5                   10
```

CHIMERIC HIV FUSION PROTEINS AS VACCINES

REFERENCE TO RELATED APPLICATION

Figure 1A:
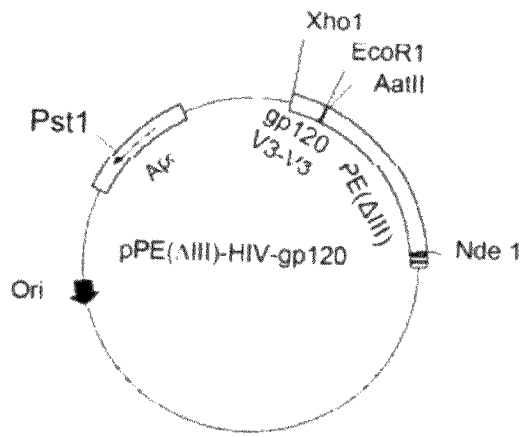
Figure 1B:
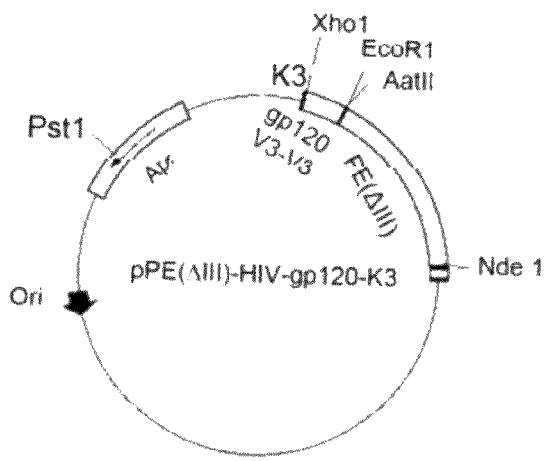
Figure 1C:
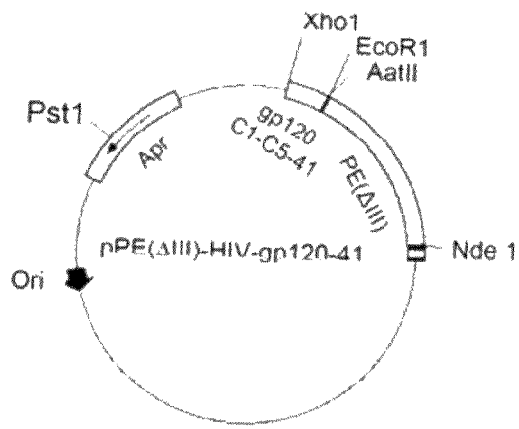
Figure 1D:
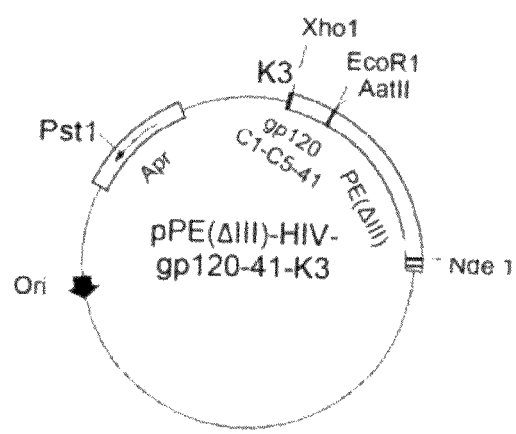

This application is a divisional application of U.S. Ser. No. 12/358,659, filed Jan. 23, 2009, which status is pending and claims the priority of U.S. provisional application No. 61/025,094, filed Jan. 31, 2008, all of which are herein incorporated by reference in its entirety.

FIELD OF THE INVENTION

The present invention relates generally to HIV vaccines, and more specifically to chimeric HIV fusion proteins useful for inducing humoral and cell-mediated immune responses.

BACKGROUND OF THE INVENTION

The global epidemic of AIDS has created an urgent need for a vaccine against human immunodeficiency virus type 1 (HIV-1). It is likely that effective AIDS vaccines will need to generate efficient humoral and cellular immune responses. Virus-neutralizing antibodies and anti-HIV cytotoxic (CD8+) T lymphocytes (CTLs) mediated immunity are major requirements for protective immune responses elicited by HIV vaccines.

HIV has several major genes coding for viral proteins. The gag gene codes for p24, the viral capsid; p6 and p7, the nucleocapsid proteins; and p17, a matrix protein. The pol gene codes for reverse transcriptase, integrase, and protease which cleaves the proteins derived from gag and pol into functional proteins. The env gene codes for the precursor to gp120 and gp41, envelope proteins embedded in the viral envelope that enable the virus to attach to and fuse with target cells. The tat, rev, nef, vif, vpr, vpu genes each codes for a single protein with the same names, Tat, Rev, Nef, Vif, Vpr, Vpu, respectively.

Neutralizing antibodies have been shown to contribute to protection from virus infection in animal models of HIV-1 infection. The virus-specific targets on HIV-1 accessible to neutralizing antibodies are the envelope glycoproteins (Yang, X. et al. (2005) "Stoichiometry of Antibody Neutralization of Human Immunodeficiency Virus Type 1" *Journal of Virology* 79: 3500-3508). During the normal course of HIV-1 infections, virus-neutralizing antibodies are often generated but the titer of neutralizing is often low. Most neutralizing antibodies bind the gp120 envelope glycoprotein, which is the major exposed protein of the viral envelope glycoprotein trimer. The more conserved receptor-binding surfaces of the HIV-1 gp120 glycoprotein are also the targets for neutralizing antibodies. The CD4-binding site (CD4BS) antibodies recognize a conformational epitope composed of several segments of gp120 region that overlaps the binding site for CD4. CD4-induced (CD4i) antibodies bind a highly conserved gp120 element that is critical for the gp120-chemokine receptor interaction. The ability of CDBS and CD4i antibodies to interfere with receptor binding contributes to their neutralizing capability.

GP 120 contains ten domains: conserved domains 1-5 (C1-C5) and variable domains 1-5 (V1-V5). The C1 and C5 domains are located at N- and C-terminals of gp120, respectively. Antibodies directed against the V3 loop, which determines chemokine receptor choice, can block the binding of gp 120 to the receptors CCR5 and/or CXCR4. Neutralization by anti-V3 antibodies, although potent, is often limited to a small number of HIV-1 strains.

Gp120 is non-covalently associated with gp41. The gp41 subunit is anchored in the membrane and has a non-polar fusion peptide at its N-terminus. The gp120-gp41 complex forms oligomers on the surface of infected cells and on virions. The binding of gp 120 to CD4 is thought to result in activation of the membrane fusion activity of gp41, leading to entry of the viral nucleocapsid into a cell a Antibodies to gp41 epitopes in the serum of HIV-infected individuals may play an important role in virus neutralization. Gp120-41 complex sequences of different HIV subtypes show a remarkably conserved N-terminal coiled-coil structures of gp41 as well as the C-terminal residues that interact with the N-terminal core structure of gp120.

Multiple immune effectors participate in prevention, containment and clearance of HIV infection. To prevent infection of host target cells, antibodies are required. After the first target cells have been infected with virus, it is important to have cytotoxic T lymphocytes (CTLs) as well as antibodies to reduce cell-to-cell spread and kill infected cells. An effective HIV vaccine should evoke antibodies that can bind to virus and prevent attachment of virus to target cells, as well as CTLs that can eliminate any cells that become infected.

It remains a difficult goal for vaccinologists to construct live-attenuated viruses that are both effective and safe, or to mimic the presentation of viral proteins observed in infection with recombinant antigens or with replicating or non-replicating vectors carrying appropriate genes or antigens. The large number of mutations in the V3 domain of gp120 has limited its usefulness as a target for HIV vaccine. It is still unclear how the trend of hypervariability in the variable domains is developing and how many domains are absolutely invariant in the evolving strains of HIV.

A previously unaddressed need exists in the art to address the deficiencies and inadequacies in HIV vaccine antigen production, especially in connection with the provision of efficacious, antigenic determinant peptides.

SUMMARY OF THE INVENTION

The importance of interaction between gp120 and gp41 for determination of the neutralization phenotype has been studied. One aspect of the invention relates to a chimeric fusion protein useful as an immunogen for inducing HIV antigen-specific immune responses. The chimeric contains: (a) a first polypeptidyl region containing a *Pseudomonas Exotoxin* A (PE) binding domain and a PE translocation domain, located at the N-terminus of the fusion protein; and (b) a second polypeptidyl region located at the C-terminus of the fusion protein, including: (i) a first peptidyl segment containing a fragment of gp120 C1 domain, located at the N-terminus of the second polypeptidyl region; (ii) a second peptidyl segment containing a fragment of gp120 C5 domain, located at the C-terminus of the first peptidyl segment; and (iii) a third peptidyl segment containing a fragment of gp41 amino acid sequence, located at the C-terminus of the second peptidyl segment, wherein the second polypeptidyl region contains an antigenic determinant which is specific to one subtype of HIV. The one subtype of HIV is at least one selected from the group consisting of HIV subtypes A, B, C, D, E, F, G, H, J and K.

In one embodiment of the invention, the fusion protein further includes an endoplasmic reticulum retention sequence, e.g., the amino acid sequence KDEL, at the C-terminus. In another embodiment of the invention, the chimeric fusion protein further includes an intermediate polypeptidyl region between the first and the second polypeptidyl regions, in which the intermediate polypeptidyl region contains a non- Env, HIV antigenic determinant. In one embodiment of the invention, the intermediate polypeptidyl region is at least one selected from the group consisting of Gag24, Nef, Tat and Rev. In another embodiment of the invention, the intermediate polypeptidyl region includes Gag24 amino acid sequence or a fragment thereof. Further in another embodiment of the invention, the intermediate polypeptidyl region contains an N- or C-terminus of Gag24 amino acid sequence. In one embodiment of the invention, the intermediate polypeptidyl region contains the amino acid sequence set forth by SEQ ID NO: 151.

Another aspect of the invention relates to a chimeric HIV fusion protein useful as an immunogen for inducing HIV antigen-specific immune responses, which includes: (a) a first polypeptidyl region containing a PE binding domain and a PE translocation domain, located at the N-terminus of the fusion protein; and (b) a second polypeptidyl region containing an H Wherein, R¹ is a positively charged amino acid residue;

R² is a negatively charged amino acid residue;

R³ is a negatively charged amino acid residue;

R⁴ is L;

R⁵ is a positively charged amino acid residue; and n is 0 or 1.

Preferably, the carboxyl terminal moiety is a member of the KDEL family protein. As used herein, the term "KDEL family protein" refers to a group of proteins, which has a similar carboxyl end binding to the ER membrane of a cell and further has an ability for retention of such protein in the ER lumen. Generally, the length of the carboxyl end ranges from 4 to 16 residues. As discussed in U.S. Pat. No. 5,705,163 (which is incorporated herein by reference in its entirety), the amino residues at the carboxyl end of a KDEL family protein, particularly those in the last five amino acids, are important. As shown in the studies on the similar sequences present in different molecules and performing a specific biological function, a sequence that retains a newly formed protein within the endoplasmic reticulum is Lys Asp Glu Leu (KDEL). These findings suggest that the sequence at the carboxyl end of the fusion antigen according to the invention acts as some type of recognition sequence to assist translocation of the fusion antigen from an endocytic compartment into the ER and retains it in the lumen. The carboxyl terminal moiety comprises the sequence of KDEL. For example, the carboxyl terminal moiety may comprise the sequence of KKDLRDELKDEL (SEQ ID NO: 250), KKDEL-RDELKDEL (SEQ ID NO: 251), KKDELRVELKDEL (SEQ ID NO: 252), or KKDELRXELKDEL, in which R is D or V.

The terms "PE(ΔIII)-HIV gp120" and "PE(ΔIII)-HIV gp120 V3-V3" are interchangeable.

The terms "PE(ΔIII)-HIV gp120-41" and "PE(ΔIII)-HIV gp 120 C1-C5-gp41" are interchangeable.

The terms "HIV subtype A gp120 C1-C5-gp41" and "chimera A" are interchangeable; the terms "HIV subtype B gp120 C1-C5-gp41" and "chimera B" are interchangeable; the terms "HIV subtype C gp120 C1-C5-gp41" and "chimera C" are interchangeable, and so on.

Immunogens. To be an immunogen, the formulation need only be a mixture of a fusion protein construct as described herein and a biocompatible carrier fluid suitable for carrying and delivering a predetermined aliquot of the fusion protein construct to a prechosen site in the body of a living subject. Immunogens embodying the invention can be administered in any appropriate carrier for intradermal, subcutaneous, intramuscular, parenteral, intranasal, intravaginal, intrarectal, oral or intragastric administration. They can be introduced by any means that effect antigenicity in humans. The dosage administered will vary and be dependent upon the age, health, and weight of the recipient; the kind of concurrent treatment, if any; the frequency of treatment; and the nature of the humoral antibody response desired. If the immunogens are to be given intradermally, subcutaneously, intramuscularly, intravenously or parenterally, they will be prepared in sterile form; in multiple or single dose formats; and dispersed in a fluid carrier such as sterile physiological saline or 5% dextrose solutions commonly used with injectables. In addition, other methods of administration can be advantageously employed as well.

Vaccines. To be a prepared vaccine, the minimal formulation comprises a predetermined quantity of a fusion protein construct as described herein; a biocompatible carrier suitable for carrying and delivering a predetermined aliquot of a fusion protein construct to a prechosen site in the body of a living subject; and at least one adjuvant composition dispersed in the carrier fluid or coupled to the fusion protein construct. The vaccine, by definition, incorporates an immunogen and includes one or more adjuvants to facilitate or stimulate the immune response and to prolong the antigenic effect in-vivo over time. Among the useful adjuvant substances conventionally known are those compositions approved by the FDA (currently or pending for systemic and/or mucosal immunizations). Some are preferred for mucosally-administered vaccines and others are preferred for intragastric administered vaccines.

Modes of administration. Multiple modes of inoculation, the manner of introducing an immunogen or vaccine, are conventionally known and used. The systemic or parenteral forms of administration (introduction by injection or perfusion) typically include intraperitoneal, intravenous, intramuscular, subcutaneous, and subdermal inoculations. In contrast, mucosal modes of administration may include not only the intranasal and intragastric forms of introduction, but also oral, intravaginal, and intrarectal introductions.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

I. HIV-1 gp120 and gp41 Fusion Proteins

Example 1

Selection of Truncated Segments from HIV Env Proteins, gp120 and gp41

The amino acid sequences of HIV gp120 and gp41 were retrieved from the National Center of Biotechnology Information (NCBI, USA) database and entered into software for evaluation of antigenic determinant (epitopes) of the target proteins, and candidate segments for synthesis displayed on an evaluation plot. Antigenic determinant regions of the target protein were chosen for synthesis by a reverse genetic engineering technique. Several peptide segments were selected as target peptides based on the results of the evaluation software. The software DNA strider v1.0 was used to analyze whether the nucleotide sequences of the target peptides contained restriction enzyme sites. If present in the DNA sequence in disadvantageous places, changes were made within the appropriate codons without altering the amino acid sequence. The software checked the newly created sequence, and designed restriction sites at both termini of the DNA sequence to facilitate cloning. Codons for some amino acid residues, such as Arg, Ile, Gln, Pro, were modified to increase the expression of proteins in *E. coli* expression systems. Table 1 lists the selected peptide segments and their corresponding amino acid sequences.

Example 2

Construction of Chimeric Target Polypeptides gp120 V3-V3 and gp120 C1-C5-gp41

Two target peptides gp 120 V3-V3 and gp120 C1-C5-gp41 were constructed using the selected peptide segments as follows: Three truncated peptide segments having the amino acid sequences of SEQ ID NO. 1 (from gp120 C1 domain), SEQ ID NO. 2 (from gp120 C5 domain) and SEQ ID NO. 5 (from gp41 region associated with gp120), respectively, were ligated to form a chimeric target peptide gp120 C1-C5-gp41 (referred to as gp120-41). Two truncated segments having amino acid sequences of SEQ ID NOs: 3 and 4 (both from gp 120 V3 domains), respectively, were fused to form polypeptide gp 120 V3-V3 (referred to as gp120). One or more residues might be inserted in-between to link two peptide segments. The number of residues inserted in-between was about 1 to 15 amino acids, which might be selected from amino acid residues that would not alter the secondary structure of proteins, such as glycine, alanine, valine, and leucine. The amino acid residue cysteine in SEQ ID NO: 2 and in SEQ ID NO: 5 could form a disulfide bond so that the chimeric target peptide generated could possess a three-dimensional structure.

domain of gp120, and the chimera gp120 C1-C5-gp41 (SEQ ID NO: 7) was based on simulation of the gp41 region in association with gp120. The chimera gp120 V3-V3 (SEQ ID NO: 6) comprises amino acid sequences of SEQ ID NOs: 3 and 4 (both from gp120 V3 domains). The chimera gp120 C1-C5-gp41 comprises amino acid sequences of SEQ ID NOs: 1 (from gp120 C1 domain), 2 (from gp120 C5 domain), and 5 (gp41 region in junction with gp120) (Table 1). Disulfide bonds were formed due to cysteines in SEQ ID NO: 2 (from the C5 domain of gp120) and SEQ ID No. 5 (from gp41 region in junction with gp120).

Using the similar method as described above, the following chimeric target peptides were constructed: HIV subtype A gp120 C1-C5-gp41; HIV subtype B gp120 C1-C5-gp41; HIV subtype C gp120 C1-C5-gp41; HIV subtype D gp120 C1-C5-gp41; HIV subtype E gp120 C1-C5-gp41; HIV subtype F gp120 C1-C5-gp41; HIV subtype G gp120 C1-C5-gp41; HIV subtype H gp120 C1-C5-gp41; HIV subtype J gp 120 C1-C5-gp41; and HIV subtype K gp 120 C1-C5-gp41 (abbreviated as chimeric target peptides A, B, C, D, E, F, G, H, J, and K, respectively).

These chimeras A, B, C, D, E, F, G, H, J and K were each constructed from a combination of 3 peptide segments selected from each corresponding HIV-1 subtypes, A, B, C, D, F, G, H, J and K, respectively. The basic scheme of the construction was to link two peptide segments, each selected

TABLE 1

| HIV Env Proteins | Target peptide segments | Sequence of selected peptide segments | SEQ ID No. |
|---|---|---|---|
| gp120 | C1 domain | VEKLWVTVYYGVPVWK | 1 |
|  | C5 domain | KVVKIEPLGVAPTKCKRRVVQREKR | 2 |
|  | V3 domain | CTRPSNNTRKGIHMGPGGAFYTTGQIIRNIRQAHC | 3 |
|  | V3 domain | CTRPNNNTRRSIHIEPEGAFYTTGEIIGDIRQAHC | 4 |
| gp41 | gp 41 region in association with gp120 | QARVIAVERYLKDQQLLGIWGGSGKLICCTTAVP WNSSWSNKLDRIWNNMTW<u>LE</u> | 5 |

TABLE 2

| Chimeric target peptide | Amino acid sequence | SEQ ID No. |
|---|---|---|
| gp120 V3-V3 | <u>IG</u>CTRPSNNTRKGIHMGPGGAFYTTGQIIRNIRQAHCGLLGGC *TRPNNNTRRSIHIEPEGAFYTTGEIIGDIRQAHC*<u>GLGLE</u> | 6 |
| gp120 C1-C5-gp41 | VEKLWVTVYYGVPVWKKVVKIEPLGVAPTKCKRRVVQREKR GGGGG*QARVIAVERYLKDQQLIGIWGGSGKLICCTTAVPWNSSW SNKLDRIWNNMTW*<u>LE</u> | 7 |

Table 2 lists the amino acid sequences of the chimeric target peptides gp120 V3-V3 and gp120 C1-C5-gp41. For chimeric peptide gp120 V3-V3 in table 2: the underlined letters denote the restriction sites; bold letters denote the first V3 domain segment, bold and italic letters denote the second V3 domain segment. For chimeric peptide gp 120 C1-C5-gp41 in table 2: the bold letters denote the C1 domain segment; non-bold letters denote the C5 domain segment; non-bold and italic letters denote linkers; bold and italic letters denote the gp41 domain; and the underlined letters denote a restriction site.

The chimeric target peptide gp120 V3-V3 (SEQ ID NO: 6) was designed based on the construction of repeats in the V3 from the C1 and C5 domains of gp120, to another segment selected from the gp41 region in association with gp120 for each HIV-1 subtype. Thus, like the SEQ ID NO: 7, all these chimera target peptides have gp120-C1-C5-gp41-like structures.

Table 3 lists the amino acid sequences of these chimeras, in which the non-bold, italic letters denote a segment from the C1 domain, the bold letters denote a segment from the C5 domain, of HIV subtype A gp120 protein; the non-bold, non-italic letters GGGGG denote a linker, and the bold, italic letters denote a segment from HIV subtype A gp41 region in junction with gp120.

TABLE 3

| Chimera for HIV subtype | Amino Acid Sequence | SEQ ID NO. |
|---|---|---|
| A | AENLWVTVYYGVPIWKKVVKIEPLGVAPTKARRRVVEREKRGGGGG *Q ARVLAVERYLRDQQLLGIWGCSGKLICPTNVPWNSSWSNKSLDEIWE NWTW* | 31 |
| B | TEKLWVTVYYGVPVWKKVVKIEPLGIAPTKAKRRVVQREKRGGGGG *QARVLAIERYLRDQQLLGIWGCSGKLICTTTVPWNASWSNRSLDEIW DNMTW* | 32 |
| C | MGNLWVTVYYGVPVWKKYKVVEIKPLGVAPTKPKRRVVEREKRGGG GG *QTRVLAIERHLRDQQLLGIWGCSGKLICTTAVPWNSSWSNKSQEE IWDNMTW* | 33 |
| D | ADNLWVTVYYGVPVWKKVVQIEPLGVAPTRAKRRVVEREKRGGGGG *QARILAVERYLKDQQILGIWGCSGKHICTTNVPWNSSWSNRSLNEIW QNMTW* | 34 |
| E | SXNLWVTVYYGVPVWRKVVQIEPLGIAPTRPKRRVVEREKRGGGGG *Q ARVLAVERYLKDQKFIGLWGCSGKIICTTAVEWNSSWSN RSFEEIWNNM TW* | 35 |
| F | ADNLWVTVYYGVPVWKKVVEIEPLGVAPTKAKRQVVQREKRGGGGG *QARVLAVERYLKDQQILGIWGCSGKLICTTNVPWNSSWSNKSQEEIW NNMTW* | 36 |
| G | ASNNLWVTVYYGVPVWEDAKKVVKIKPLGVAPTKARRRVVGREKRG GGGG *QARVLAIERYLRDQQLLGIWGCSGKLICTTNVPWNASWSNKTY NDIWDNMTW* | 37 |
| H | VVGNLWVTVYYGVPVWKKVVKIEPLGVAPTEARRRVVEREKRGGGG G *QARVLAVERYLKDQQLLGIWGCSGKLICTTNVPWNSSWSNKSLDEI WDNMTWMEW* | 38 |
| J | AKEDLWVTVYYGVPVWKKVVEIEPLGVAPTKAKRRVVEREKRGGGG G *QARVLAVERYLKDQQLLGIWGCSGKLICTTNVPWNASWSNKSYEDI WENMTW* | 39 |
| K | IAANNLWVTVYYGVPVWKKVVQIEPLGIAPTRARRRVVQREKRGGGG G *RARVLAVERYLRDQQILGIWGCSGKLICTTNVPWNSSWSNKSQSEI WENMTW* | 40 |

Example 3

Synthesis of DNA Fragments Encoding Chimeric Target Polypeptides gp120 V3-V3 and gp120 C1-C5-gp41

The nucleotide sequences of the DNA fragments encoding chimeric target peptides gp 120 V3-V3 and gp120 C1-C5-gp41 were modified to increase translation efficiency without changing the amino acid sequences of the encoded proteins, using the method disclosed in Taiwan patent application No. 092126644, which is incorporated herein in its entirety by reference. The sequence modification allowed the encoded peptides or proteins to be efficiently expressed in *E. coli* pET plasmid expression system. Table 4 lists the modified sequences of the DNA fragments encoding the chimeric target peptides gp120 V3-V3 and gp120 C1-C5-gp41, in which non-italic, capital letters denote restriction enzyme linkers for EcoR1, Nde1 and Sal1 cutting sites, and italic, capital letters denote a XhoI restriction enzyme site.

TABLE 4

| Chimeric target peptide | Nucleotide sequence | SEQ ID No |
|---|---|---|
| gp120 V3-V3 | GAATTCCATATGGTCGACatcggttgcacccgtccgagcaacaacacccgtaaaggtatccac atgggcccgggtggtgctttctacaccaccggtcagatcatccgtaacatccgtcaggctcactgtggtc tgctgggtggttgtacccgtccgaacaacaacacccgtcgtagcatccacatcgaaccggaaggtgctt tctacaccaccggtgaaatcatcggtgacatccgtcaggctcactgtggcctgggt*CTCGAG* | 8 |
| gp120 C1-C5-gp41 | GAATTCCATATGGTCGACgttgaaaaactgtgggttaccgtttactacggtgttccggtttggaaa aaagttgttaaaatcgaaccgctgggtgttgctccgaccaaatgcaaacgtcgtgttgttcagcgtgaa agcgtggtggccggtggcggtcaagctcgtgttatcgctgttgaacgttacctgaaagaccagcagctgc tgggtatctgggtggtagcggtaaactgatctgctgcaccaccgctgttccgtggaacagcagctgga gcaacaaactggaccgtatctggaacaacatgacctgg*CTCGAG* | 9 |

Table 5 lists SEQ ID NOs. of respective primer pairs used for PCR synthesis of the DNA fragments encoding chimeric target peptides gp120 V3-V3 (SEQ ID NO: 8) and gp120

C1-C5-gp41 (SEQ ID NO: 9). Non-DNA-template PCR reactions were performed by continuously using forward and reverse primer pairs to PCR synthesize DNA fragments. In the first-round PCR, the 3' end of the first forward primer (F1) had about 10-15 bases that were complementary to those in the pairing reversed primer (R1). The PCR profile was as follows: 5 min at 95° C., 1 min at 94° C., 0.5 min at 55° C., 1 min at 72° C. for 20 cycles, and 1 min at 72° C. Following the first-round PCR, the 3' ends of the primer pairs (such as F2 and R2, F3 and R3, F4 and R4, or F5 and R5) had about 10-15 bases that were complementary to the previous round PCR product as a DNA template. After the first-round PCR, 0.01-1 μl of the product was used as the DNA template for the second-round PCR. The second primer pair, F2 and R2, were added in a suitable amount together with dNTPs, reagents and Pfu polymerase, and the second round PCR was performed. Other primers were subsequently added in this manner so that the final extended DNA fragments were synthesized. All the DNA fragments synthesized from each primer pair and each round of PCR were analyzed for the size by gel electrophoresis. The DNA fragment encoding each individual chimeric target peptide was synthesized in this manner until the final PCR product was extended to the expected size, e.g., 264 bp in the case of gp120 V3-V3.

The DNA fragments (Table 6) encoding each individual chimeric target peptides gp120 C1-C5-gp41 for HIV subtype A, B, C, D, E, F, G, H, J and K were synthesized in a manner similar to the method described above using primer pairs listed in Table 6.

TABLE 5

| Chimeric target peptide | primer pairs | Forward Primer | SEQ ID NO. | Reverse Primer | SEQ ID NO. |
|---|---|---|---|---|---|
| gp120 V3-V3 | P 1 | F1 | 10 | R1 | 15 |
| | P 2 | F2 | 11 | R2 | 16 |
| | P 3 | F3 | 12 | R3 | 17 |
| | P 4 | F4 | 13 | R4 | 18 |
| | P 5 | F5 | 14 | R5 | 19 |
| gp120 C1-C5-gp41 | P 1 | F1 | 20 | R1 | 24 |
| | P 2 | F2 | 21 | R2 | 25 |
| | P 3 | F3 | 22 | R3 | 26 |
| | P 4 | F4 | 23 | R4 | 27 |
| | P 5 | F4 | 23 | R5 | 28 |
| | P 6 | F4 | 23 | R6 | 29 |

Example 4

Construction of Plasmids for Expression of HIV Fusion Proteins PE(ΔIII)-gp120 V3-V3 and PE(ΔIII)-gp120 C1-C5-gp41

Various chimeric target polypeptides of HIV-1 Env proteins as described above were cloned and expressed as PE fusion proteins. Briefly, a polypeptide from *Pseudomonas Exotoxin* A, i.e., PE(ΔIII), which was devoid of cytotoxic domain 111, was fused to respective chimeric target polypeptides. Plasmid pPE(ΔIII) was constructed by inserting a DNA fragment encoding the binding domain I and translocation domain II of *Pseudomonas exotoxin* A into vector pET15a. A DNA sequence coding for a carboxyl terminal peptide that comprises the amino acid sequence KDEL (SEQ ID NO. 30) was ligated to the carboxyl terminal portion of the PE(ΔIII) gene, and generated plasmid pPE(ΔIII)-KDEL3 (referred to as pPE(ΔIII)-K3). The isolated DNA fragments generated by the PCR reaction were respectively digested by restriction enzymes EcoR I and Xho I, and then ligated to the EcoR I, Xho I sites of the plasmid pPE(ΔIII)-KDEL3, resulting in chimeric genes that would expressed target peptides as fusion proteins (Hung, C. F. et al (2001) "Cancer Immunotherapy Using a DNA Vaccine Encoding the Translocation Domain of a Bacterial Toxin Linked to a Tumor Antigen" *Cancer Research* 61:3698-3703).

The plasmid pPE(ΔIII)-HIV gp120 (FIG. 1A) encodes a fusion protein PE(ΔIII)-HIV gp120 V3-V3 (referred to as PE(ΔIII)-HIV gp120). The plasmid pPE(ΔIII)-HIV gp120-K3 (FIG. 1B) encodes a fusion protein PE(ΔIII)-HIV gp120 V3-V3-K3 (referred to as PE(ΔIII)-HIV gp120-K3). The plasmid pPE(ΔIII)-HIV gp120-41 (FIG. 1C) encodes fusion protein PE(ΔIII)-HIV gp120 C1-C5-gp41 (referred to as PE(ΔIII)-HIV gp120-41). The plasmid pPE(ΔIII)-HIV gp120-41-K3 (FIG. 1D) encodes the fusion protein PE(ΔIII)-HIV gp120 C1-C5-gp41-K3 (referred to as PE(ΔIII)-HIV gp120-41-K3). The resulting plasmids were respectively transformed into *E. coli* Jam 109 to obtain clones and maintain the clones therein. The Jam 109 strain could stably maintain the plasmid inside bacteria cells without protein expression.

TABLE 6

| Chimeric target peptide | Nucleotide Sequence ID NO. | primer pairs | Forward Primer | SEQ ID NO. | Reverse Primer | SEQ ID NO. |
|---|---|---|---|---|---|---|
| A | 41 | P 1 | F1 | 51 | R1 | 56 |
| | | P 2 | F2 | 52 | R2 | 57 |
| | | P 3 | F3 | 53 | R3 | 58 |
| | | P 4 | F4 | 54 | R4 | 59 |
| | | P 5 | F5 | 55 | R5 | 60 |
| B | 42 | P 1 | F1 | 61 | R1 | 66 |
| | | P 2 | F2 | 62 | R2 | 67 |
| | | P 3 | F3 | 63 | R3 | 68 |
| | | P 4 | F4 | 64 | R4 | 69 |
| | | P 5 | F5 | 65 | R5 | 70 |
| C | 43 | P 1 | F1 | 71 | R1 | 76 |
| | | P 2 | F2 | 72 | R2 | 77 |
| | | P 3 | F3 | 73 | R3 | 78 |
| | | P 4 | F4 | 74 | R4 | 79 |
| | | P 5 | F5 | 75 | R5 | 80 |
| D | 44 | P 1 | F1 | 81 | R1 | 86 |
| | | P 2 | F2 | 82 | R2 | 87 |
| | | P 3 | F3 | 83 | R3 | 88 |
| | | P 4 | F4 | 84 | R4 | 89 |
| | | P 5 | F5 | 85 | R5 | 90 |
| E | 45 | P 1 | F1 | 91 | R1 | 96 |
| | | P 2 | F2 | 92 | R2 | 97 |
| | | P 3 | F3 | 93 | R3 | 98 |
| | | P 4 | F4 | 94 | R4 | 99 |
| | | P 5 | F5 | 95 | R5 | 100 |
| F | 46 | P 1 | F1 | 101 | R1 | 106 |
| | | P 2 | F2 | 102 | R2 | 107 |
| | | P 3 | F3 | 103 | R3 | 108 |
| | | P 4 | F4 | 104 | R4 | 109 |
| | | P 5 | F5 | 105 | R5 | 110 |
| G | 47 | P 1 | F1 | 111 | R1 | 116 |
| | | P 2 | F2 | 112 | R2 | 117 |
| | | P 3 | F3 | 113 | R3 | 118 |
| | | P 4 | F4 | 114 | R4 | 119 |
| | | P 5 | F5 | 115 | R5 | 120 |
| H | 48 | P 1 | F1 | 121 | R1 | 126 |
| | | P 2 | F2 | 122 | R2 | 127 |
| | | P 3 | F3 | 123 | R3 | 128 |
| | | P 4 | F4 | 124 | R4 | 129 |
| | | P 5 | F5 | 125 | R5 | 130 |
| J | 49 | P 1 | F1 | 131 | R1 | 136 |
| | | P 2 | F2 | 132 | R2 | 137 |
| | | P 3 | F3 | 133 | R3 | 138 |
| | | P 4 | F4 | 134 | R4 | 139 |
| | | P 5 | F5 | 135 | R5 | 140 |
| K | 50 | P 1 | F1 | 141 | R1 | 146 |
| | | P 2 | F2 | 142 | R2 | 147 |
| | | P 3 | F3 | 143 | R3 | 148 |
| | | P 4 | F4 | 144 | R4 | 149 |
| | | P 5 | F5 | 145 | R5 | 150 |

Example 5

Expression and Analysis of Target Proteins

HIV-1 PE-fusion proteins were expressed in *E. coli* BL21 (DE3) plys cultures containing corresponding expression plasmids. Briefly, 5 ml of bacterial seeds (A600 of 1.0±0.3 O.D.) were inoculated into 250 ml of liquid broth (LB) supplemented with 500 µg/ml ampicillin and 50 ml of 10% glucose at 37° C. in a rotating incubator shaken at 150 rpm for 2-3 hours. Once $O.D._{600\ nm}$ reached 0.3±0.1, the bacterial culture was induced with isopropylthio-β-D-galactoside (IPTG; Promega, USA) at a final concentration of 0.1 to 2 mM at 37° C. in a rotating incubator shaken at 150 rpm for 2 hours for protein expression.

Bacterial cells were pelleted after the protein induction was completed. After freezing and thawing of the pellet, bacterial cells were lysed with a solution containing in 10 ml: 0.3 mg/ml lysozyme, 1 mM phenylmethylsulfonyl fluoride (PMSF) and 0.06 mg/ml DNase I at room temperature for 20 minutes, followed by addition of 1 ml of 10% Triton X-100 and incubation at room temperature for 10 minutes. The lysed cells were centrifuged at 12,000 g for 10 minutes, and pellets were washed by 1 M and 2 M urea solutions. Insoluble inclusion bodies containing recombinant proteins were collected and dissolved in 8 ml of 8M urea solution or in an alkaline solution (pH 10 to 12) containing 1 to 3 M urea, and purified using a commercial pET His-Tag purification column system. The protein inclusion bodies dissolved in the urea solution were loaded onto a 4 ml $Ni^{2+}$-nitrilotriacetic acid (Ni-NTA) resin affinity column, and the bound material eluted by different pH buffers (e.g. pH=8.0, 7.0, 6.5, 6.0, 5.4, and 3.5) containing 1 to 6 M urea with 0.1 to 0.3 M NaCl, 5 to 50 mM phosphate buffer, and 5 to 50 mM Tris.

The eluted proteins were analyzed by sodium dodecyl sulfate-polyacrylamide gel electrophoresis (SDS-PAGE), and stained with coomassie blue. The optical densities of the bands in the gels were measured with a densitometer for evaluation of protein quantities. The concentration of fusion proteins, e.g., PE(ΔIII)-HIV gp120 C1-C5-gp41-K3 (referred to as gp120-41-K3) and PE(ΔIII)-HIV gp120 V3-V3-K3 (referred to as gp120-K3), in the eluted samples were about 0.8 mg/ml.

Example 6

Antibody Assay

Materials and methods. Five PE-HIV envelope peptides were used: (1) PE(ΔIII)-HIV gp120; (2) PE(ΔIII)-HIV gp120-KDEL; (3) PE(ΔIII)-HIV gp120-41; and (4) PE(ΔIII)-HIV gp120-41-KDEL. An oil adjuvant, ISA 206, was used with each of the peptide immunogens in emulsified preparations for injection into mice.

Animals. BALB/c mice were purchased form Harlan laboratories and housed in the Laboratory animal Resources Facility of KUMC. All mice were used in accordance with AAALAC and the KUMC Institutional Animal Care and Use Committee guidelines.

Immunization of animals with PE-HIV-Env fusion protein vaccines. Four- to six-week old BALB/c mice were divided into 5 groups, with 6 mice per group. The animals in groups 1 to 5 received (1) PE(ΔIII)-HIV gp120, (2) PE(ΔIII)-HIV gp120-K3, (3) PE(ΔIII)-HIV gp120-41, (4) PE(ΔIII)-HIV gp120-41-K3, and (5) PBS (control group), in adjuvant, respectively, following the immunization schedule shown in Table 7. Immunized mice were then exsanguinated following deep anesthesia and blood and spleens were collected for immunological assays.

TABLE 7

| Group | No. of mice | Immunogen | Immunization Schedule 1$^{st}$ time *(IM) 0 week | 2$^{nd}$ time (IM) 2 weeks | 3$^{rd}$ time (IM) 4 weeks | 4$^{th}$ time (I/M) 6 weeks | 5$^{th}$ time **(IP) 8 weeks |
|---|---|---|---|---|---|---|---|
| 1 | 6 | PE(ΔIII)-HIV gp120 | 50 μg | 25 μg | 25 μg | 25 μg | 50 μg |
| | | Adjuvant | 50 μl | 50 μl | 50 μl | 50 μl | 0 |
| 2 | 6 | PE(ΔIII)-HIV gp120-K3 | 50 μg | 25 μg | 25 μg | 25 μg | 50 μg |
| | | Adjuvant | 50 μl | 50 μl | 50 μl | 50 μl | 0 |
| 3 | 6 | PE(ΔIII)-HIV gp120-41 | 50 μg | 25 μg | 25 μg | 25 μg | 50 μg |
| | | Adjuvant | 50 μl | 50 μl | 50 μl | 50 μl | 0 |
| 4 | 6 | PE(ΔIII)-HIV gp120-41-K3 | 50 μg | 25 μg | 25 μg | 25 μg | 50 μg |
| | | Adjuvant | 50 μl | 50 μl | 50 μl | 50 μl | 0 |
| 5 | 6 | PBS | 0 | 0 | 0 | 0 | 50 μl |
| | | Adjuvant | 50 μl | 50 μl | 50 μl | 50 μl | 0 |

*IM denotes intramuscular injection

**IP denotes intraperitoneal injection

Serum antibody binding assay. An ELISA test using a commercial kit was used to determine binding antibody titers. Briefly, two weeks after the last immunization, mice were anesthetized, sacrificed, and spleens and blood samples were collected. Sera prepared from the blood samples of the animals immunized with fusion proteins in groups 1 to 4 and animals in the placebo group were serially diluted 500×, 2500×, 12500×, and 62500×, respectively. Binding antibody titers induced by the four peptide groups were analyzed using ELISA kit (BioChain) for detection of anti-HIV antibodies. Plates were coated with HIV antigen. The manufacturer's protocol was modified for using mouse sera by substituting the anti-human antibody with a goat anti-mouse serum conjugated with Horseradish peroxidase (HRP). Results were expressed as OD absorbance at 450 nm against the blank. FIGS. 2A-2B illustrate the test results of sera from animals immunized with respective fusion proteins. The absorbance data reflects the amount of antibody titers in serum samples.

Figures 2A, 2B, 3:
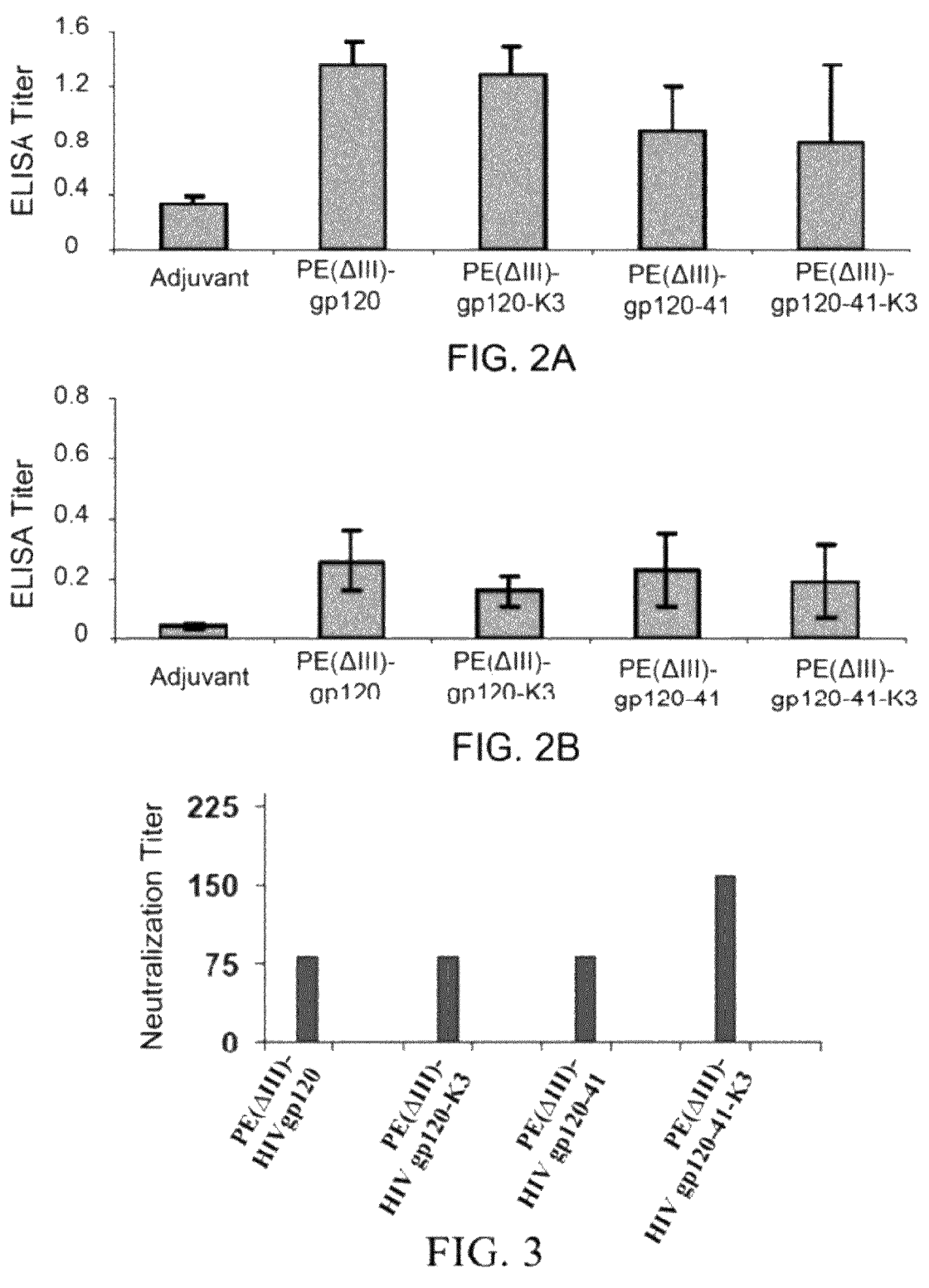

The result indicates that each fusion protein vaccine after being injected into animals was able to induce antibodies against HIV with good titers in the dilution of 1: 2,500 (FIG. 2A) and 12,500 (FIG. 2B).

Example 7

Immunized Mouse Sera Neutralize HIV-Attenuated Live Vaccine Virus

Neutralization assays were performed using mouse sera against an attenuated live SHIV vaccine virus that was developed in the MMD Lab. The assays were performed in X4 GHOST cells using a plaque reduction assay. X4 GHOST cells were capable of harboring HIV virus plaques after being infected by an HIV-attenuated live vaccine virus. Briefly, serum samples collected from immunized mice were tested for their contents of HIV specific neutralizing antibodies. Briefly, quadruplicates of serial twofold dilutions of sera in RPMI 1640 medium were prepared in 96-well plates. Twenty plaque-forming units of virus were incubated with the twofold dilutions of serum samples from each immunized mouse and a normal serum for two hours at 37 C, respectively. The suspensions were then inoculated onto monolayers of X4 GHOST cells that constitutively expressed the HIV LTR linked to GFP. These cultures were incubated for three days and then examined by immunofluorescence for determination of the numbers of fluorescence spots that represented successful virus hits. Neutralization titers of the serum samples were scored as the highest dilution of the immune serum sample that prevented development of 50% of the plaques induced with the control nonimmune serum. Mice developed neutralizing antibodies against the live vaccine virus (FIG. 3). The highest serum neutralization titers were obtained with sera from mice immunized with PE(ΔIII)-HIV gp120-41-KDEL.

Example 8

Immunized Mouse Eera Neutralize Simian-Human Immunodeficiency Virus (SHIV$_{KU2}$)

Immunization of animals. Mice were immunized with higher dosages of PE-fusion protein vaccines using a similar protocol described above. Briefly, mice were divided into 5 groups (groups 6-10), with 6 mice per group, and received PE(ΔIII)-HIV gp120, gp120-K3, PE(ΔIII)-HIV gp120-41, PE(ΔIII)-HIV gp120-41-K3, and PBS (control group), in adjuvant, respectively. The immunization schedule is shown in Table 8.

TABLE 8

| Group | No. of mice | Immunogen | Immunization | | |
|---|---|---|---|---|---|
| | | | First time *(IM) 0 week | Second time (IM) 2 weeks | Third time **(IP) 6 weeks |
| 6 | 6 | PE(ΔIII)-HIVgp120 | 100 μg | 50 μg | 50 μg |
| | | Adjuvant | 100 μl | 50 μl | 0 |
| 7 | 6 | PE(ΔIII)-HIVgp120-K3 | 100 μg | 50 μg | 50 μg |
| | | Adjuvant | 100 μl | 50 μl | 0 |
| 8 | 6 | PE(ΔIII)-HIVgp120-41 | 100 μg | 50 μg | 50 μg |
| | | Adjuvant | 100 μl | 50 μl | 0 |
| 9 | 6 | PE(ΔIII)-HIVgp120-41-K3 | 100 μg | 50 μg | 50 μg |
| | | Adjuvant | 100 μl | 50 μl | 0 |
| 10 | 6 | PBS | 100 μl | 50 μl | 50 μl |
| | | Adjuvant | 100 μl | 50 μl | 0 |

*IM: intramuscular injection with adjuvant ISA 206.
**IP: intraperitoneal injection with adjuvant ISA 206.

TABLE 9

| Group | Vaccine | No. of live mice/No. of challenged mice | Neutralization titer |
|---|---|---|---|
| 6 | PE(ΔIII)-HIV gp120 | 4/6 | 1:20 |
| 7 | PE(ΔIII)-HIV gp120-K3 | 1/6 | 1:20 |
| 8 | PE(ΔIII)-HIV gp120-41 | 5/6 | 1:20 |
| 9 | PE(ΔIII)-HIV gp120-41-K3 | 3/6 | 1:20-40 |
| 10 | PBS/adjuvant* | 0/6 | — |

*Adjuvant: ISA 206.

Two weeks after the third immunization, blood samples were collected from each group of animals and processed to obtain serum samples for assay of antibody titers. ELISA antibody assays showed similar titers in this experiment as those in Example 6.

To perform neutralization assays using SHIV$_{KU2}$, mice from each group were challenged by pathogenic SHIV$_{KU2}$ vaccine (constructed by Dr. Narayan, University of Kansas Medical Center, U.S. Pat. No. 5,849,994). All four groups of the immunized animals developed neutralizing antibody titers of approximate 1:20 against SHIV$_{KU2}$. Table 9 shows the survival data. PE(III) gp120-41 was the best antigen preparation for induction of neutralizing antibodies against SHIV$_{KU2}$ since 5 out of 6 mice developed these antibodies.

Example 9

HIV Gag24, Nef, Tat, and Rev Fusion Proteins

Materials and methods. Four HIV fusion proteins were tested for their immunogenicity: (I) HIV Gag24 fusion protein vaccines, PE(ΔIII)-HIV Gag24-K3 and PE(ΔIII)-HIV Gag24-gp120-41-K3; (II) HIV Nef fusion protein vaccines comprising PE(ΔIII)-HIV Nef-N-K3 and PE(ΔIII)-HIV Nef-C-K3; (III) HIV Tat fusion protein vaccine comprising PE(ΔIII)-HIV tat-K3; and (IV) HIV Rev fusion protein vaccine comprising PE(ΔIII)-HIV Rev-K3. The above (I) to (IV) HIV fusion proteins were constructed using similar methods described in Examples 2 to 4. Briefly, various polypeptide segments (Table 10) were selected from HIV proteins Gag24, Nef, Tat and Rev, respectively.

TABLE 10

| HIV Proteins | Targeted peptide segments | Amino acid sequence | SEQ ID No. |
|---|---|---|---|
| Gag24 | Full length Gag24 | VDRDELKGIGMTNNPPIPVGEIYKRWIILGLNKIVRM YSPTMTNNPPIPVGEIYRWIILGLNKIVRMYSPT | 151 |
| Nef | Nef-N terminus | PTVRQRMDRTEPAAEGVGAVSRDLEKHGAITSSNTA ATNADCAWLEAQEEEEVGFPVRPQVPLRPMTYKAA VDISHFLKEKGGLEGLIYSQKRQEILDLWIYHTQGYF PDWQNYTPGPGIRYPLTFGWCFKL | 152 |
| | Nef-C terminus | FLKVPVDPEQVEKANEGDNNCLLHPISQHGMDDPE KEVLMWKFDSRLAFQHIAREKHPEYYKDCLG | 153 |
| Tat | Full length Tat | RDELKGIGMEPVDPRLEPWKHPGSQPRTACNNCYC KKCCFHCPVCFISKGLGISYGRKKRRQRRRAPQDSE THQVSLSKQPTSQLRGDPTGPKESKKKVERETETDP NV | 154 |
| Rev | Full length Rev | LLAVRIIKTLYQSNPYPKPEGYRRVRRNRRRRWRAR QRQIHSISERILITCLGRPTEPVPLQLPPIERLNINCSES GGTSGTQRVGNP | 155 |

TABLE 11

| Target peptide | Nucleotide Sequence ID NO. | primer pairs | Forward Primer | SEQ ID NO. | Reverse Primer | SEQ ID NO. |
|---|---|---|---|---|---|---|
| Gag24 | 156 | P1 | F1 | 161 | R1 | 165 |
| | | P2 | F2 | 162 | R2 | 166 |
| | | P3 | F3 | 163 | R3 | 167 |
| | | P4 | F4 | 164 | R4 | 168 |
| Nef-N terminus | 157 | P1 | F1 | 169 | R1 | 176 |
| | | P2 | F2 | 170 | R2 | 177 |
| | | P3 | F3 | 171 | R3 | 178 |
| | | P4 | F4 | 172 | R4 | 179 |
| | | P5 | F5 | 173 | R5 | 180 |
| | | P6 | F6 | 174 | R6 | 181 |
| | | P7 | F7 | 175 | R7 | 182 |
| | | P8 | F7 | 175 | R8 | 183 |
| | | P9 | F7 | 175 | R9 | 184 |
| Nef-C terminus | 158 | P1 | F1 | 185 | R1 | 189 |
| | | P2 | F2 | 186 | R2 | 190 |
| | | P3 | F3 | 187 | R3 | 191 |
| | | P4 | F4 | 188 | R4 | 192 |
| Tat | 159 | P1 | F1 | 193 | R1 | 200 |
| | | P2 | F2 | 194 | R2 | 201 |
| | | P3 | F3 | 195 | R3 | 202 |
| | | P4 | F4 | 196 | R4 | 203 |
| | | P5 | F5 | 197 | R5 | 204 |
| | | P6 | F6 | 198 | R6 | 205 |
| | | P7 | F7 | 199 | R7 | 206 |
| Rev | 160 | P1 | F1 | 207 | R1 | 213 |
| | | P2 | F2 | 208 | R2 | 214 |
| | | P3 | F3 | 209 | R3 | 215 |
| | | P4 | F4 | 210 | R4 | 216 |
| | | P5 | F5 | 211 | R5 | 217 |
| | | P6 | F6 | 212 | R5 | 217 |

Figure 1E:
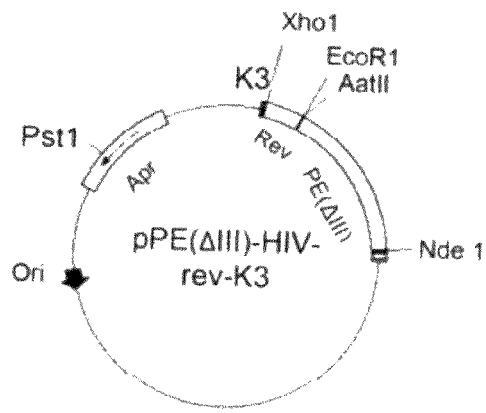
Figure 1F:
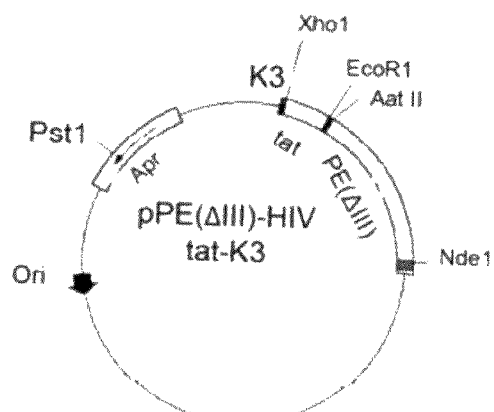
Figure 4:
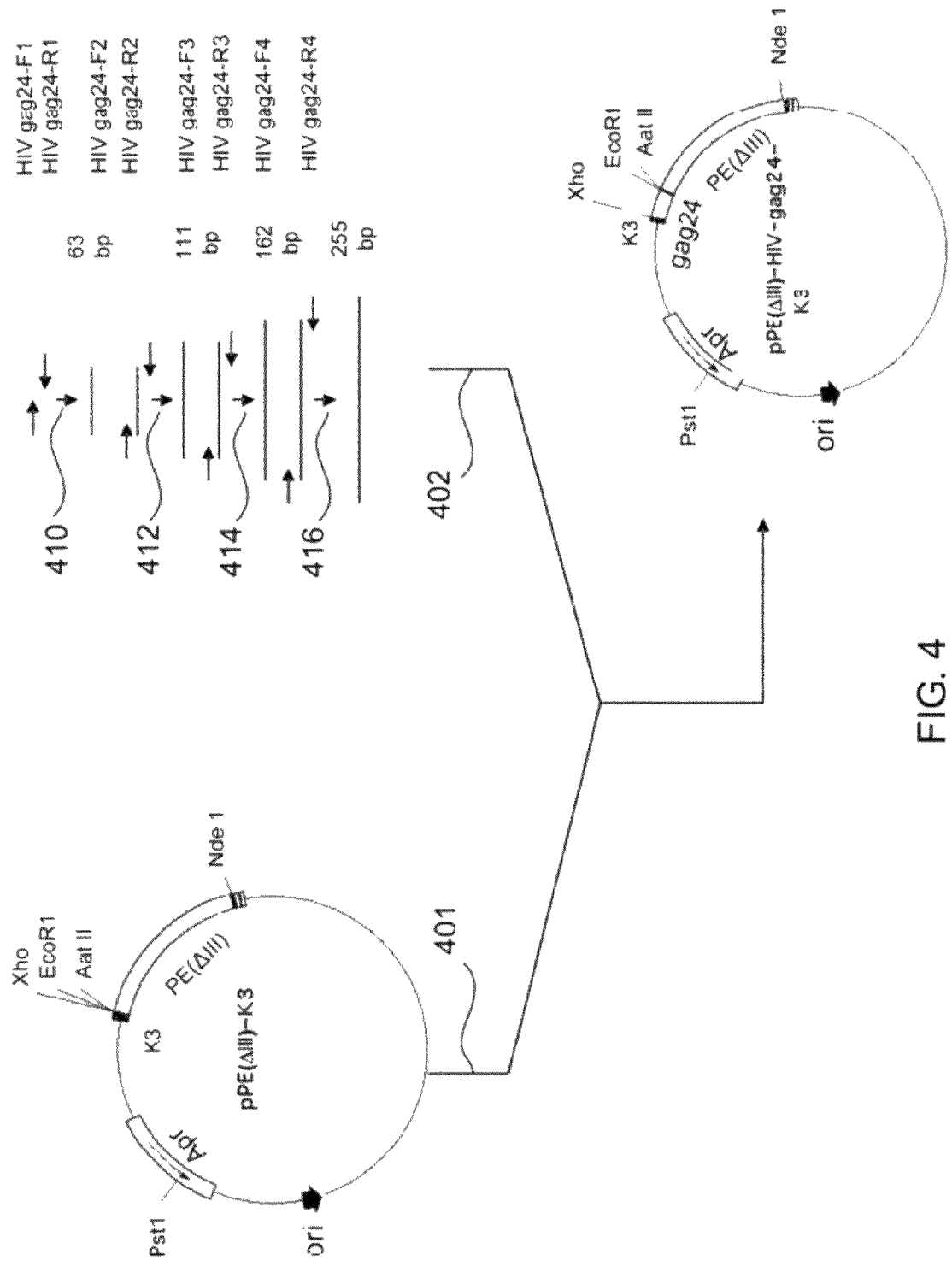
Figure 5:
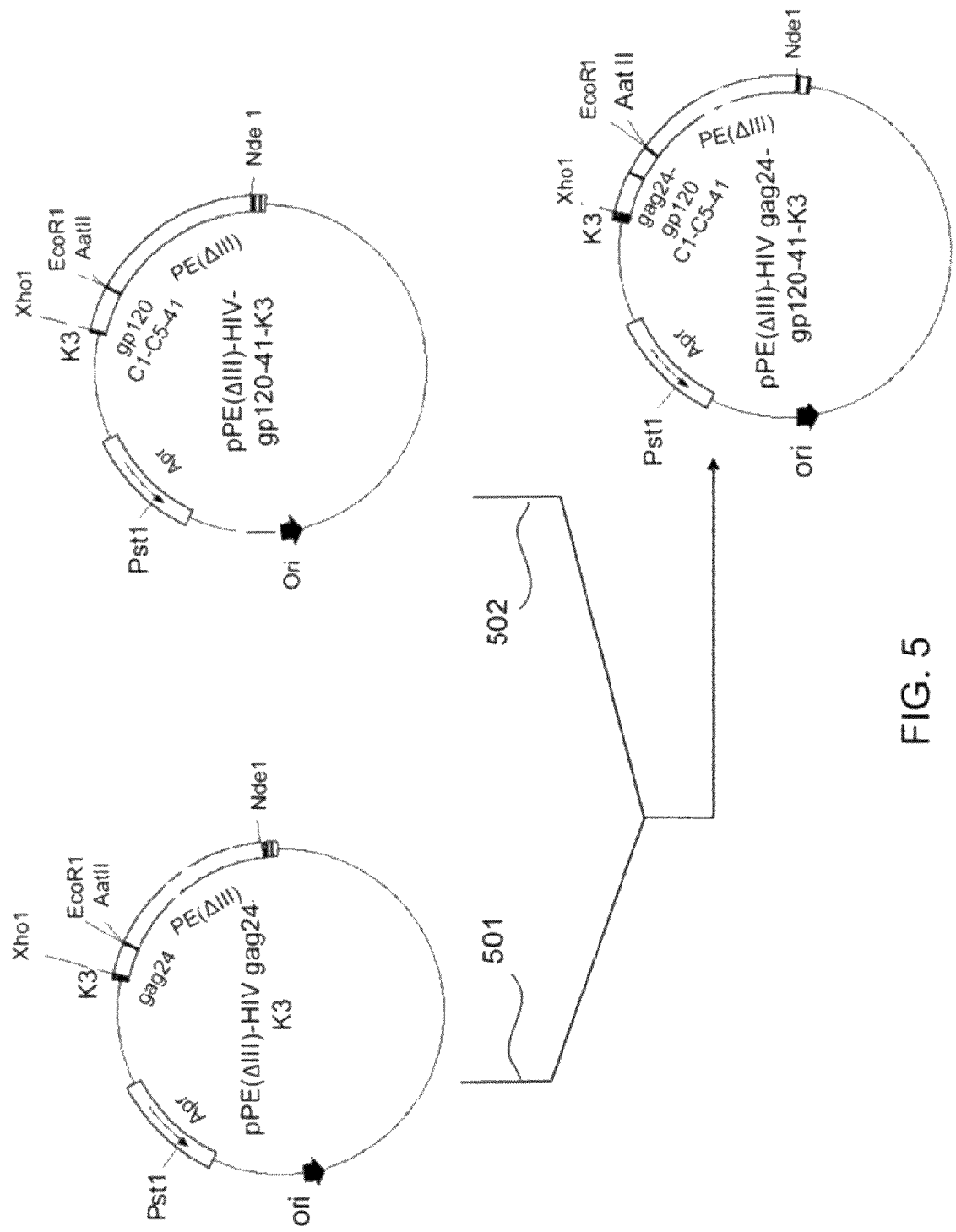

The DNA fragments (Table 11) encoding respective polypeptide segments were synthesized using primers listed in Table 11 by multi-round PCR synthesis method as described previously. Gel electrophoresis experiments were performed to examine the PCR products generated by each primer pair in the multiple-round PCR synthesis of DNA fragments, e.g., 410, 412, 414, 416 (FIG. 4). The PCR synthesized DNA fragments were fused to a PE fragment, cloned and expressed, respectively, using a similar method described in Example 4. The PE fragment is a polypeptide called PE (ΔIII) that contains a binding domain and a translocation domain from Pseudomonas Exotoxin A but lacks a cytotoxic domain. For example, the DNA fragment encoding gag24 generated by PCR was digested by restriction enzymes EcoRI and Xho I to isolate a 225 bp fragment, 402, which was ligated to a PE(ΔIII) fragment within an EcoRI and Xho I-digested plasmid pPE(ΔIII)-KDEL3, 401, to generate pPE(ΔIII)-HIV-gag24-K3 (FIG. 4).

A 1.7 Kb gp120-41 fragment, isolated from Sal I and Pst I-digested pPE(ΔIII)-HIV gp120-41-K3, 502, was fused to gag24 by inserting downstream, or C-terminal, to the gag24 gene within a Pst I, Xho I-digested plasmid pPE(ΔIII)-HIV gag24-K3, 501, to generate plasmid pPE(AH1)-HIV gag24-gp120-41-K3 (FIG. 5). Plasmid pPE(ΔIII)-HIV nef-C-K3 was digested by Sal I and Pst I to isolate a 1.6 Kb fragment, 702, followed by ligation to a nef-N fragment within a Pst I, Xho I-digested plasmid pPE(ΔIII)-HIV nef-N-KDEL, 701, to generate pPE(ΔIII)-HIV nef-NC-KDEL (FIG. 7).

The DNA fragment encoding Tat or Rev generated by PCR was digested by restriction enzymes EcoRI and Xho I to isolate fragment, which was ligated to a PE(ΔIII) fragment within an EcoRI and Xho I-digested plasmid pPE(ΔIII)-KDEL3. By employing DNA recombinant method, plasmids pPE(ΔIII)-HIV Tat-K3 (FIG. 1F), and pPE(ΔIII)-HIV Rev-K3 (FIG. 1E) were generated.

The sequence KDEL3 (i.e., K3) is an endoplasmic reticulum (ER) retention peptide located at the carboxyl terminal portion of the chimeric fusion protein. The sequence listing illustrates the nucleotide sequences of PE(ΔIII)-HIV Gag24-K3, PE(ΔIII)-HIV gag24-gp120-41-K3, PE-(ΔIII)-HIV nef-N-K3, pPE(ΔIII)-HIV nef-C-K3, pPE(ΔIII)-HIV-nef-NC-K3, pPE(III)-HIV rev-K3, pPE(ΔIII)-HIV-tat-K3 as SEQ ID NOs: 236, 238, 240, 242, 244, 246 and 248, and the corresponding amino acid sequences as SEQ ID NOs: 237, 239, 241, 243, 245, 247, and 249, respectively. For clinical applications, any undesired sequence such as oncogen sequences, if present in the bridge between PE(ΔIII) and HIV target peptide (e.g., between EcoRI and AatII), may be deleted without affecting the HIV target antigenic determinants.

Immunization of animals with fusion proteins. Chimeric fusion proteins as described above were expressed for vaccination. Female mice C57BL/6J aged 6- to 8-week old were purchased from National Taiwan University (Taipei, Taiwan) and bred in Animal Center of National Taiwan University Hospital. Mice were divided into groups and injected three times at two-week intervals with respective fusion proteins or PBS (control group) in ISA 206 oil adjuvant (Table 12). Two weeks after the last immunization, mice were exsanguinated under deep anesthesia and blood and spleens were collected for immunological assays. An ELISA test using a commercial kit was used to determine binding antibody titers.

TABLE 13

| Antigen peptide | Peptide sequence | SEQ ID NO. | Length (a.a.) |
|---|---|---|---|
| gp120-41-N1 | VEKLWVTVYYGVPVWK | 218 | 16 |
| gp120-41-N2 | KVVKIEPLGVAPTKCK | 219 | 16 |
| gp120-41-N3 | APTKCKRRVVQREKR | 220 | 15 |
| gp120-41-C1 | QARVWRYLKDQQLL | 221 | 14 |
| gp120-41-C2 | GIWGCSGKLICCTTAVP | 222 | 17 |
| gp120-41-C3 | AVPWNASSWSNKLDR | 223 | 15 |

TABLE 14

| Antigen peptide | Peptide sequence | SEQ ID NO. | Length (a.a.) |
|---|---|---|---|
| HIV-Tat-N | PVDPRLEPWKHPGSQPRTAC | 224 | 20 |
| HIV-Tat-C | QLRGDPTGPKESKKKVERET | 225 | 20 |
| HIV-Tat-M | SYGRKKRRQRRRAPQDSETH | 226 | 20 |
| HIV-Rev-N | QSNPYPKPEGYRRVRRNRRR | 227 | 20 |
| HIV-Rev-C | NCSESGGTSGTQRVGNPLEK | 228 | 20 |

TABLE 12

| HIV target peptides | Vaccine* | No. of Mice | Immunization Schedule<br>First time 0 week | Second time 2 weeks | Third time 4 weeks |
|---|---|---|---|---|---|
| Placebo | PBS/Adjuvant | 3 | 100 μl | 100 μl | 100 μl |
| Gag24 | PE(ΔIII)-HIV Gag24-K3 | 4 | 100 μg | 100 μg | 100 μg |
| gp120 | PE(ΔIII)-HIV gp120-41-K3 | 4 | 100 μg | 100 μg | 100 μg |
| Gag24-gp120-41 | PE(ΔIII)-HIV Gag24-gp120-41-K3 | 3 | 100 μg | 100 μg | 100 μg |
| Nef | PE(ΔIII)-HIV Nef-N-K3 | 4 | 100 μg | 100 μg | 100 μg |
| | PE(ΔIII)-HIV Nef-C-K3 | | (50 μg each) | (50 μg each) | (50 μg each) |
| Tat | PE(ΔIII)-HIV Tat-K3 | 4 | 100 μg | 100 μg | 100 μg |
| Rev | PE(ΔIII)-HIV Rev-K3 | 4 | 100 μg | 100 μg | 100 μg |

*Vaccines were prepared by mixing fusion proteins or PBS with 50 μl of adjuvant ISA 206 before intramuscular (IM) injection.

Serum Antibody Test. Sera from mice were prepared and serially diluted 500×, 2500×, 12500×, and 62500× using the method described in Example 5. Antibody titers were measured using indirect ELISA analysis. ELISA plates were prepared and coated with corresponding peptides in Tables 13 and 14.

Cytokine release assay. Splenocyte cytokine levels in the medium of cultured cells were examined by ELISA to measure levels of cytokines TNF-α, γ-IFN, IL-4, IL-10 and IL-12. Briefly, spleens were aseptically collected from mice and dissociated to harvest splenocytes. Cells were resuspended in RPMI, and mononuclear cells were counted in a hemocytomer. Splenocytes were diluted to an optimal density and cultured in $5\times10^6$ cells/well in 6-well plates in 5 ml of RPMI. Immunogen inducer peptides, e.g., Gag24-N and Gag24-C, etc., were respectively added to splenocytes in triplicate. On the second day after the addition of immunogens, supernatants were collected. The amounts of TNF-α, γ-IFN, IL-4, IL-10 and IL-12 produced by splenocyte CD8+ T cells were assayed using quantitative ELISA assay kits (Invitrogen BioSource) by following the manufacturer's protocol with slight modifications.

TABLE 14-continued

| Antigen peptide | Peptide sequence | SEQ ID NO. | Length (a.a.) |
|---|---|---|---|
| HIV-Nef-n1-N | SKLKKGWPTVRQRMDRTE | 229 | 18 |
| HIV-Nef-n1-C | TQGYFPDWQNYTPGPGIR | 230 | 18 |
| HIV-Nef-c1-N | VDPEQVEKANEGDNN | 231 | 15 |
| HIV-Nef-c1-M | ISQHGMDDPEKEVLM | 232 | 15 |
| HIV-Nef-c1-C | QHIAREKHPEYYKDCLGLEK | 233 | 20 |
| HIV-Gag24-N | PEFHMVDRDELKGIGMTN | 234 | 18 |
| HIV-Gag24-C | RMYSPTMTNNPPIPV | 235 | 15 |

Spleen lymphoid cell proliferation CMI assay. Cell proliferation ELISA BrdU (colorimetric) assays for CMI reactions were performed. The steps for culturing splenocytes were similar to those used in cytokine release assay except that cells were cultured in 96-well plates. Briefly, immunogens or antigen peptides, e.g., Gag24-N, Gag24-C, etc., were respectively added to cell culture on day-2 to stimulate cell proliferation. ConA (10 μg/ml), as a positive control, was added to stimulate cell2s for one day. Cells were pulse-labeled with BrdU on day-3 at 37° C. for 12-24 hr. Only proliferating cells incorporated BrdU into their DNA. Cells were fixed with FixDenat solution. The FixDenat solution also denatured the genomic DNA, exposing the incorporated BrdU to immunodetection. The BrdU label in the DNA was located with a peroxidase-conjugated anti-BrdU antibody (anti-BrdU-POD). The bound anti-BrdU-POD was quantitated with a peroxidase substrate TMB by measuring absorbance at OD650 using ELISA plate reader.

Table 15 shows Gag24-specific antibodies titers in immunized mouse Sera. The antibody titer assay indicated that Gag24-N antigenic determinant or epitope peptide was stronger in inducing antibody reactions than the Gag24-C epitope peptide. The ability of Gag24-N peptide in inducing antibody titers was, however, weak when it was in the fusion protein PE(ΔIII)-Gag24-K3. Once the Gag24-N antigenic determinant peptide was modified to include polypeptide gp120 and gp41 α-helix to form fusion protein PE(ΔIII)-Gag24-gp120-41-K3, its ability of inducing Gag24-N-specific IgG increased significantly. Thus, the peptide Gag24-N could elicit a Th2 cell-dependent, antigenic determinant (or epitope)-specific humoral immune response.

TABLE 15**

| | | Antibody | | | | | | | | | | |
|---|---|---|---|---|---|---|---|---|---|---|---|---|
| | | IgG | | | | IgA | | | | IgE | | |
| | | | | | | Mouse No. | | | | | | |
| Vaccine | Coated Antigen | #1 | #2 | #3 | Pl* #1 | #1 | #2 | #3 | Pl #1 | #1 | #2 | #3 | Pl #1 |
| PE(ΔIII)- Gag24-K3 | Gag24-N | 10 | 10 | 10 | 1 | 3 | 3 | 3 | 1 | 1 | 1 | 3 | 1 |
| | Gag24-C | 3 | 3 | 3 | 1 | 10 | 3 | 3 | 1 | 1 | 3 | 1 | 1 |
| PE(ΔIII)- Gag24- gp120-41- K3 | Gag24-N | 100 | 100 | 100 | 1 | 3 | 3 | 3 | 1 | 3 | 3 | 3 | 1 |
| | Gag24-C | 3 | 3 | 10 | 1 | 3 | 3 | 3 | 1 | 1 | 1 | 1 | 1 |

*The term "Pl" denotes "placebo," in which mice were injected with PBS/adjuvant.
**The data represented here were endpoints of serum semi-log serial dilution. The experiments were repeated in three mice per immunogen inducer group.

Figure 6:
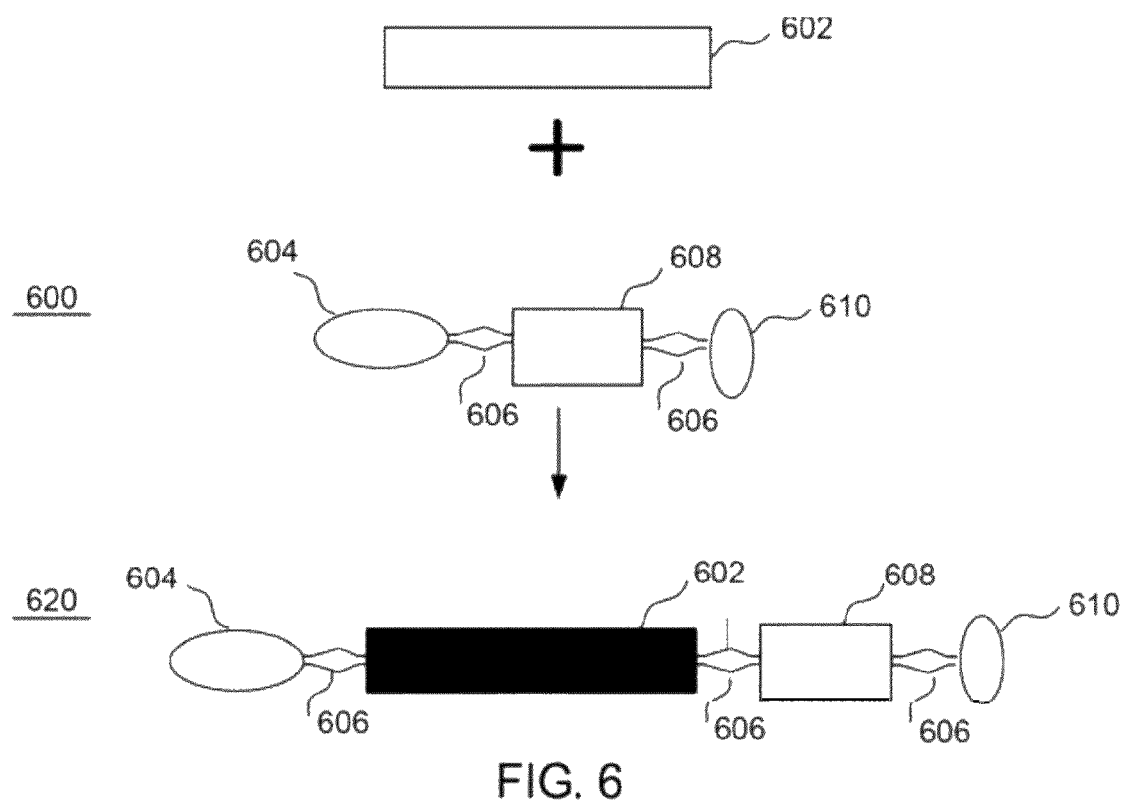
Figure 7:
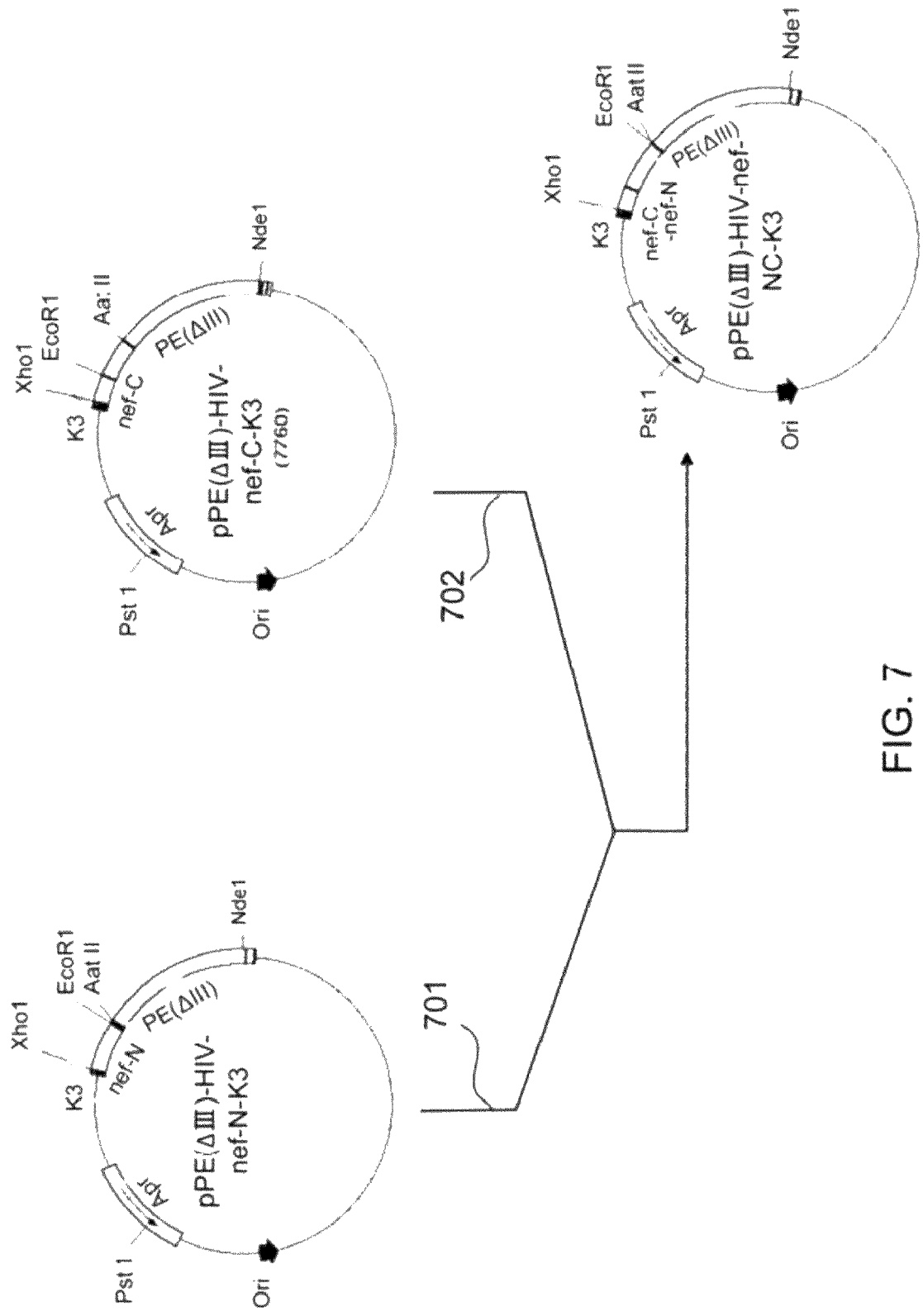

The results from the cell proliferation CMI assay indicated that both fusion proteins, PE(ΔIII)-Gag24-K3 and PE(ΔIII)-Gag24-gp120-41-K3, after being injected into mice could induce cell-mediated immune response to Gag24 antigen (Table 16). The Gag24 antigen, however, had a low efficacy in inducing cell-mediated immune responses in the fusion protein PE(ΔIII)-Gag24-K3. Once it was modified to fuse with gp120 C1 and C5 domains and gp41 α-helix to form PE(ΔIII)-Gag24-gp120 C1-C5-gp41-K3, Gag24 antigen's ability in inducing cell-mediated immune responses significantly increased. Thus, PE(ΔIII)-Gag24-gp120 C1-C5-gp4 1-K3 is much stronger than PE(ΔIII)-Gag24-K3 in inducing Gag24-specific, cell-mediated responses and cytokine release. As shown in FIG. 6, chimeric polypeptide HIV PE(ΔIII)-gp120 C1-C5-gp41 600 can act as a building unit for connecting other HIV antigenic determinant peptide 602 and thereby markedly enhance cell-mediated immune responses of the inserted HIV antigenic peptide 602, such as Gag24. Chimeric polypeptide HIV PE(ΔIII)-gp120 C1-C5-gp41 600 includes PE(6,III) 604, HIV gp 120 C1-C5-gp41 608, an endoplasmic reticulum retention sequence 610, with a bridge or linker 606 in-between. The fusion of an HIV antigenic determinant polypeptide 602 with weak CMI responses and HIV gp120 C1-C5-gp41 608 results in a chimeric PE-HIV fusion protein 620 that exhibits enhanced CMI responses specific to the antigenic determinant 602.

TABLE 16

CMI assay on immunized mouse splenocytes*

| | | Animal Group | |
|---|---|---|---|
| Fusion Protein Vaccine | Immunogen Inducer | Vaccine (n = 3) | Placebo (n = 3) |
| PE(ΔIII)-Gag24-K3 | Gag24-N | 0.32 | 0.19 |
| | Gag24-C | 0.65 | 0.26 |
| | ConA | 1.56 | 0.24 |
| PE(ΔIII)-Gag24- gp120-41-K3 | Gag24-N | 1.31 | 0.19 |
| | Gag24-C | 1.25 | 0.26 |
| | ConA | 1.42 | 0.20 |

The data from the cytokine induction test (Table 17) showed that both vaccines PE(ΔIII)-Gag24-K3 and PE(ΔIII)-Gag24-gp120-41-K3 after being injected into mice did not induce detectable IL-4, which indicated that they would be better vaccine candidates for HIV. Of the two fusion protein vaccines, PE(ΔIII)-Gag24-gp120-41-K3 was much more effective than PE(ΔIII)-Gag24-K3 in inducing splenocytes to produce large amounts of IL-10 and IL-12. A comparison of Gag24-N and Gag24-C peptides in their cytokine inducing effects showed that in the PE(ΔIII)-Gag24-K3 vaccine group, Gag24-C peptide appeared to have a stronger T-cell-dependent epitope effect than Gag24-N peptide. In the PE(ΔIII)-Gag24-gp120-41-K3 vaccine group, both Gag24-N and Gag24-C peptides were capable of inducing cell-mediated immune responses and had no difference in their effects in inducing cytokine release. The data indicated that fusion protein PE(ΔIII)-Gag24-K3 had a low efficacy in inducing Gag24-specific cytokine release; however, fusion protein PE(ΔIII)-Gag24-gp120-41-K3 had a strong effect in eliciting Gag24-specific immune responses.

TABLE 17

Cytokines release assay*

| Vaccine | Immunogen Inducer | TNF-α Vac** | TNF-α Plac** | γ-IFN Vac** | γ-IFN Plac** | IL-4 Vac** | IL-4 Plac** | IL-10 Vac** | IL-10 Plac** | IL-12 Vac** | IL-12 Plac** |
|---|---|---|---|---|---|---|---|---|---|---|---|
| PE(ΔIII)-Gag24-K3 | Gag24-N | 8.6 | 3.4 | 6.1 | 5.6 | 0 | 0 | 2 | 0 | 53.6 | 31.0 |
|  | Gag24-C | 12.9 | 9.6 | 12.8 | 12.8 | 0 | 0 | 12 | 8 | 36.5 | 35.6 |
|  | ConA | 143.1 | 53.4 | 206.4 | 81.2 | 9 | 0 | 9 | 4 | 60.0 | 36.1 |
| PE(ΔIII)-Gag24-gp120-41-K3 | Gag24-N | 70.0 | 3.4 | 17.5 | 5.6 | 0 | 0 | 136 | 0 | 87.6 | 31.0 |
|  | Gag24-C | 86.6 | 9.6 | 24.4 | 12.8 | 0 | 0 | 144 | 8 | 67.2 | 35.6 |
|  | ConA | 314 | 53.4 | 765.4 | 81.2 | 13.8 | 0 | 196 | 4 | 87.6 | 36.1 |

*The standard deviation is not shown here. The unit of the concentration is in pg/ml; n = 3 in both vaccine and placebo groups.

**The term "Vac" refers to "Vaccine," and "Plac" refers to "Placebo."

The data from the immunized mice Sera ELISA test indicated that the farthest C-terminal portion of Nef-C antigen determinant peptide had the strongest antibody reaction (Table 18). Based on the antibody-inducing reactions by fusion protein vaccine PE(ΔIII)-Nef-K3, it was concluded that peptide Nef-C-C was one of the Th2 cell-dependent, HIV antigenic determinant sites (Table 18).

TABLE 18**

Nef-specific antibody titers in HIV-Nef fusion protein-immunized mice

| Vaccine | Coated Antigen | IgG #1 | IgG #2 | IgG #3 | IgG P1* | IgA #1 | IgA #2 | IgA #3 | IgA P1 | IgE #1 | IgE #2 | IgE #3 | IgE P1 |
|---|---|---|---|---|---|---|---|---|---|---|---|---|---|
| PE(ΔIII)-Nef-N-K3 | Nef-N-N | 30 | 30 | 30 | 1 | 3 | 10 | 10 | 10 | 1 | 1 | 1 | 1 |
|  | Nef-N-C | 30 | 30 | 30 | 1 | 30 | 30 | 30 | 1 | 1 | 3 | 1 | 1 |
|  | Nef-C-N | 30 | 30 | 30 | 1 | 10 | 10 | 10 | 1 | 1 | 1 | 1 | 1 |
| PE(ΔIII)-Nef-C-K3 | Nef-C-M | 30 | 30 | 30 | 1 | 10 | 10 | 10 | 1 | 1 | 1 | 1 | 1 |
|  | Nef-C-C | $10^4$ | $10^3$ | 300 | 1 | $10^2$ | 10 | 10 | 1 | 1 | 1 | 1 | 1 |

*The term "P1" denotes "placebo #1." Mice in the placebo group were injected with PBS/adjuvant.

**The data represent the vaccinated mouse serum titers/placebo serum titers of the endpoints of serum semi-log serial dilution. The experiments were repeated in three mice per each vaccinated group.

TABLE 19

CMI assay on HIV-Nef fusion protein-immunized mouse splenocytes*

| Vaccine | Immunogen Inducer | Vaccine (n = 3) | Placebo (n = 3) |
|---|---|---|---|
| PE(ΔIII)-Nef-N-K3 and PE(ΔIII)-Nef-C-K3 | Nef-N-N | 0.7 | 0.3 |
|  | Nef-N-C | 0.8 | 0.2 |
|  | Nef-C-N | 0.5 | 0.3 |
|  | Nef-C-M | 0.7 | 0.2 |
|  | Nef-C-C | 1.0 | 0.3 |
|  | ConA | 0.7 | 0.3 |

The cell-mediated immune responses in immunized mice indicated that both PE(ΔIII)-Nef-N-K3 and PE(ΔIII)-Nef-C-

K3 had Nef-antigen-specific CMI reactions, and among which the Nef-N-C and Nef-C-C antigenic determinant portions induced stronger CMI responses (Table 19).

TABLE 20*

Cytokines release assay from HIV-Nef fusion protein-immunized mouse splenocytes

| Vaccine | Immunogen Inducer | Cytokine | | | | | | | | | |
|---|---|---|---|---|---|---|---|---|---|---|---|
| | | TNF-α | | γ-IFN | | IL-4 | | IL-10 | | IL-12 | |
| | | Animal Group | | | | | | | | | |
| | | Vac*** | Plc*** | Vac | Plc | Vac | Plc | Vac | Plc | Vac | Plc |
| Mixture of | Nef-N-N | 46.8 | 2.1 | 38.9 | 9.2 | 0 | 0 | | | | |
| PE(ΔIII)- | Nef-N-C | 42.8 | 4.9 | 34.4 | 26.7 | 0 | 0 | | | | |
| HIV-Nef-N-K3 | Nef-C-N | 65.2 | 12.7 | 61.7 | 30.9 | 0 | 0 | 143 | 0 | 55 | 38 |
| and | Nef-C-M | 47.8 | 6.9 | 27.0 | 17.4 | 0 | 0 | | | | |
| PE(ΔIII)- | Nef-C-C | 51.2 | 2.9 | 25.1 | 10.6 | 0 | 0 | | | | |
| HIV-Nef-C-K3 | ConA | 80.8 | 14.7 | 84.6 | 15.3 | 0 | 0 | 135 | 0 | 69 | 50 |
| | BK** | 61.2 | 10.5 | 46.3 | 22.5 | | | | | | |

*conc. (pg/ml); n = 3 in both vaccine and placebo group.
**BK refers to "Blank," in which no immunogen inducer was added into splenocytes.
***Vac refers to "Vaccine," and Plc refers to "Placebo."

The data from the cytokine induction test showed that Nef fusion proteins did not induce detectable Nef-specific IL-4, which was an indication that Nef fusion proteins would be better vaccine candidates against HIV. The data also indicated that a vaccine composition comprising fusion proteins PE(ΔIII)-HIV-Nef-N-K3 and PE(ΔIII)-HIV Nef-C could stimulate splenocytes to produce a higher amount of IL-10 (Table 20).

The results from serum antibody assay indicated that the N-terminal portion of HIV-1 Tat protein could induce remarkable antibody responses, while the mid-segment and C-terminal portions were weak in inducing antibody responses. Thus, the N-terminal portion of HIV Tat protein could elicit Th2 cell-dependent, antigenic determinant-specific humoral immunity (Table 21).

The results from the cell immune response indicated that PE(ΔIII)-Tat-K3 could induce cell mediated immune responses to all Tat protein segments, among which the N-terminus of Tat protein was stronger than mid- and C-terminal segments in inducing cell immune responses (Table 22).

TABLE 22

CMI assay on HIV-Tat-fusion protein immunized mouse splenocytes*

| | | Animal Groups | |
|---|---|---|---|
| Vaccine | Immunogen Inducer | Vaccine (n = 4) | Placebo (n = 4) |
| PE(ΔIII)-HIV-Tat-K3 | Tat-N | 1.1 | 0.2 |
| | Tat-M | 1.0 | 0.2 |
| | Tat-C | 0.5 | 0.2 |
| | ConA | 1.3 | 0.2 |

The results from cytokine release assay indicated that HIV Tat fusion protein was not able to induce a detectable level of Tat-specific IL-4. Its effects in inducing γ-IFN and TNF-α release were not obvious, either. The fusion protein PE-(ΔIII)-Tat-K3, however, was able to stimulate splenocytes to produce Tat-N terminus-specific IL-12. Thus, PE-(ΔIII)-Tat-K3 was still effective in inducing a cell immune response that

TABLE 21

Antibody titers in HIV-Tat-fusion protein-immunized mice

| | | Antibody | | | | | | | | | | | | | | |
|---|---|---|---|---|---|---|---|---|---|---|---|---|---|---|---|---|
| | | IgG | | | | | IgA | | | | | IgE | | | | |
| | Coated | Mouse No. | | | | | | | | | | | | | | |
| Vaccine | Antigen | #1 | #2 | #3 | #4 | P1 | #1 | #2 | #3 | #4 | P1 | #1 | #2 | #3 | #4 | P1 |
| PE (ΔIII)-HIV-Tat-K3 | Tat-N | $10^3$ | $10^3$ | $10^3$ | $10^3$ | 1 | $10^3$ | $10^3$ | $10^3$ | $10^3$ | 1 | ? | ? | 10 | 10 | 1 |
| | Tat-M | 10 | 10 | 10 | 10 | 1 | 3 | 3 | 3 | 3 | 1 | 3 | 3 | 3 | 3 | 1 |
| | Tat-C | 10 | 1 | 3 | 3 | 1 | 3 | 3 | 3 | 3 | 1 | 1 | 1 | 1 | 1 | 1 |

*The term "P1" refers to "placebo #1."
The data represent vaccinated mouse serum titers/placebo serum titers of the endpoints of serum semi-log serial dilution.

was specific to the N terminal portion of Tat and therefore the N-terminus of Tat could evoke Th1 cell-dependent, antigenic determinant-specific cell mediated immune responses in the PE delivery system of the present invention (Table 23).

The antibody data from PE(III)-Rev-K3 fusion protein-immunized mice model indicated that the antibody responses to HIV-Rev antigenic determinant peptide was not strong enough to confirm the locus of Th2 cell-dependent, antigenic determinant in Rev protein (Table 24).

TABLE 23

Cytokines release assay on HIV-Tat fusion protein immunized-mouse splenocytes*

| Vaccine | Immunogen Inducer | Cytokine | | | | | | | | | |
|---|---|---|---|---|---|---|---|---|---|---|---|
| | | TNF-α | | γ-IF2N | | IL-4 | | IL-10 | | IL-12 | |
| | | | | | | Animal Group | | | | | |
| | | Vac | Plac | Vac | Plac | Vac | Plac | Vac | Plac | Vac | Plac |
| PE(ΔIII)- | Tat-N | 10 | 5 | 0 | 18 | 0 | 1 | 6 | 0 | 41 | 10 |
| HIV- | Tat-M | 18 | 5 | 7 | 4 | — | — | — | — | — | — |
| Tat-K3 | Tat-C | 32 | 9 | 21 | 17 | — | — | — | — | — | — |
| | BK | 10 | 18 | 2 | 27 | — | — | — | — | — | — |
| | ConA | 155 | 27 | 243 | 81 | 33 | 0 | 48 | 25 | 55 | 27 |

*conc. (pg/ml); n = 3 in both vaccine (Vac) and placebo (Plac) group.

TABLE 24

Antibody titers in HIV-Rev fusion protein-immunized mice

| Vaccine | Immunogen | Antibody | | | | | | | | | | | | | | |
|---|---|---|---|---|---|---|---|---|---|---|---|---|---|---|---|
| | | IgG | | | | | IgA | | | | | IgE | | | | |
| | | | | | | | Mouse No. | | | | | | | | | |
| | | #1 | #2 | #3 | #4 | P1* | #1 | #2 | #3 | #4 | P1 | #1 | #2 | #3 | #4 | P1 |
| PE(III)-HIV- | HIV-Rev-N | 10 | 10 | 10 | 3 | 1 | 3 | 10 | 3 | 10 | 1 | 1 | 1 | 1 | 1 | 1 |
| Rev-K3 | HIV-Rev-C | 3 | 3 | 1 | 1 | 1 | 3 | 3 | 3 | 3 | 1 | 1 | 1 | 1 | 1 | 1 |

*The term "P1" denotes "placebo #1." Mice in the placebo group were injected with PBS/adjuvant. The data represent vaccinated mouse serum titers/placebo serum titers of the endpoints of serum semi-log serial dilution.

The data from cell immune responses in Table 25 indicated that PE(III)-Rev-K3 fusion protein vaccine was not able to induce cell immune response to Rev antigen. The cytokine release inducing test also gave the similar result. It showed no obvious effects in inducing TNF-α and γ-IFN release (Table 26). Thus, the fusion protein vaccine PE(ΔIII)-Rev-K3 might not be a good component in an HIV vaccine. However, whether Rev is able to elicit a CMI response under the condition of fusion with gp 120-41 in a PE delivery system remains to be investigated. A plasmid pPE(ΔIII)-HIV-Rev-gp120-41-K3 was constructed for investigation.

TABLE 25

CMI assay on HIV-Rev fusion protein-immunized mouse Splenocytes

| Vaccine | Immunogen Inducer | Animal Groups | |
|---|---|---|---|
| | | Vaccine (n = 3) | Placebo (n = 3) |
| PE(ΔIII)-HIV-Rev-K3 | Rev-N | 0.39 | 0.25 |
| | Rev-C | 0.39 | 0.24 |
| | ConA | 0.40 | 0.24 |

TABLE 26

Cytokines release assay on HIV-Rev fusion protein-immunized mouse Splenocytes*

| Vaccine | Immunogen Inducer | Cytokine | | | |
|---|---|---|---|---|---|
| | | TNF-α | | γ-IFN | |
| | | Animal Group | | | |
| | | Vaccine (n = 4) | Placebo (n = 4) | Vaccine (n = 4) | Placebo (n = 4) |
| PE(ΔIII)-HIV-Rev-K3 | Rev-N | 29 | 3 | 6 | 4 |
| | Rev-C | 30 | 3 | 7 | 5 |
| | BK | 38 | 4 | 9 | 7 |
| | ConA | 50 | 6 | 16 | 5 |

*conc. (pg/ml)

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein. All references cited and discussed in this specification are incorporated herein by reference in their entireties and to the same extent as if each reference was individually incorporated by reference.

What is claimed is:

1. A method for inducing HIV antigen-specific immune responses, comprising:
   administering to a subject in need thereof with an effective amount of a chimeric fusion protein comprising:
   a) a first polypeptidyl region comprising a *Pseudomonas Exotoxin* A (PE) binding domain and a PE translocation domain, located at the N-terminus of the fusion protein; and
   b) a second polypeptidyl region with a fusion peptide of HIV gp120-C1-C5-gp41 with the amino acid sequence of SEQ ID NO: 7.

2. A method as claimed in claim 1, wherein the fusion protein further comprises an endoplasmic reticulum retention sequence at the C-terminus of the fusion protein.

3. A method as claimed in claim 2, wherein the fusion protein further comprises an intermediate polypeptidyl region with the amino acid sequence of HIV Gag24 between the first and the second polypeptidyl regions.

4. A method as claimed in claim 2, wherein the endoplasmic reticulum retention sequence comprises the amino acid sequence KDEL.

5. A method for inducing neutralizing antibodies against HIV-1, comprising:
   administering to a subject in need thereof with an effective amount of a chimeric fusion protein comprising:
   a) a first polypeptidyl region comprising a *Pseudomonas Exotoxin* A (PE) binding domain and a PE translocation domain, located at the N-terminus of the fusion protein; and
   b) a second polypeptidyl region with a fusion peptide of HIV gp120-C1-C5-gp41 with the amino acid sequence of SEQ ID NO: 7.

6. A method as claimed in claim 5, wherein the fusion protein further comprises an endoplasmic reticulum retention sequence at the C-terminus of the fusion protein.

7. A method as claimed in claim 6, wherein the fusion protein further comprises an intermediate polypeptidyl region with the amino acid sequence of HIV Gag24 between the first and the second polypeptidyl regions.

8. A method as claimed in claim 7, wherein the endoplasmic reticulum retention sequence composes the amino acid sequence KDEL.

9. A chimeric fusion protein comprising:
   a) a first polypeptidyl region comprising a *Pseudomonas Exotoxin* A (PE) binding domain and a PIE translocation domain, located at the N-terminus of the fusion protein; and b) a second polypeptidyl region with a fusion peptide of HIV gp120-C1-C5-gp41 with the amino acid sequence of SEQ ID NO: 7.

10. A fusion protein as claimed in claim 9, further comprising an endoplasmic reticulum retention sequence at the C-terminus of the fusion protein.

11. A fusion protein as claimed in claim 10, further comprising an intermediate polypeptidyl region with the amino acid sequence of HIV Gag24 between the first and the second polypeptidyl regions.

12. A fusion protein as claimed in claim 10, wherein the endoplasmic reticulum retention sequence comprises the amino acid sequence KDEL.

* * * * *